US008144007B2

(12) United States Patent
Tuck et al.

(10) Patent No.: US 8,144,007 B2
(45) Date of Patent: Mar. 27, 2012

(54) RELATIONSHIP PREDICTION SYSTEM USING EXTERNAL DATABASES

(75) Inventors: Edward F. Tuck, West Covina, CA (US); Ann Tuck Baden, Berkeley Lake, GA (US); Thomas N. Giaccherini, Carmel Valley, CA (US)

(73) Assignee: Social Fabric Corporation, West Covina, CA (US)

( * ) Notice: Subject to any disclaimer, the term of this patent is extended or adjusted under 35 U.S.C. 154(b) by 86 days.

(21) Appl. No.: 12/799,210

(22) Filed: Apr. 19, 2010

(65) Prior Publication Data

US 2011/0178879 A1     Jul. 21, 2011

Related U.S. Application Data

(63) Continuation-in-part of application No. 11/239,603, filed on Sep. 28, 2005, now Pat. No. 7,969,301, and a continuation-in-part of application No. 11/286,143, filed on Nov. 23, 2005, now abandoned, and a continuation-in-part of application No. 11/360,025, filed on Feb. 21, 2006, now abandoned, and a continuation-in-part of application No. 11/405,001, filed on Apr. 14, 2006, now abandoned, and a continuation-in-part of application No. 11/514,285, filed on Aug. 30, 2006, now Pat. No. 7,592,910, and a continuation-in-part of application No. 11/881,153, filed on Jul. 24, 2007, now abandoned, and a continuation-in-part of application No. 12/290,877, filed on Nov. 3, 2008, and a continuation-in-part of application No. 12/313,263, filed on Nov. 17, 2008, and a continuation-in-part of application No. 12/590,433, filed on Nov. 5, 2009, now Pat. No. 7,940,174, and a continuation-in-part of application No. PCT/GB2006/003581, filed on Sep. 26, 2006, and a continuation-in-part of application No. PCT/GB2007/002836, filed on Jul. 26, 2007.

(51) Int. Cl.
*G08B 1/08* (2006.01)
(52) U.S. Cl. ........... 340/539.13; 340/539.1; 340/539.11; 340/573.1; 455/414.2; 455/418; 455/500
(58) Field of Classification Search ............... 340/539.1, 340/539.11, 539.13, 539.16, 539.21, 539.23, 340/505, 572.1, 572.4, 573.1; 455/414.2, 455/418, 500; 705/14
See application file for complete search history.

(56) References Cited

U.S. PATENT DOCUMENTS

2002/0120627 A1* 8/2002 Mankoff .................. 707/10
2006/0178986 A1* 8/2006 Giordano et al. ......... 705/40
* cited by examiner

*Primary Examiner* — Daryl Pope
(74) *Attorney, Agent, or Firm* — Thomas N. Giaccherini

(57) ABSTRACT

A Relationship Prediction System Using External Databases for providing a relationship prediction based on the correlation of personal characteristics and the analysis of genetic characteristics is disclosed. In one embodiment, a first person supplies descriptions of their own personal characteristics, as well as descriptions of the personal characteristics of their ideal match, to a website. The first person also furnishes an odor, tissue or fluid sample to a test facility, where genetic characteristics are analyzed and determined. A relationship match is then generated based on both a combination of both a positive correlation of the personal characteristics of the first person and second person, and a measured dissimilarity between the sequence of genetic characteristics of the first person and second person. In one embodiment, personal characteristics are obtained from one or more external webpages.

14 Claims, 70 Drawing Sheets

72 Dating Service and Laboratory Cooperative Tasks

MHC Allele Groups (2-Digit Alleles)

| | |
|---|---|
| HLA-A (506 alleles in 22 groups) | A*01, A*02, A*03, A*11, A*23, A*24, A*25, A*26, A*29, A*30, A*31, A*32, A*33, A*34, A*36, A*43, A*66, A*68, A*69, A*74, A*80, A*92 |
| HLA-B (851 alleles in 37 groups) | B*07, B*08, B*13, B*14, B*15, B*18, B*27, B*35, B*37, B*38, B*39, B*40, B*41, B*42, B*44, B*45, B*46, B*47, B*48, B*49, B*50, B*51, B*52, B*53, B*54, B*55, B*56, B*57, B*58, B*59, B*67, B*73, B*78, B*81, B*82, B*83, B*85 |
| HLA-DR 1 (476 alleles in 13 groups) | DR 1*01, DR 1*03, DR 1*04, DR 1*07, DR 1*08, DR 1*09, DR 1*10, DR 1*11, DR 1*12, DR *13, DR 1*14, DR 1*15, DR 1*16 |

John's Credit Card Statement

| PAYEE | DATE | AMOUNT |
|---|---|---|
| RUSCO'S ITALIAN RESTAURANT | 12/1 | $69.79 |
| JOE'S CLASSIC CAR PARTS | 12/2 | $225.17 |
| HAWAIIAN AIRLINES | 12/3 | $439.41 |

Mary's Credit Card Statement

| PAYEE | DATE | AMOUNT |
|---|---|---|
| MARIO'S ITALIAN RESTAURANT | 12/3 | $33.59 |
| LOLITA'S BEAUTY SALON | 12/4 | $50.00 |
| HONOLULU HOTELS | 12/6 | $200.00 |

PHOTO
JANE SMITH

| ORGANIZATIONS | HOBBIES | FAVORITES | STORES |
|---|---|---|---|
| State University | Skiing | Chinese Food | Macy's |
| United Way | Cooking | | Amazon |

154

PHOTO
JOE JONES

| MUSIC | SPORTS TEAMS | PRODUCTS | PLACES |
|---|---|---|---|
| Rolling Stones | Cubs | Ford Trucks | Chicago |
| | Bears | Wrangler Jeans | |

156

158

156

PHOTO

MINDY JAMES

| CELEBRITIES | TV SHOWS | HOBBIES | VOLUNTEERING |
| John Wayne | Gunsmoke | Sewing | ASPCA |
| Gary Cooper | | | |

158

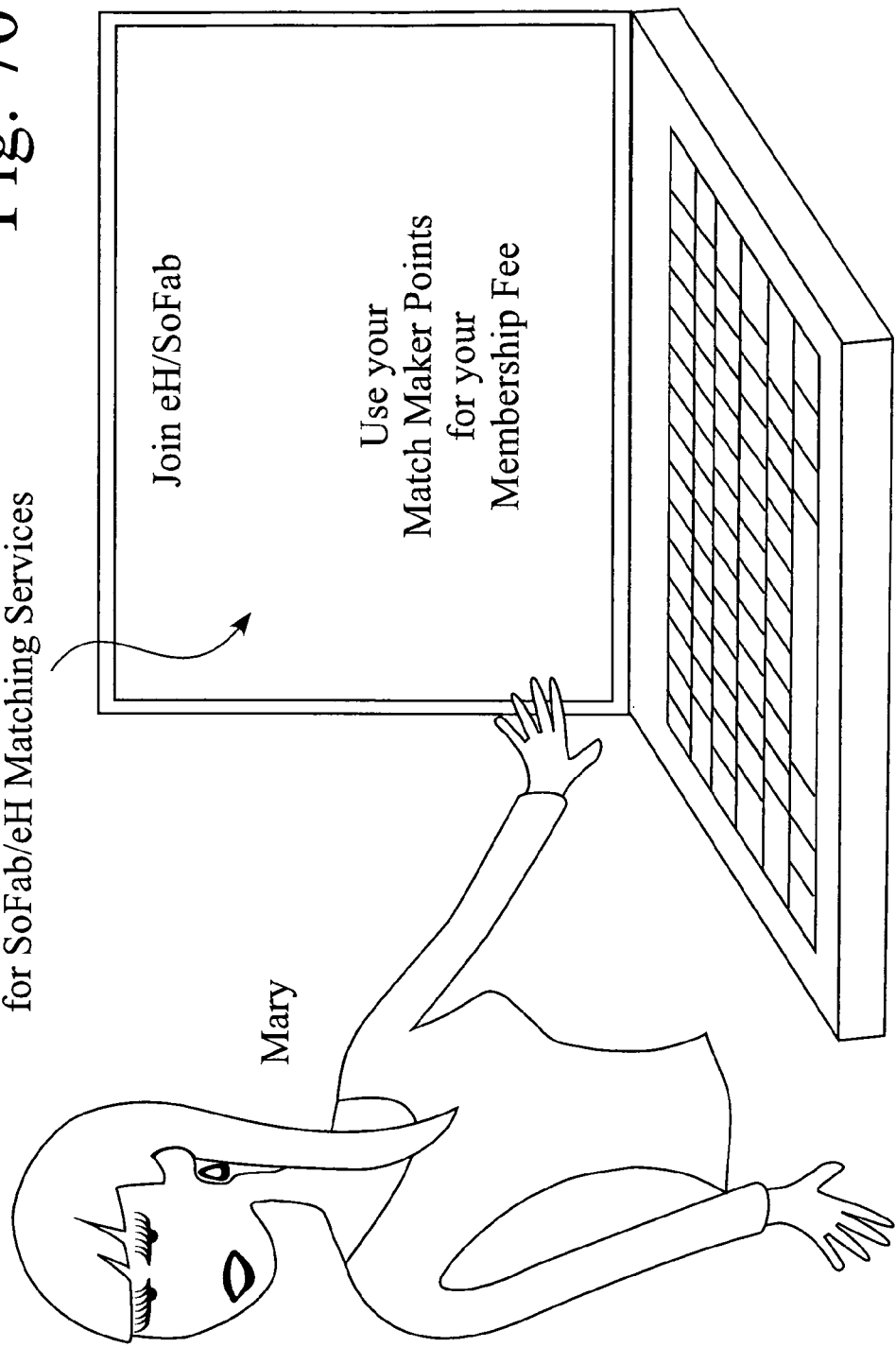

US 8,144,007 B2

1

RELATIONSHIP PREDICTION SYSTEM USING EXTERNAL DATABASES

CROSS-REFERENCE TO RELATED PENDING PATENT APPLICATIONS, CLAIMS FOR PRIORITY & INCORPORATION BY REFERENCE

The Present Application is a Continuation-in-Part Application, and is related to the following Patent Applications:
U.S. Ser. No. 11/239,603, which was filed on 28 Sep. 2005 now U.S. Pat. No. 7,969,301;
U.S. Ser. No. 11/286,143, which was filed on 23 Nov. 2005 now abandoned;
U.S. Ser. No. 11/360,025, which was filed on 21 Feb. 2006 now abandoned;
U.S. Ser. No. 11/405,001, which was filed on 14 Apr. 2006 now abandoned;
U.S. Ser. No. 11/514,285, which was filed on 30 Aug. 2006 now U.S. Pat. No. 7,592,910;
U.S. Ser. No. 11/881,153, which was filed on 24 Jul. 2007 now abandoned;
U.S. Ser. No. 12/290,877, which was filed on Nov. 3, 2008;
U.S. Ser. No. 12/313,263, which was filed on 17 Nov. 2008;
U.S. Ser. No. 12/590,433, which was filed on 5 Nov. 2009 now U.S. Pat. No. 7,940,174;
PCT/GB2006/003581, which was filed on 26 Sep. 2006; and
PCT/GB2007/002836, which was filed on 26 Jul. 2007.

The Applicants claim the benefit of priority in accordance with Sections 119 and/or 120 of Title 35 of the United States Code of Laws for any subject matter which is commonly disclosed in the Pending Patent Applications cited above, and in the Present Application. The contents of all the Patent Applications listed above which have been published are hereby incorporated by reference into the Present Patent Application.

FEDERALLY SPONSORED RESEARCH OR DEVELOPMENT

None.

FIELD OF THE INVENTION

The present invention pertains to the field of predicting good matches for individuals. More particularly, one embodiment of the invention furnishes relationship predictions directly to customers, while another embodiment supplies relationship predictions to a company which offers online dating or other dating or introduction services.

BACKGROUND OF THE INVENTION

I. The Biology of Matching

Mammals have evolved efficient ways to find and select among potential mates. There has been a great deal of research on this subject in the twenty-three years since a landmark study found that mice choose their mates on the basis of their candidates' distinctive odors. Boyse, E. A.; Beauchamp, G. K.; Yamazaki, K; et al., "Chemosensory Communication—A New Aspect of the Major Histocompatibility Complex and Other Genes in the Mouse." Journal: Oncodevelopmental Biology and Medicine. Vol. 4 No. 1-2: Pages 101-116, 1982. These odors are defined by the Major Histocompatibility Complex (MHC). The MHC is a cluster of genes that determines details of cellular surfaces and thus immune responses, and specifies certain peptides that appear in skin secretions and urine. These peptides are responsible for odors which uniquely identify individuals who are not identical twins.

More recent work has shown that human female sexual responsivity to a male partner varies linearly and inversely with the degree to which genes in the Major Histocompatibility Complex are shared. Garver-Apgar, Christine E. et al., "MHC Alleles, Sexual Responsivity, and Unfaithfulness in Romantic Couples," Psychological Science, Volume 17, Number 10, (October 2006). The correspondence is dramatic: about a nine (on a self-reported scale of one to ten) in responsivity to men who share none of a woman's MHC genes and to those who share sixty percent.

Men and women detect others' MHC genes through their body odors. There are a number of peptides that are derived from particular regions of the MHC. These peptides are detected as odors. They strongly affect a woman's responsivity to a particular partner, as discussed in the cited literature, and to both men's and women's mutual attractiveness.

This mate-selection process has a strong effect on the fitness of offspring. Choosing mates on the basis of MHC dissimilarity equips offspring with a broad immune system, increasing the offspring's fitness, and also reduces the rate of spontaneous abortion. It also selects against close relatives as mates, increasing the viability of fetuses and reducing birth defects. It also reduces the rate of spontaneous abortion: there is compelling evidence that fetuses of couples which share significant numbers of MHC alleles are more likely to be rejected in utero. Komlos, L., Zamir, R., Joshua, H., and Halbrecht, I., "Common HLA Antigens in Couples with Repeated Abortions," Clinical Immunology and Immunopathology 7, Pages 330-335 (1977).

Other studies, including one cited above, have shown that women who are in long-term intimate relationships with men with similar MHC alleles are more likely to report being attracted to and fantasizing about other partners during the fertile portion of their menstrual cycles. This practice obviously has a destabilizing effect on these relationships, which include marriages. Because humans' sense of smell is relatively poor, couples who are strangers must come into close personal contact before they can estimate their MHC-derived "fit" with a potential male partner and thus a woman's long-term sexual responsivity to her partner. As humans have moved from villages to cities, various means have been created to bring men and women of marriageable age into close proximity under controlled conditions: examples range from the masked ball in Romeo and Juliet to modern on-line dating services. In modern human society, with much less class structure and much more freedom for men and women than in tribal, medieval or Victorian eras, and a much higher probability of encountering strangers than in primitive (pre-tribal) eras, this acquaintance process can pose considerable danger and risk of embarrassment to women. The modern process of selecting a mate is very inefficient compared to these earlier societies, in which the number of potential partners available to each woman was comparatively small, and in primitive societies where people lived in very close proximity. It would be of great benefit, not only to individual couples, but to society as a whole, if men and women could assess their sexual compatibility and the health of any offspring of the union without coming into close contact. This would, among other things, give women a wider range of prequalified candidates and would give men greater assurance that they and their prospective mates would have a stable and persistent relationship characterized by mutual physical attraction. It is generally conceded that mutual sexual attraction and responsivity are major contributors to pair bonding: they are the glue that holds long-term relationships together. People of all political and religious persuasions agree that stable pair-bonding, carrying the benefit of reduced strife and relationship discord, is in the best interest of society. Strife and relationship discord result in failed marriages and in infidelity. Society as a whole will thus benefit from easier and more accurate responsivity assessment. It is also important to note that there remain many cultures in which arranged marriages are the norm, and in which affianced couples do not meet before their wedding ceremony. Parents and matchmakers who are concerned with the success of their efforts could gain confidence from an MHC-based genetic matching process before a commitment is made.

Technology has advanced to the point that individual MHC-derived peptides, and thus odors, can be accurately detected artificially using gas chromatography and/or mass spectrometry (an "e-nose"). Willse, Alan et al., "Identification of Major Histocompatibility Complex-Regulated Body Odorants by Statistical Analysis of a Comparative Gas Chromatography/Mass Spectrometry Experiment," Analytical Chemistry, Vol. 77, No. 8 (Apr. 15, 2005). This implies that a personal odor profile can be constructed for each individual, and that the degree of MHC-allele sharing of two individuals can be derived by comparing those measurements, even if they are strangers and geographically distant from one another. MHC analysis can also be done on the basis of other material, such as cheek-cell scrapings, saliva tests, and other means used in forensic settings.

This process represents a considerable improvement to acquaintance-facilitation ("dating") services based on the use of questionnaires and personality profiling. While these services help people find partners based on their subjective preferences and personality match, they say little about the likelihood of sexual attraction on first meeting, or the sexual responsivity of the partners in a long-term relationship. In contrast to these methods, MHC comparison is a completely objective process. Unlike current processes which rely on self-administered questionnaires, remote psychological assessments and other user-supplied personal data, MHC comparison cannot misrepresent its user.

II. The Current Market for Matching Services & the Need for Improvement

According to Jupiter Research, online personals revenues will have risen from about four hundred million dollars in 2003, to over six hundred million dollars in 2009. In the United States alone, over seventeen million persons participate in online dating each year (Nielsen Media Research). In 2008, revenue from online dating services will exceed revenue from dating services and personal ads which appear in conventional media (Marketdata Enterprises, Inc.).

Despite this dramatic growth in the online dating industry, many individuals who have used online dating services remain disappointed with their results. The development of a system that provides a tool for predicting good matches based upon applied biological and genetic mechanisms of attraction would fulfill a long felt need in the dating and relationship industry, and would constitute a great benefit to members of society.

SUMMARY OF THE INVENTION

The present invention comprises methods and apparatus for providing a relationship prediction based on the correlation of personal characteristics and the analysis of genetic characteristics. In one embodiment, a first person supplies descriptions of his or her own personal characteristics, as well as descriptions of the personal characteristics of her or his ideal match, to a website; or by other means to a dating or introduction service provider. The first person also furnishes an odor, tissue or fluid sample to a test facility, where genetic characteristics, are analyzed and determined. A relationship match is then generated based on both a combination of both a positive correlation of the personal characteristics of the first person and second person, and a measured dissimilarity between the sequence of genetic characteristics of the first person and second person. In one embodiment, relationship matches are provided directly to customers. In an alternative embodiment, relationship matches are provided to a company which offers online dating or other dating or introduction services. In another embodiment of the invention, a match is computed for a woman based upon her responsivity to a man, which is based upon the extent of dissimilarity of their MHC-alleles; and a correlation of the attributes and preferences of that woman and that man.

In yet another embodiment, the customer may purchase a custom-formulated perfume, cologne, salve or other cosmetic or preparation that contains enhanced aromas that match his or her, or his or her partner's, genetic attributes.

In one embodiment of the invention, personal characteristics or interests are obtained from an external database or webpage, and are then used to assist in the process of suggesting a good match.

An appreciation of the other aims and objectives of the present invention, and a more complete and comprehensive understanding of this invention, may be obtained by studying the following description of preferred and alternative embodiments, and by referring to the accompanying drawings.

A BRIEF DESCRIPTION OF THE DRAWINGS

Figure 9:
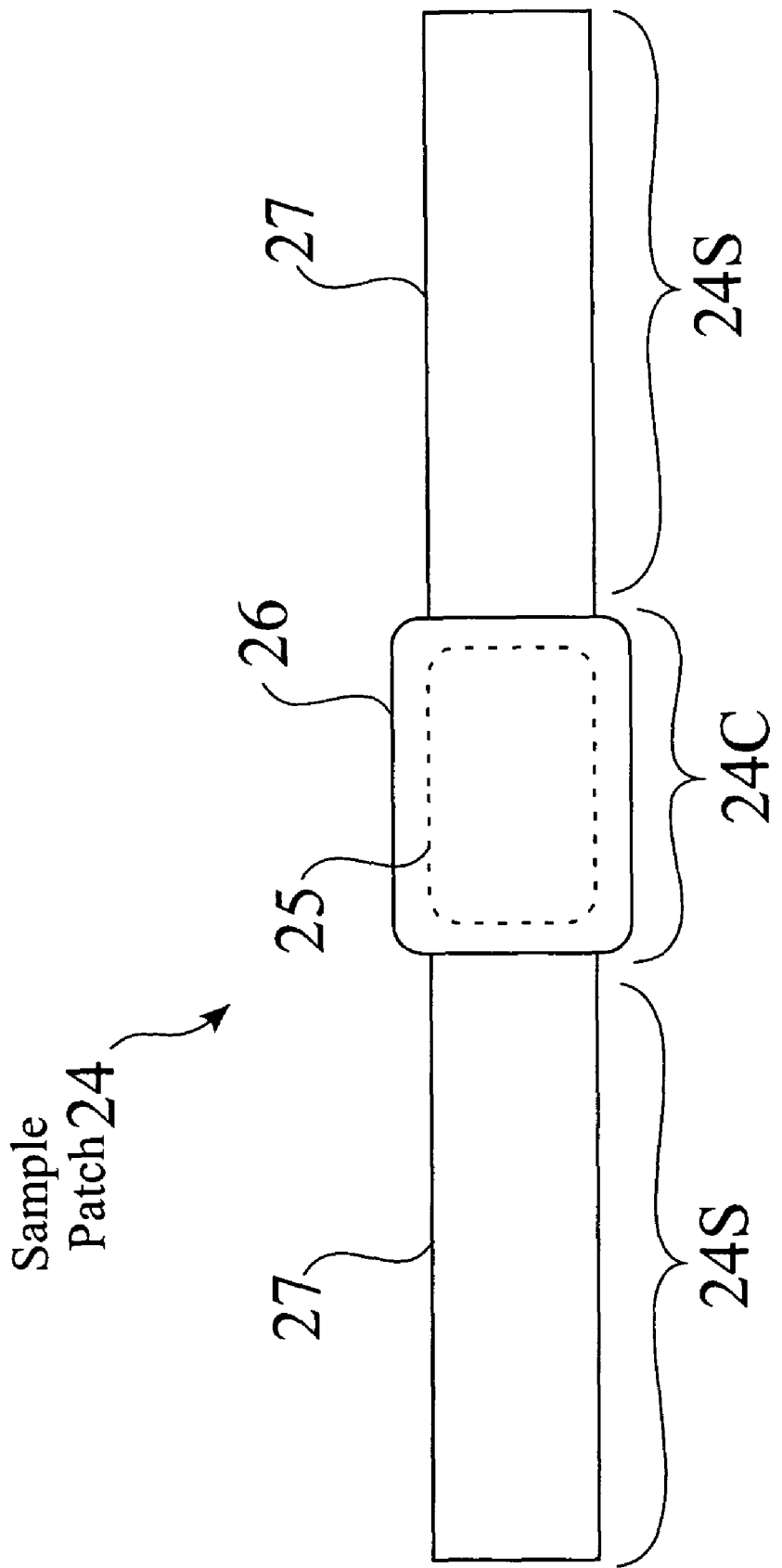

FIG. 9 supplies a detailed view of the sample patch.

Figure 10:
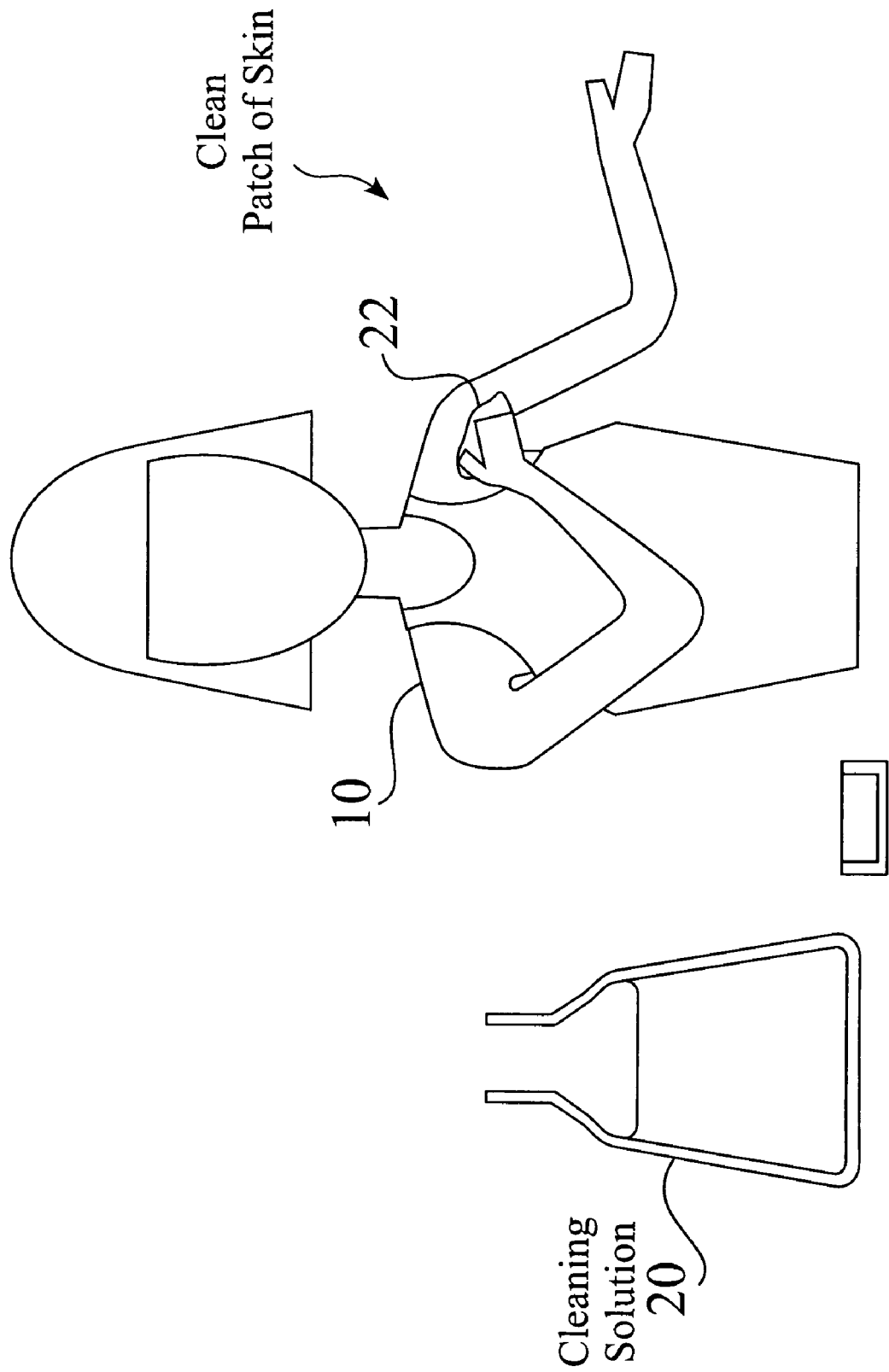

In FIG. 10, the woman cleans a patch of skin in preparation for applying the sample patch to her armpit.

Figure 11:
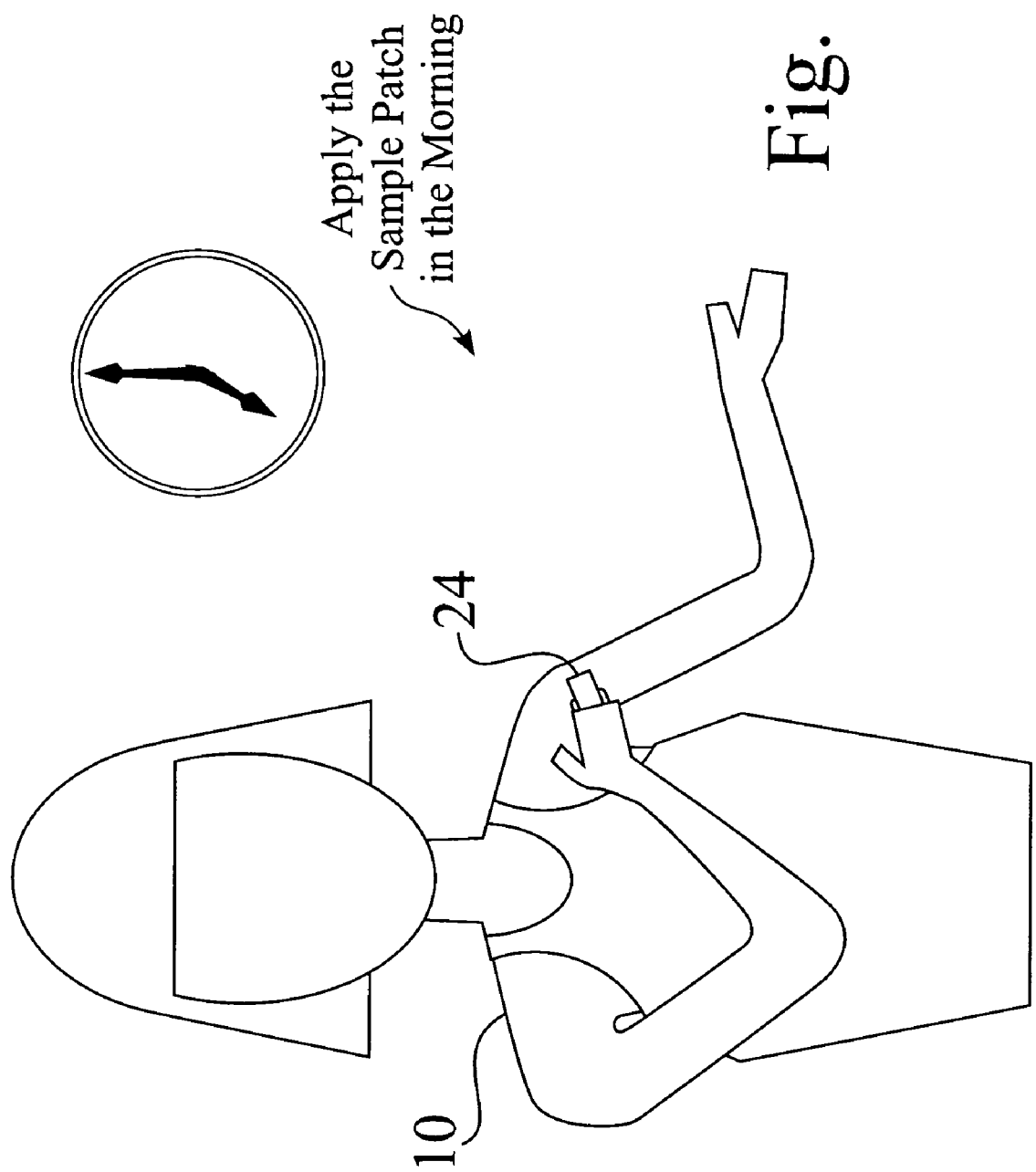

In FIG. 11, the woman applies the patch to her armpit.

Figure 12:
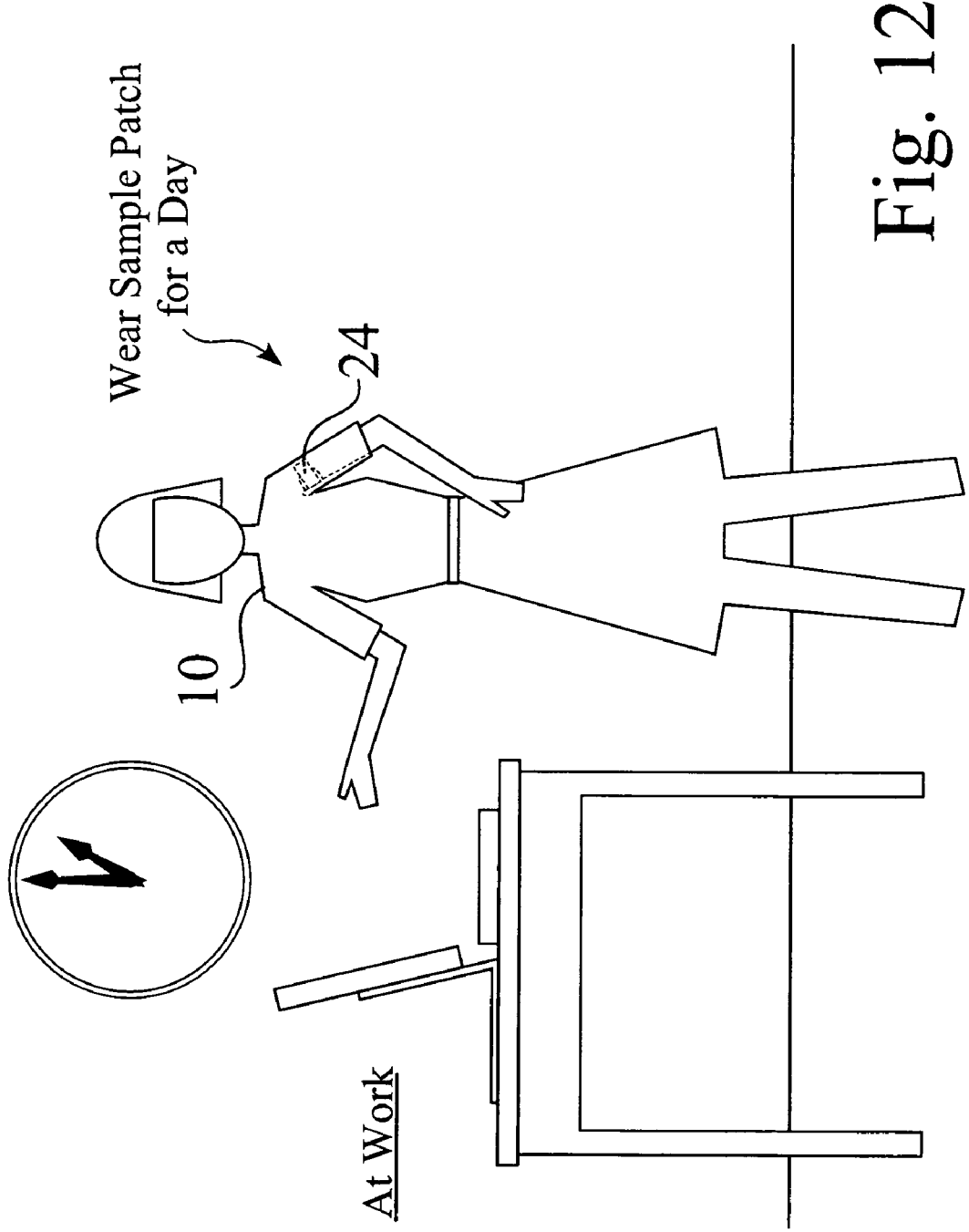

FIG. 12 shows the woman wearing the patch for a day or longer.

Figure 13:
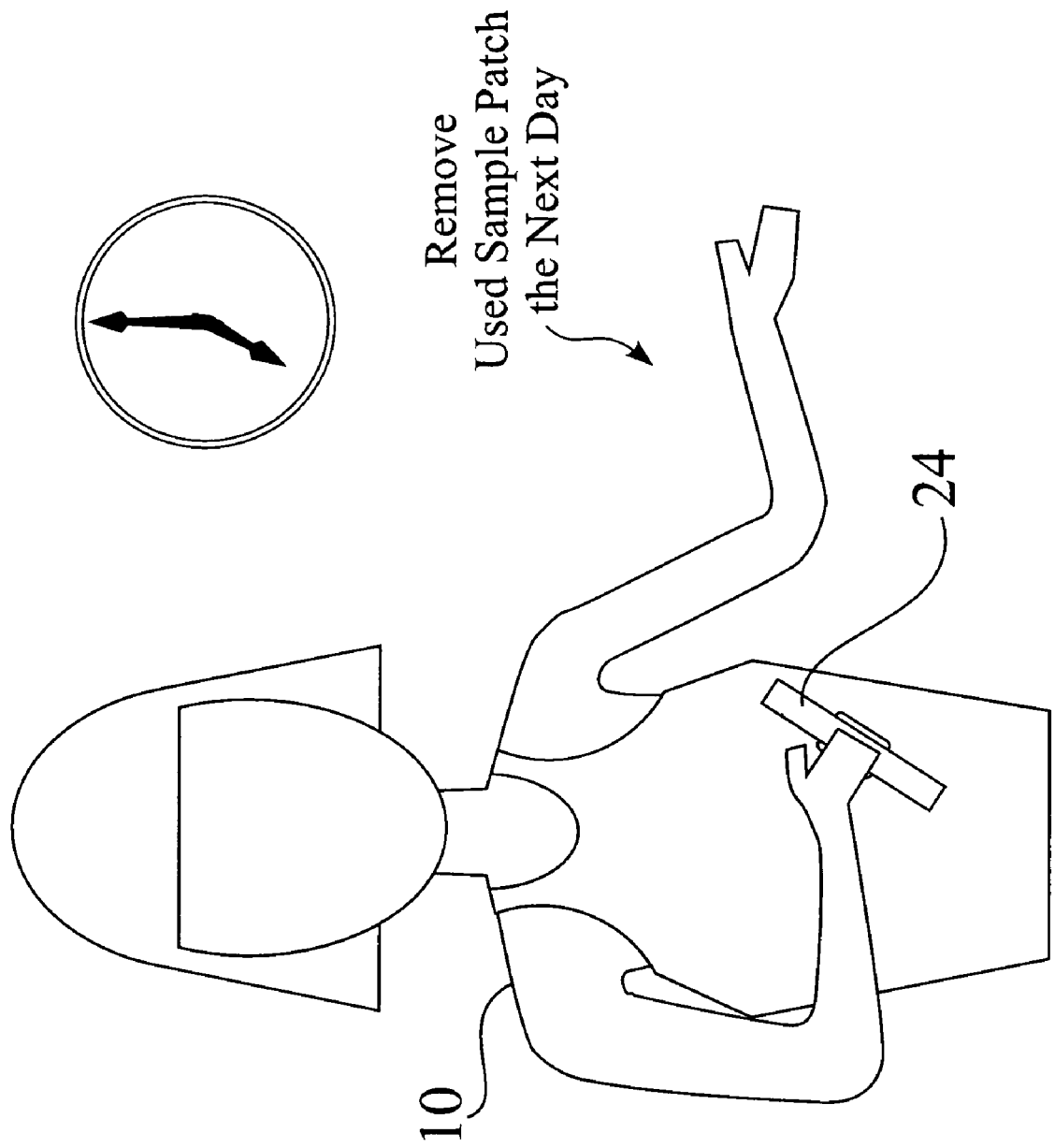

FIG. 13 portrays the woman removing the sample patch from her arm on the next day.

Figure 14:
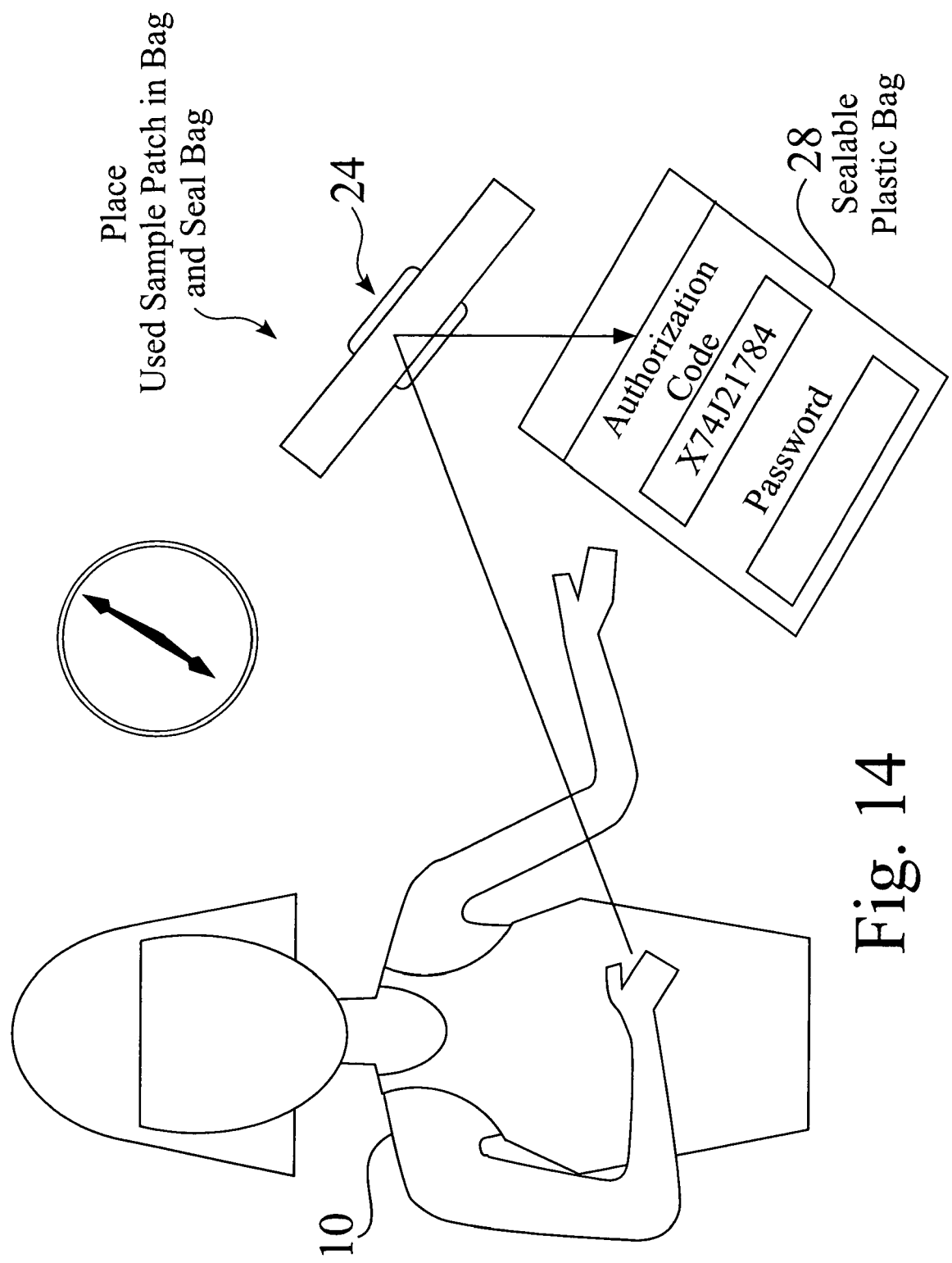

In FIG. 14, the woman places the sample patch that she has worn for a day into the bag, and seals it.

Figure 15:
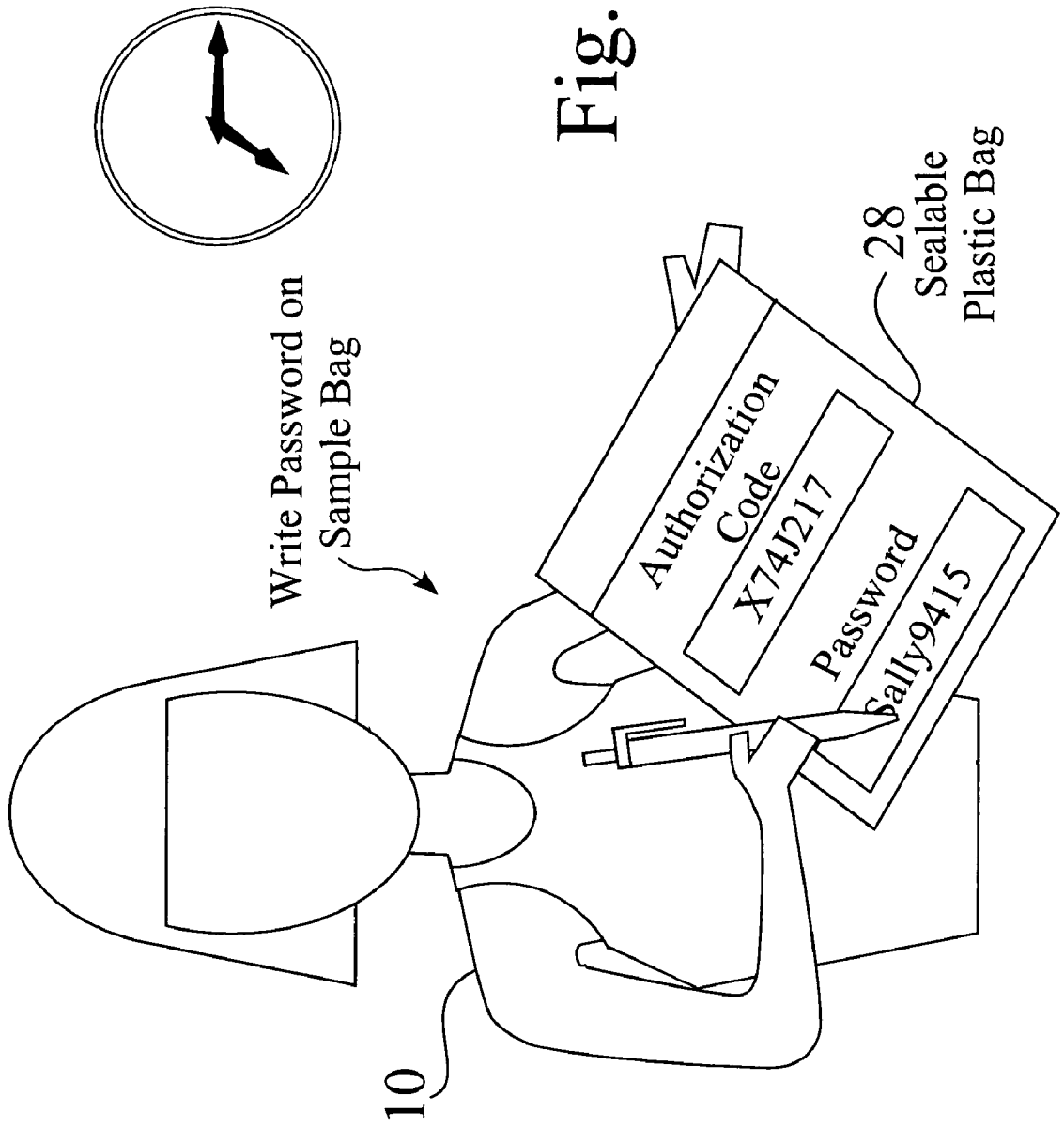

In FIG. 15, the woman writes her password on the sealable bag.

Figure 16:
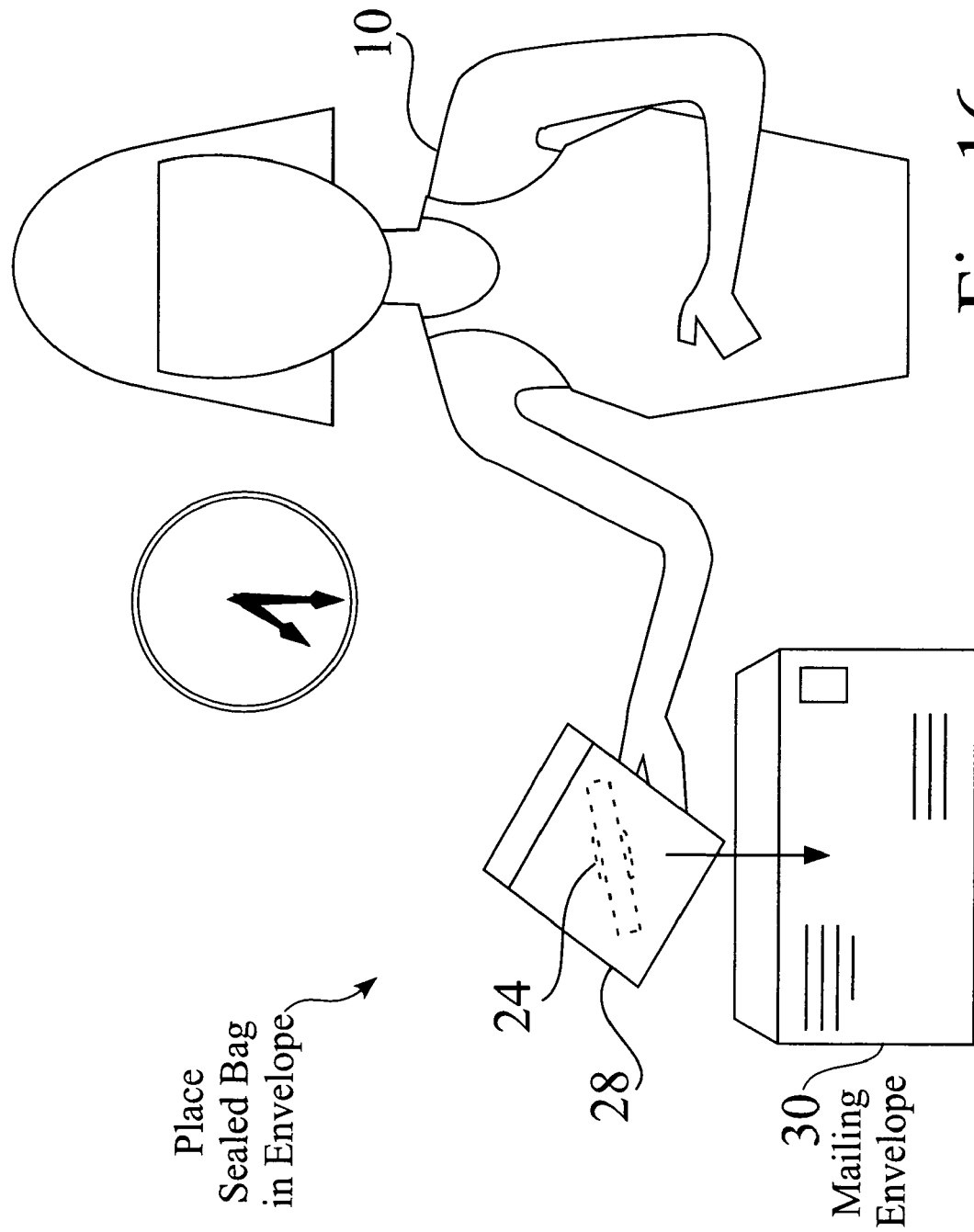

In FIG. 16, the sample that has been sealed in the bag is placed in a mailing envelope.

Figure 17:
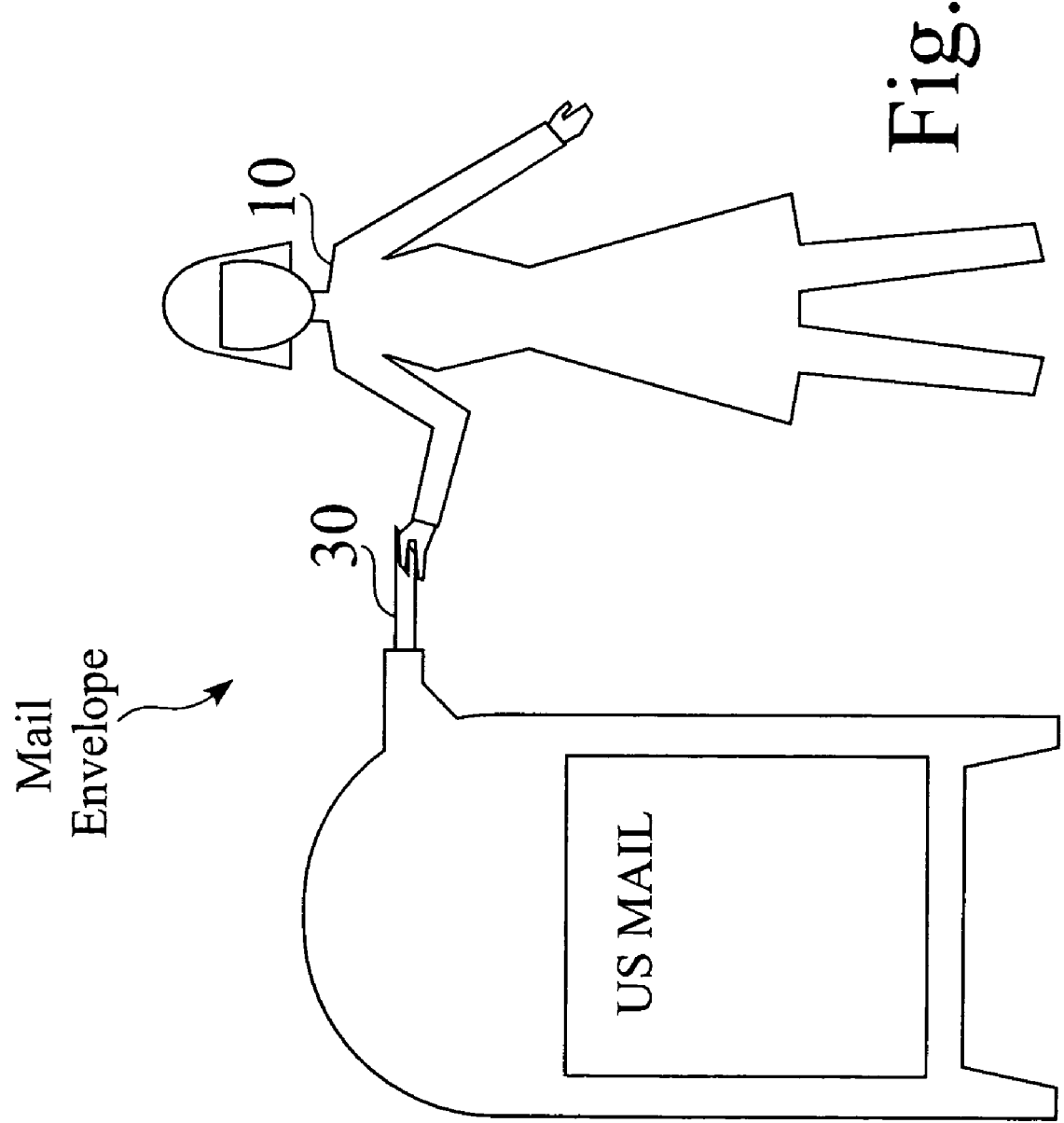

FIG. 17 shows the woman mailing an envelope which contains the bag, which, in turn, contains the worn sample patch.

Figure 18:
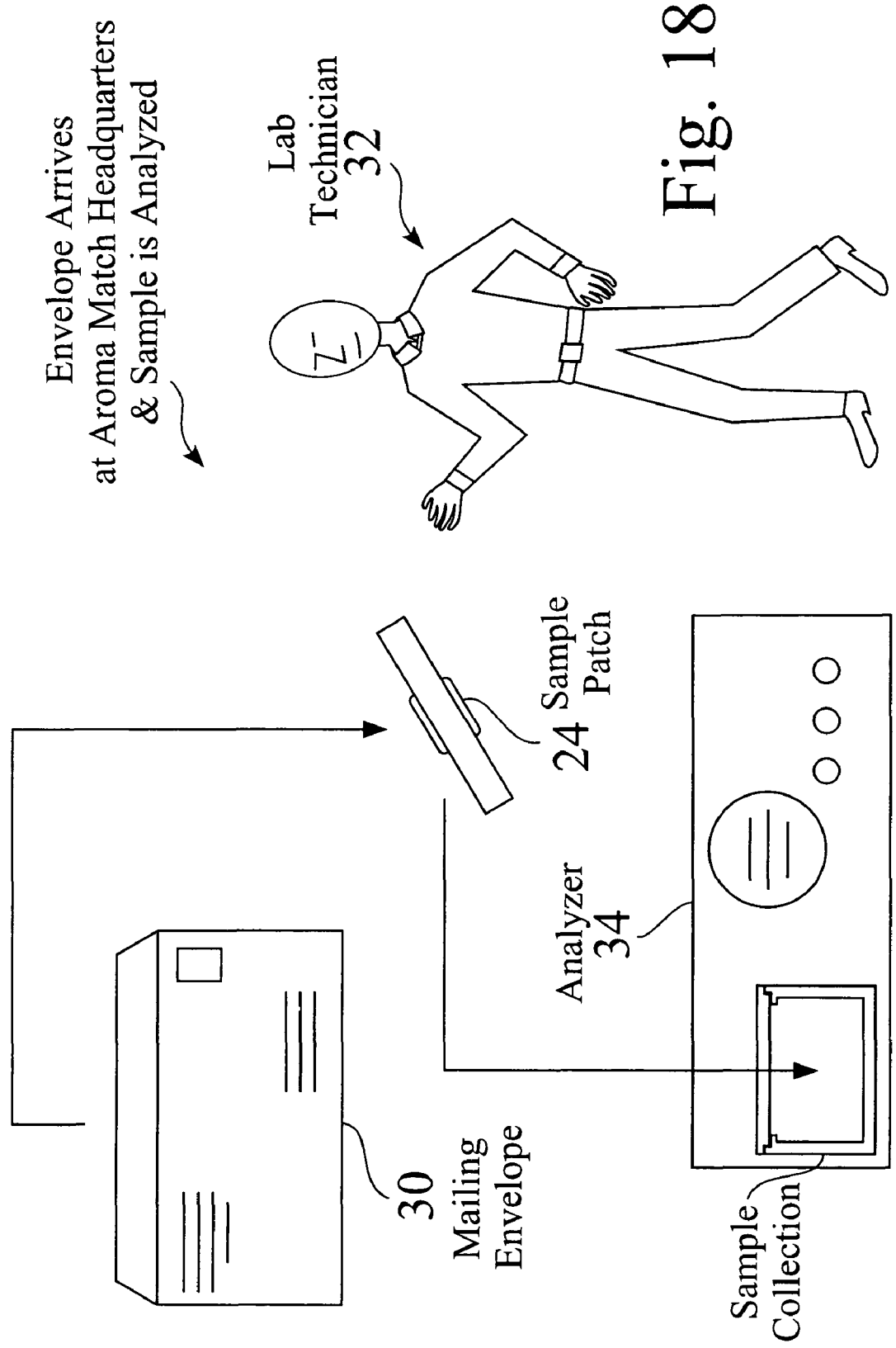

FIG. 18 shows a laboratory technician using an analyzer to determine the genetic attributes of the odor sample that has been received from the woman depicted in FIG. 17.

Figure 19:
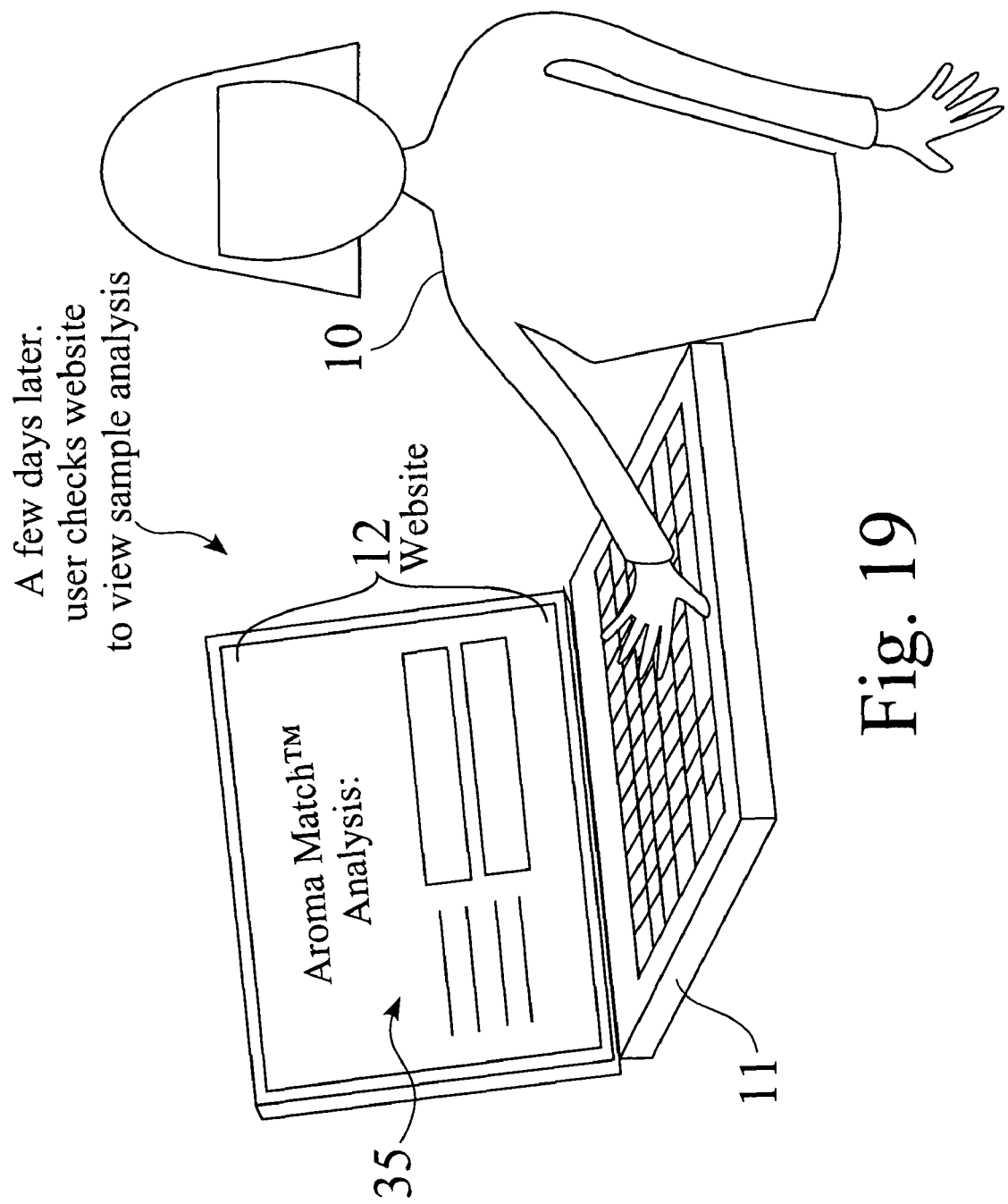

In FIG. 19, the woman uses her computer to visit a website to obtain the results of the laboratory analysis.

Figure 20:
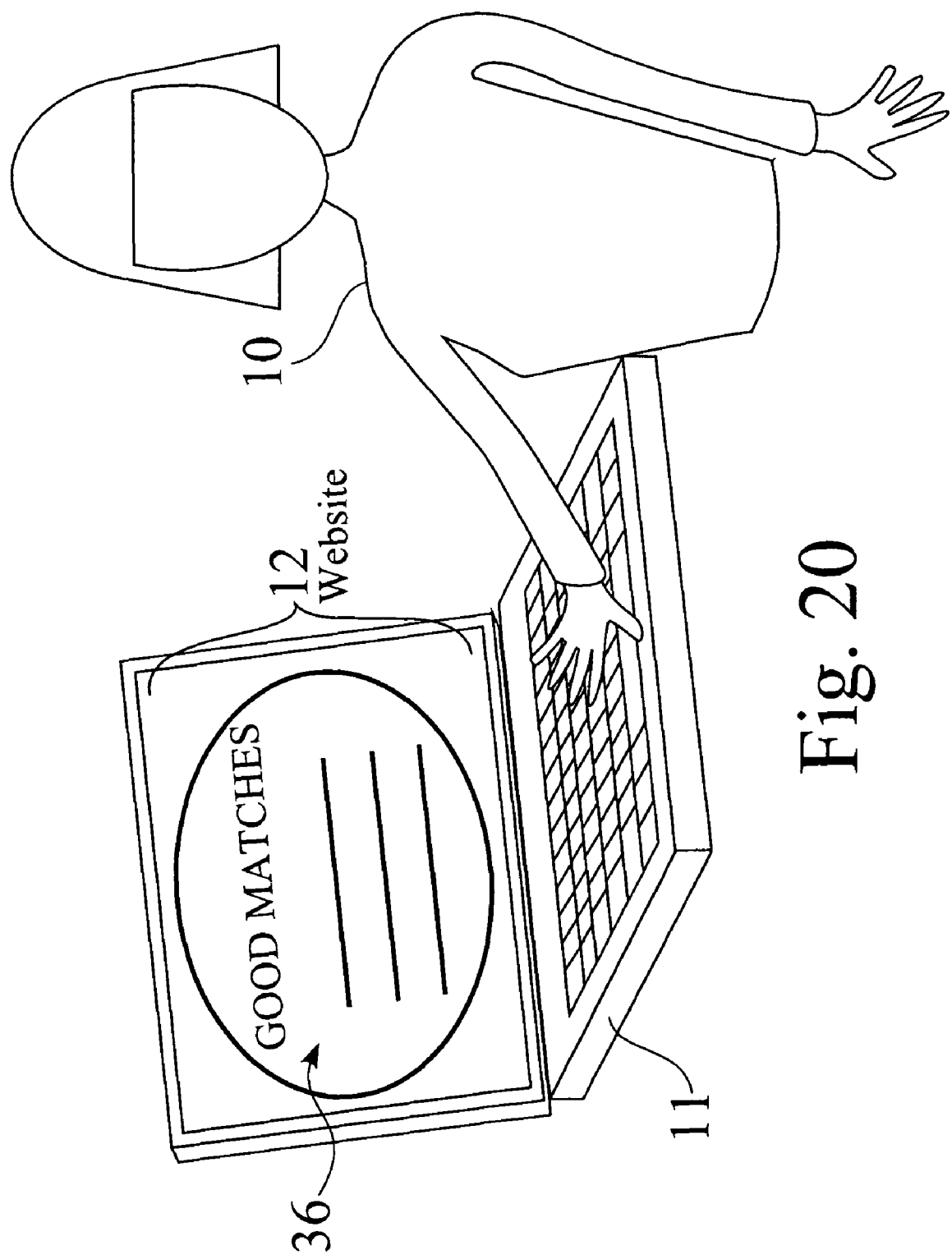

In FIG. 20, the website reports the results of a matching process that has been performed using a library of candidates.

Figure 21:
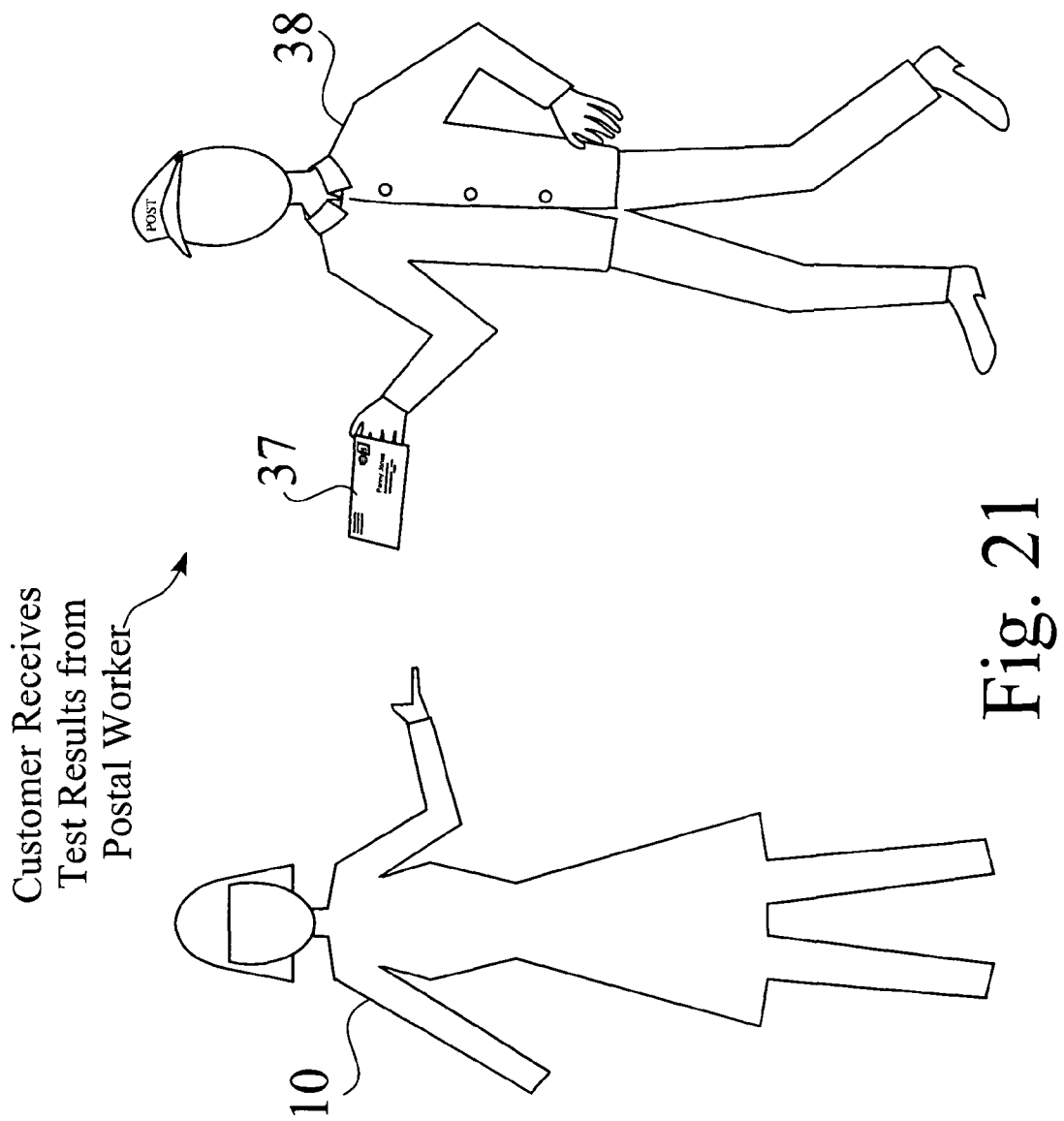

FIG. 21 shows the woman receiving test results from a postal worker.

Figure 22:
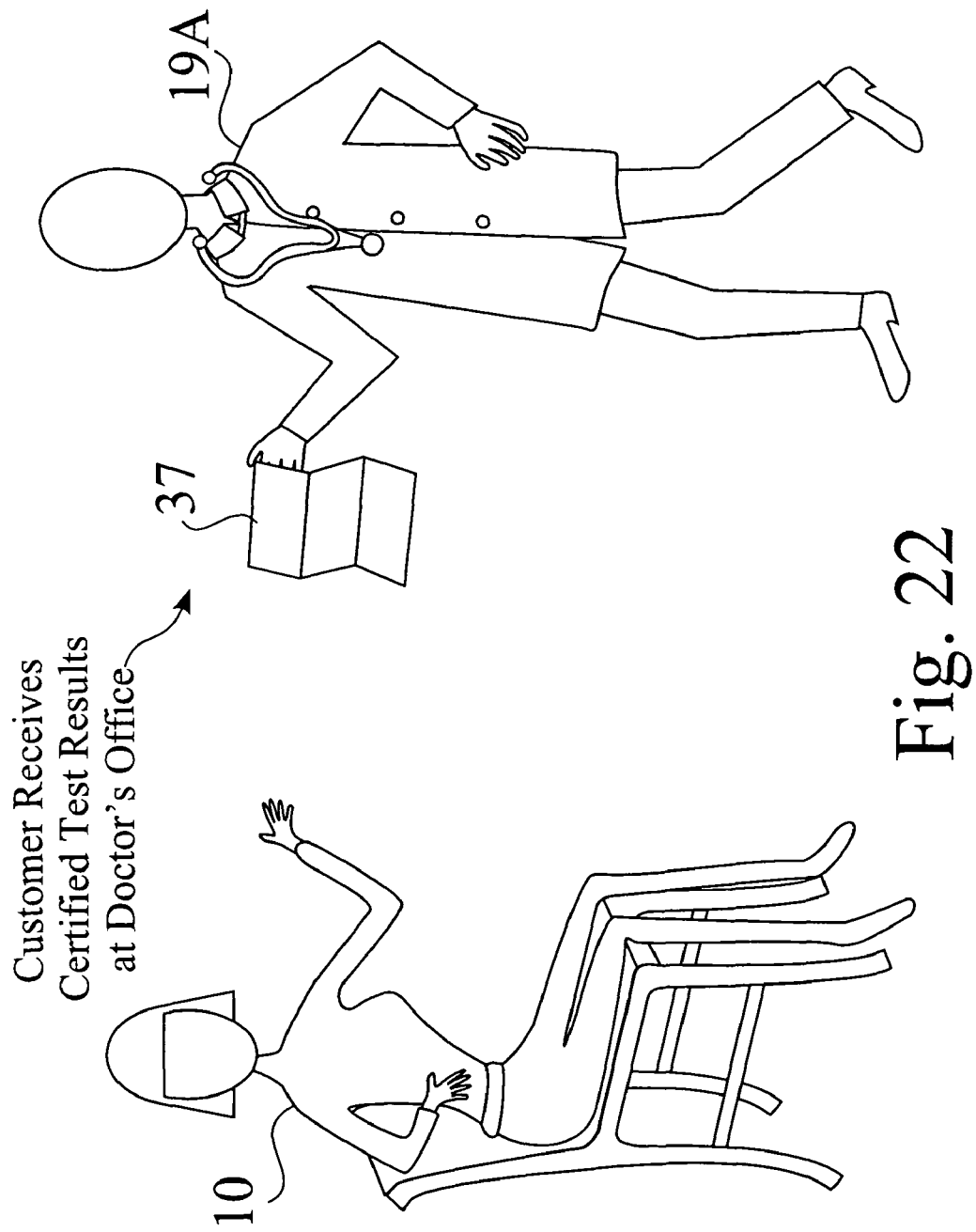

FIG. 22 shows the woman receiving test results from a physician.

Figure 23:
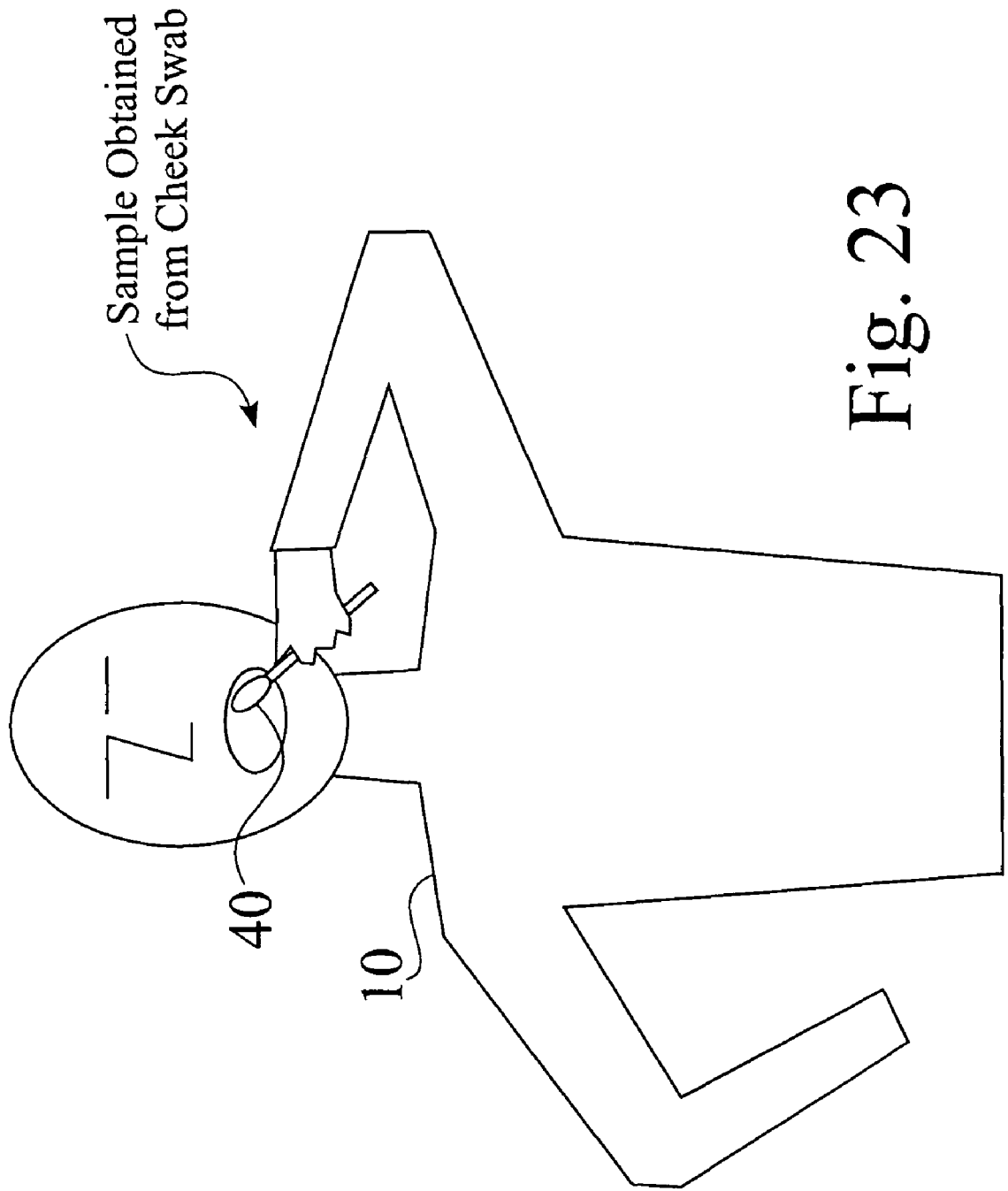

FIG. 23 an alternative embodiment of the invention, in which a tissue sample is obtained using a cheek swab.

Figure 24:
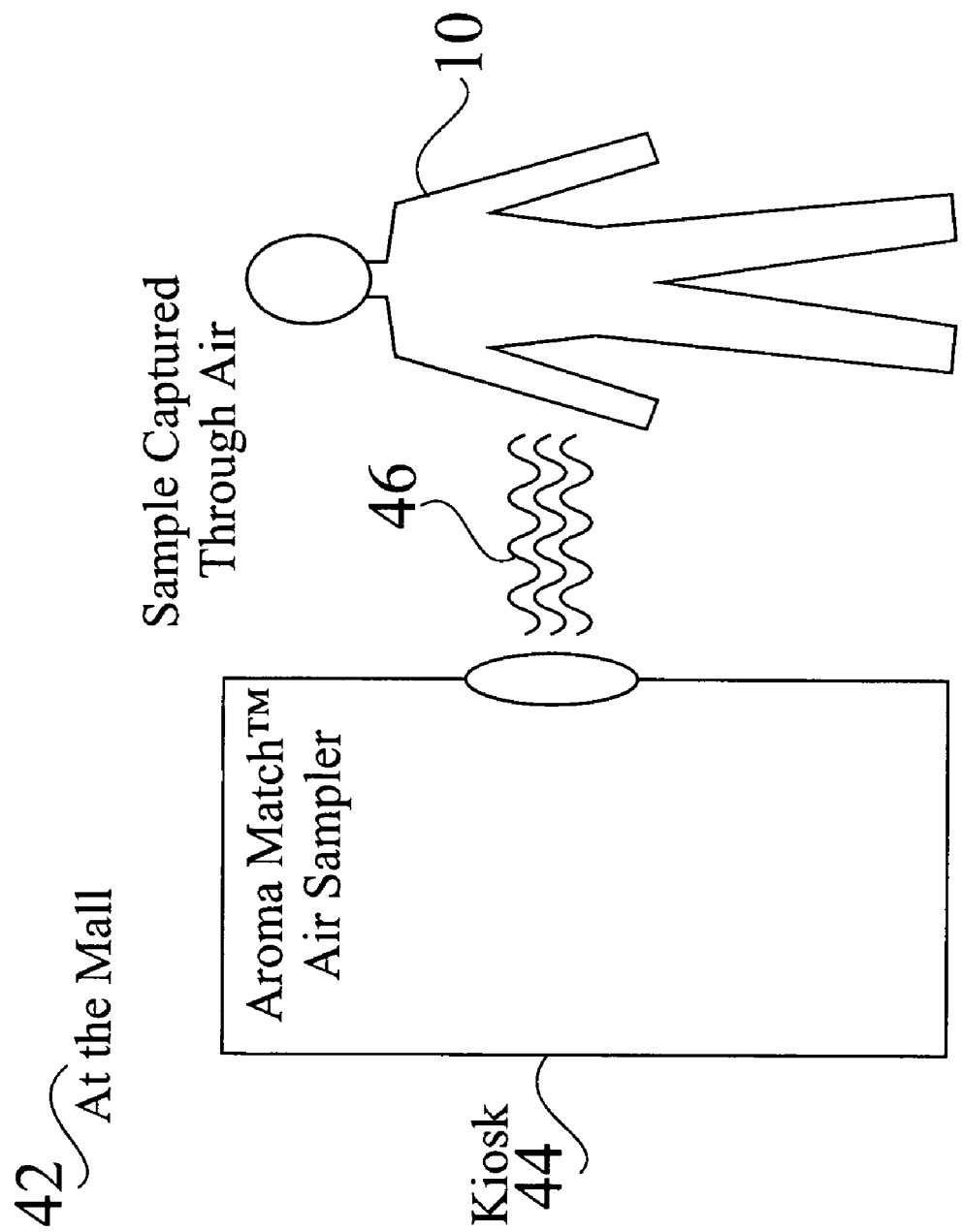

FIG. 24 exhibits yet another alternative embodiment, which collects a sample directly from the air surrounding a man.

Figure 25:
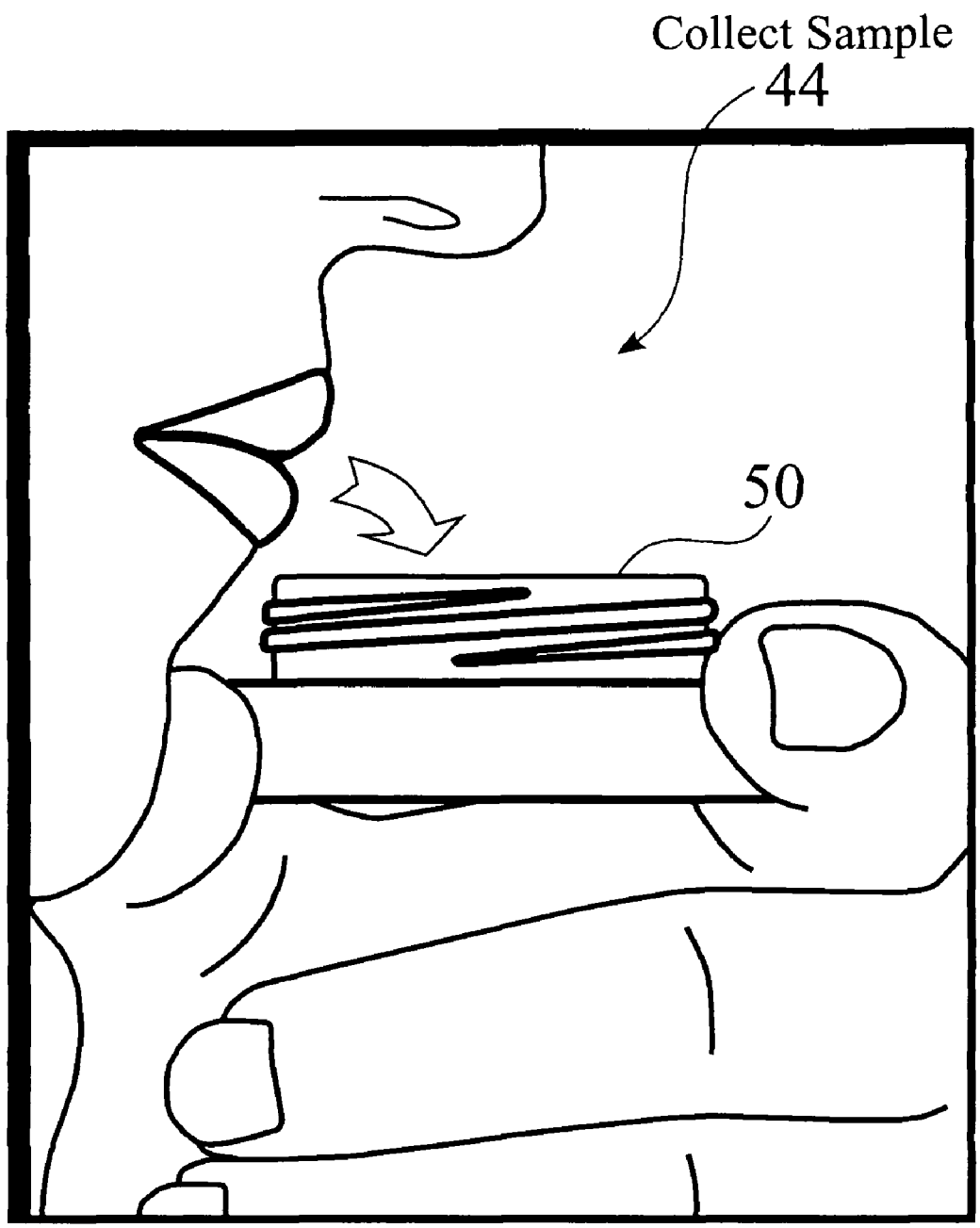

FIG. 25 depicts the collection of a saliva sample in a container.

Figure 26:
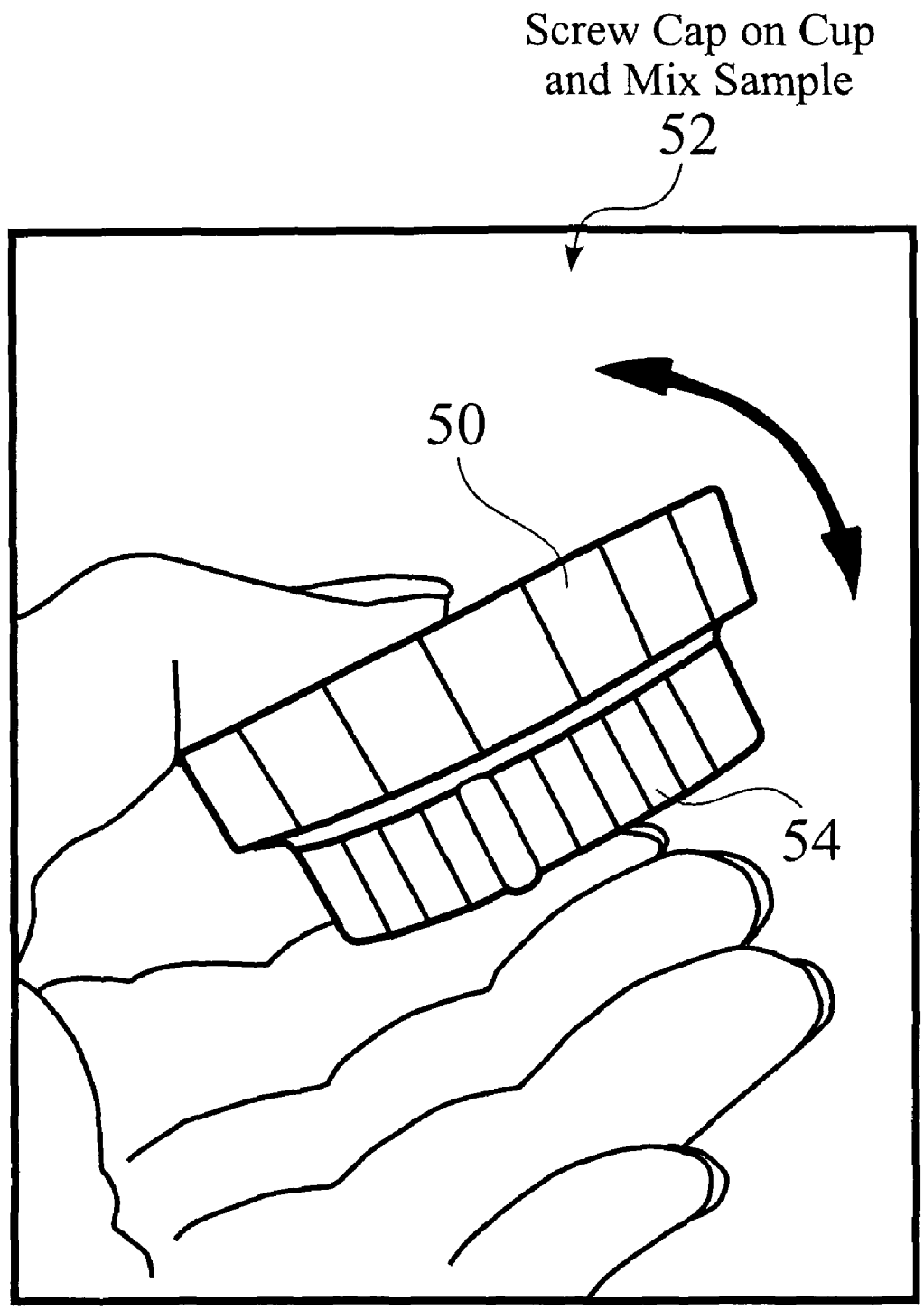

In FIG. 26, the sample saliva is mixed.

Figure 27:
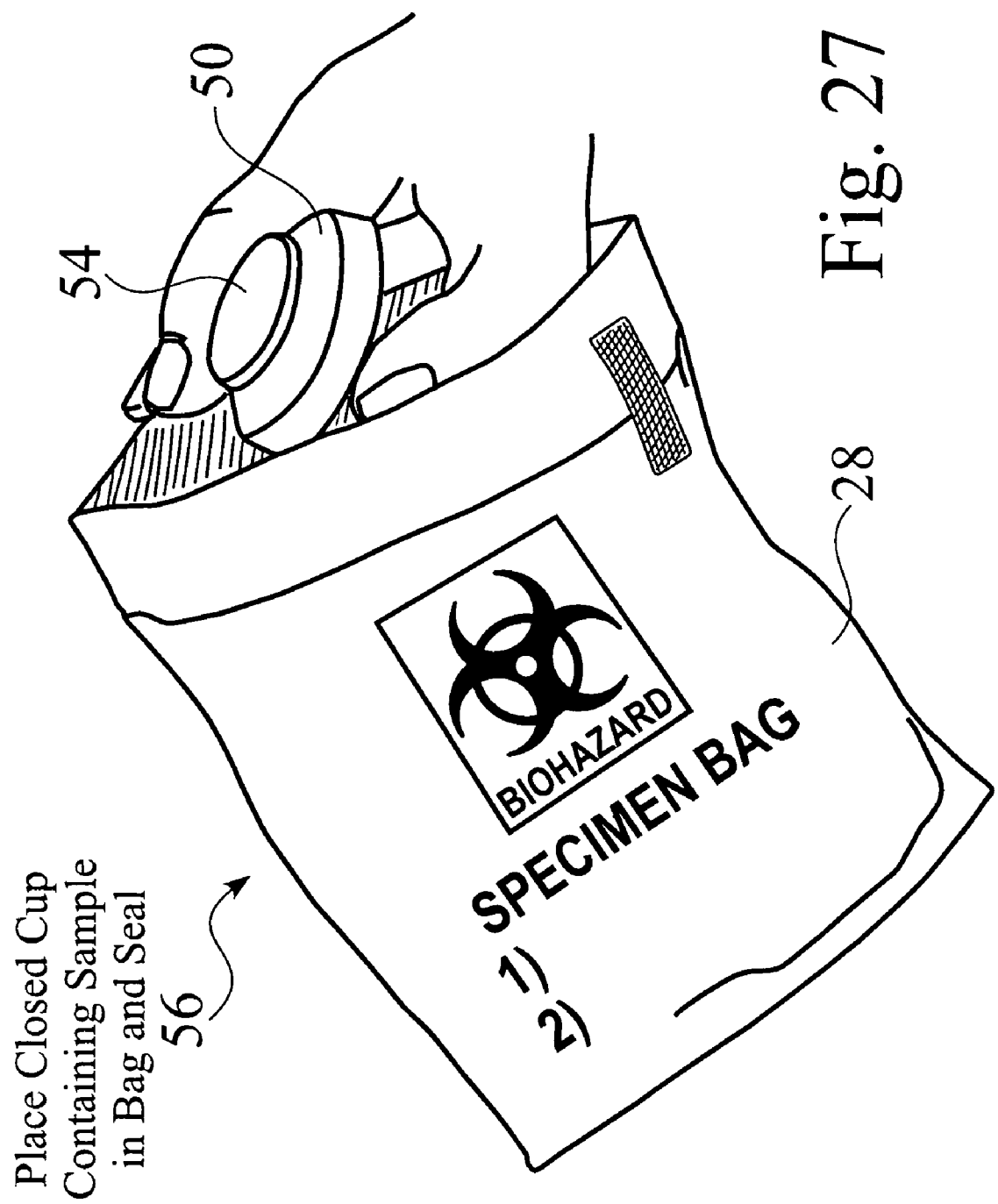

FIG. 27 shows the sample's being placed in a sample bag.

Figure 28:
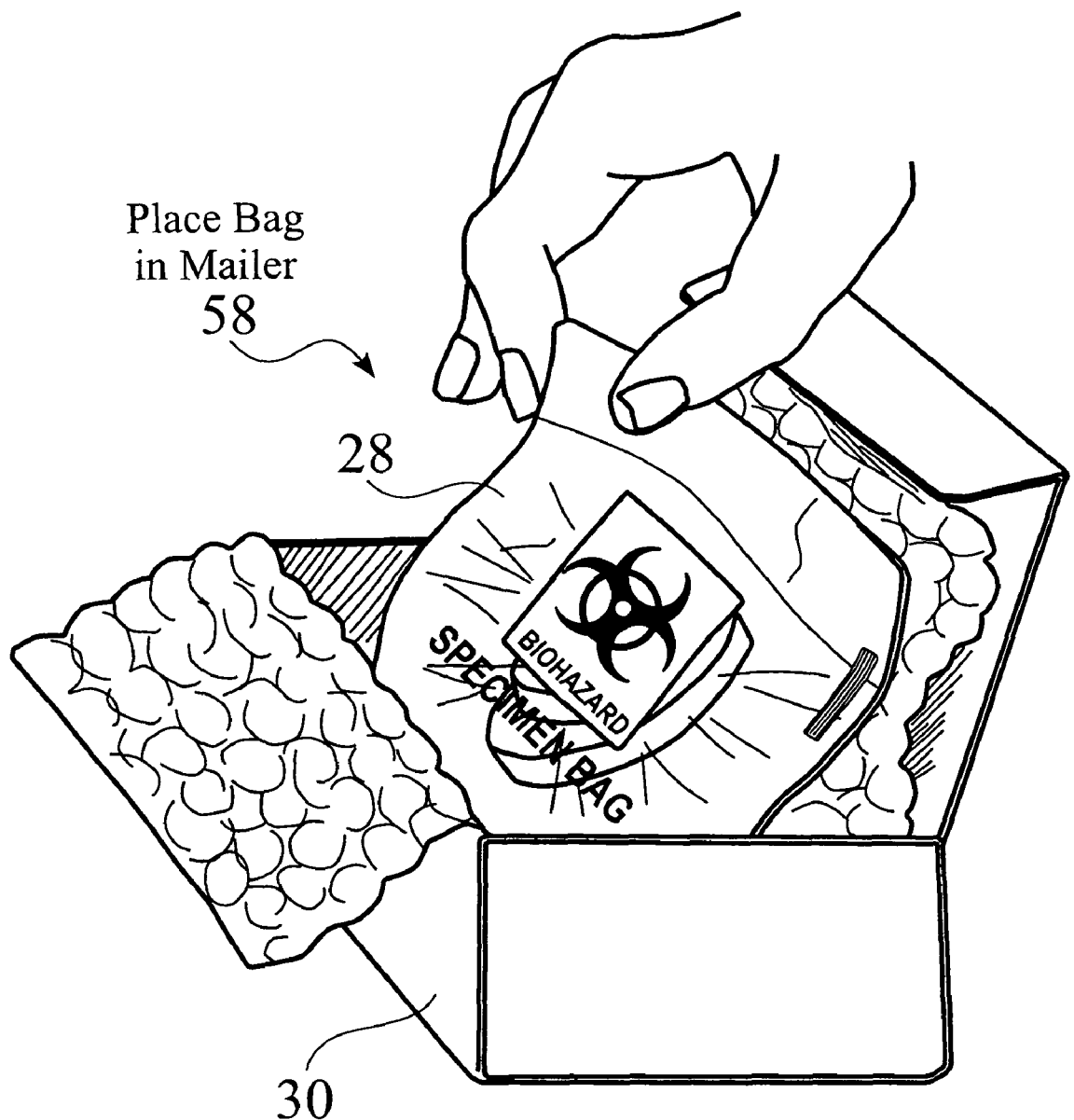

FIG. 28 shows the sample bag's being placed in a mailing box.

Figure 29:
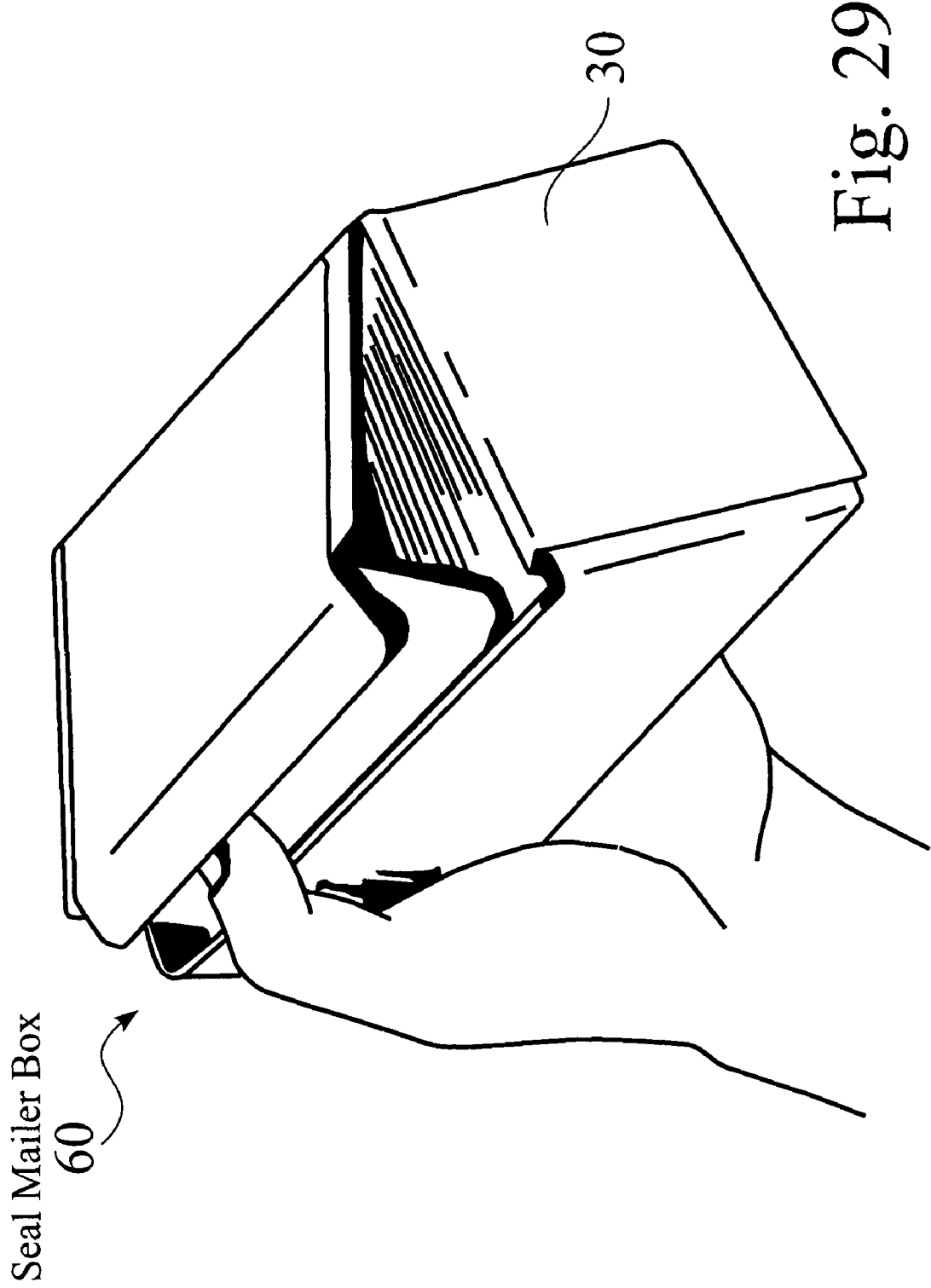

FIG. 29 shows the mailing box's being sealed.

Figure 30:
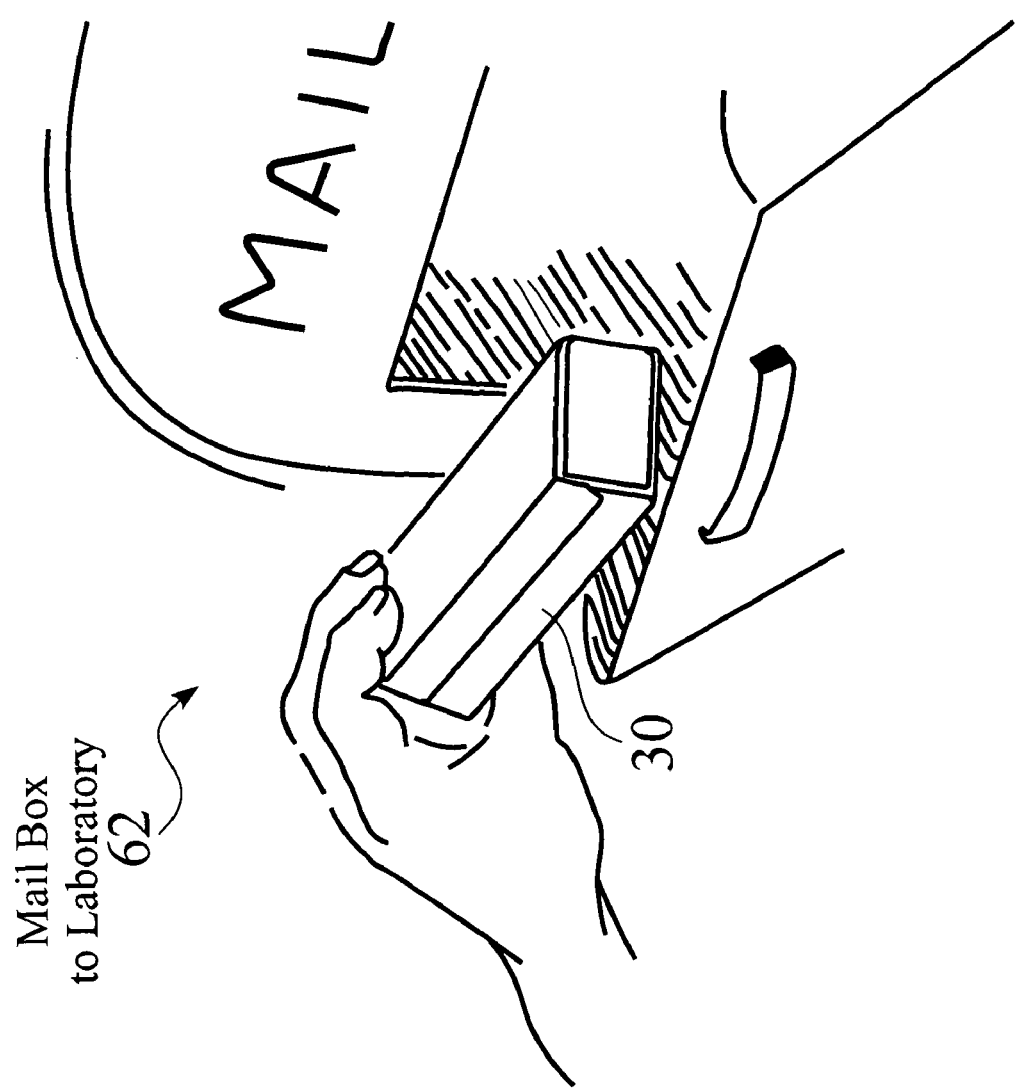

FIG. 30 shows the box's being mailed.

Figure 31:
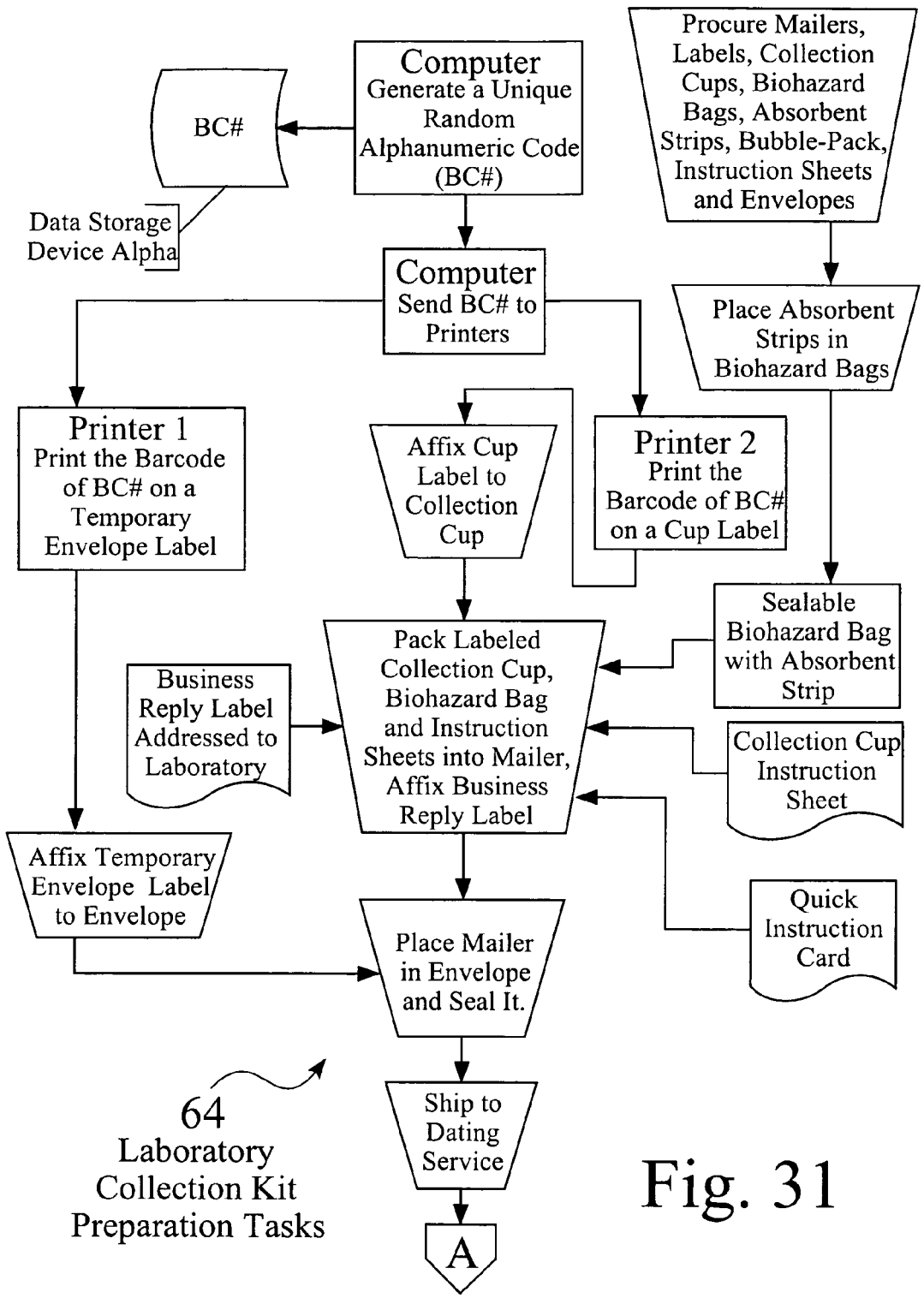

FIG. 31 is a flow chart which illustrates laboratory collection kit preparation tasks.

Figure 32:
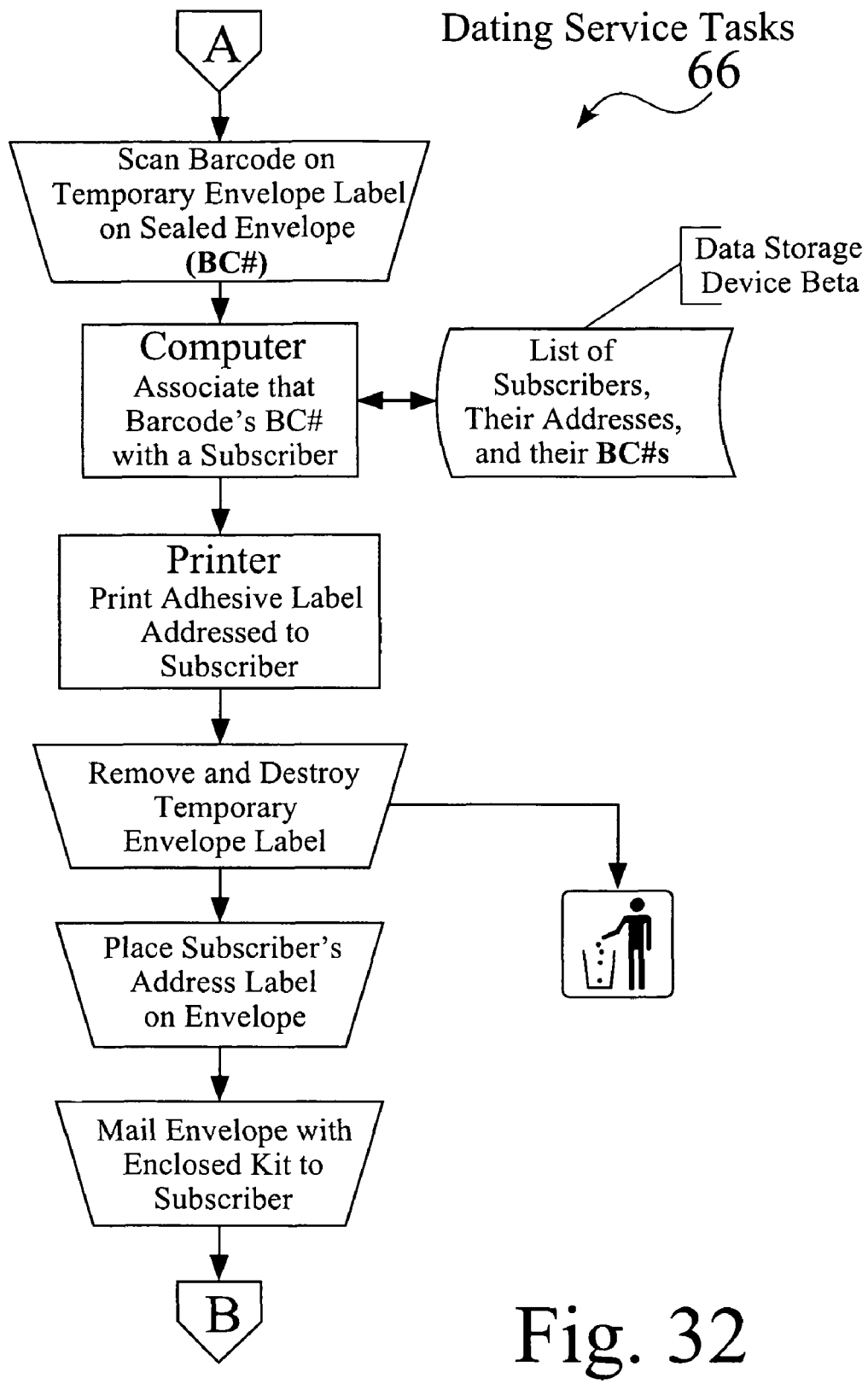

FIG. 32 is a flow chart which illustrates dating service tasks.

Figure 33:
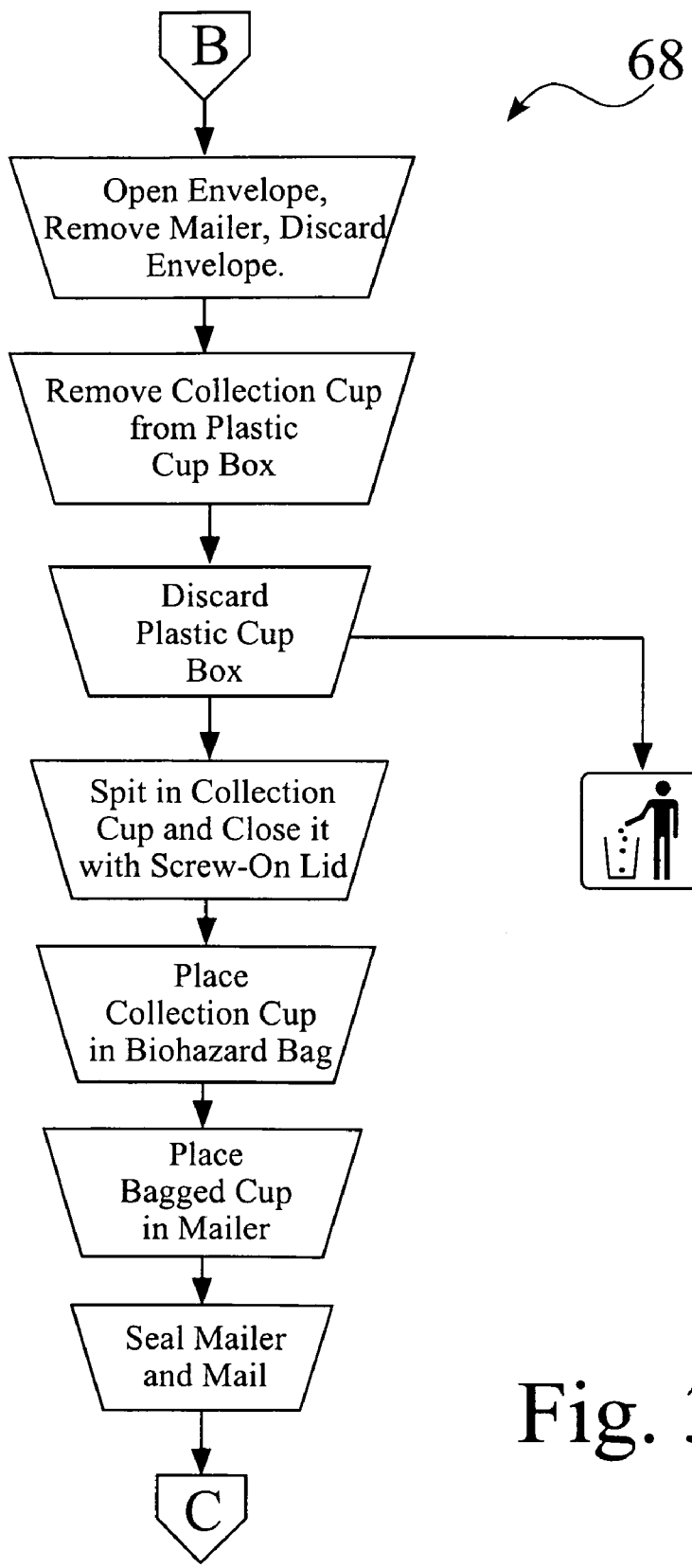

FIG. 33 is a flow chart which illustrates customer tasks.

Figure 34:
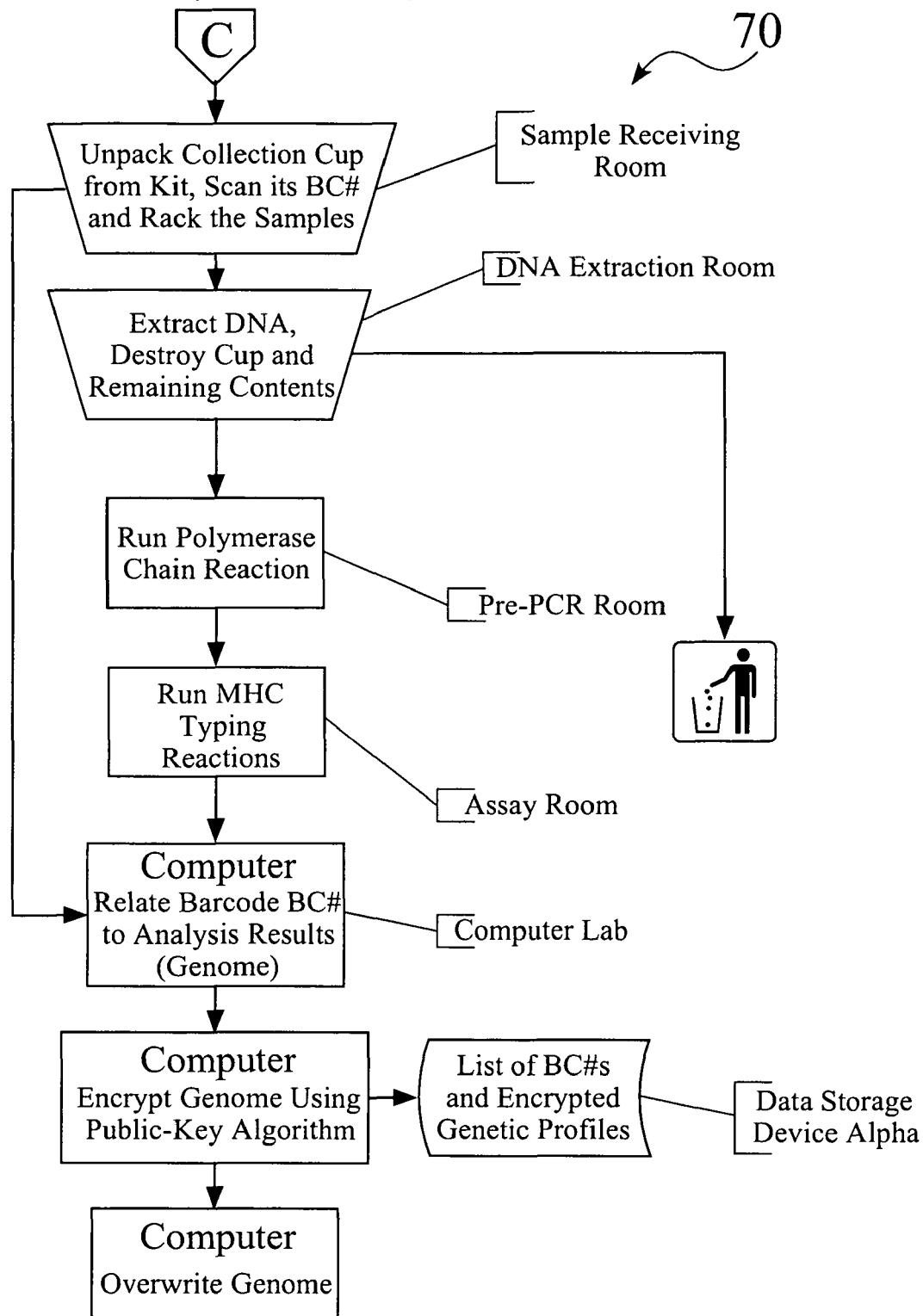

FIG. 34 is a flow chart which illustrates laboratory analysis, matching and reporting tasks.

Figure 35:
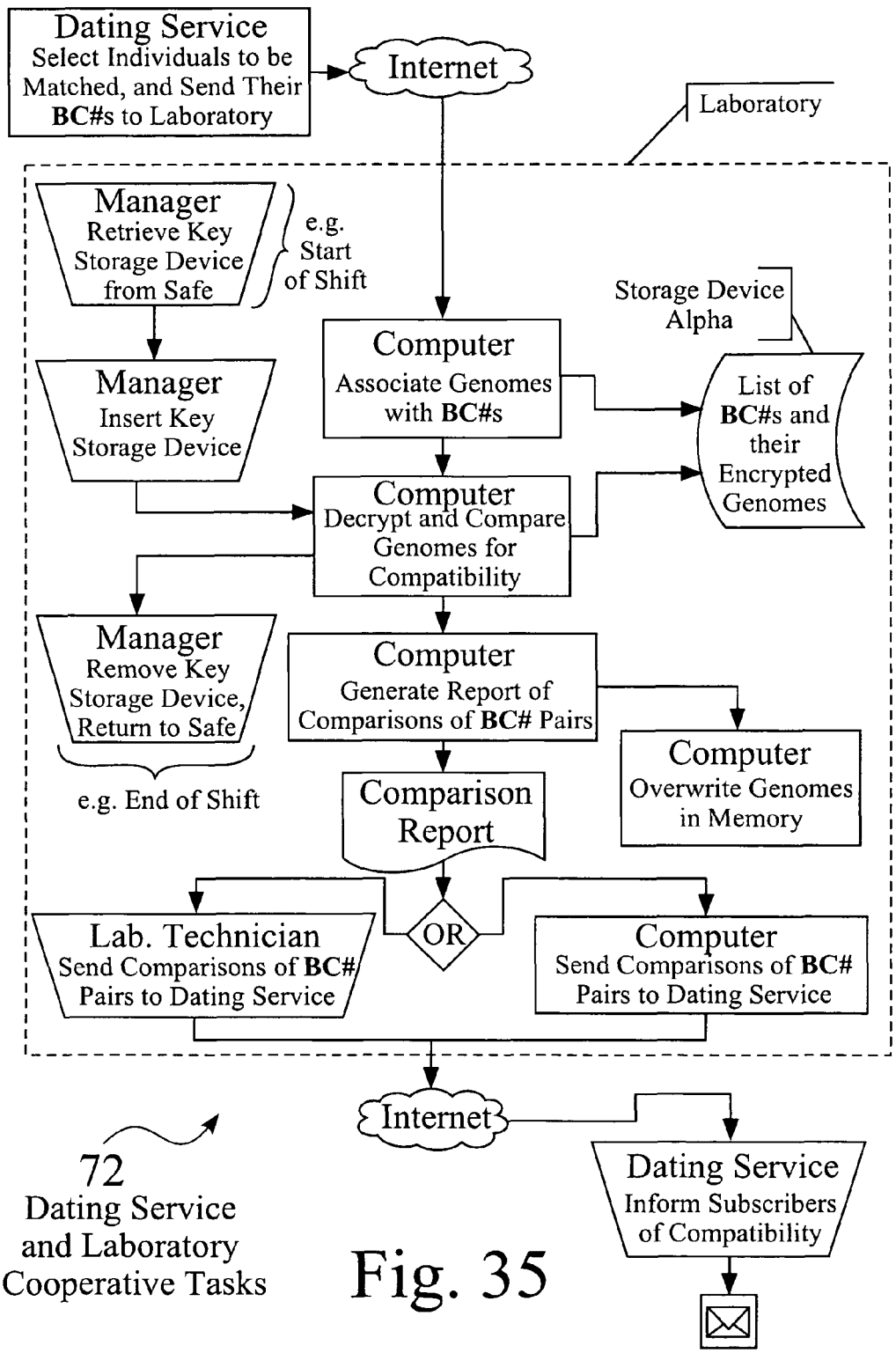

FIG. 35 is a flow chart which illustrates dating service and laboratory cooperative tasks.

Figure 36:
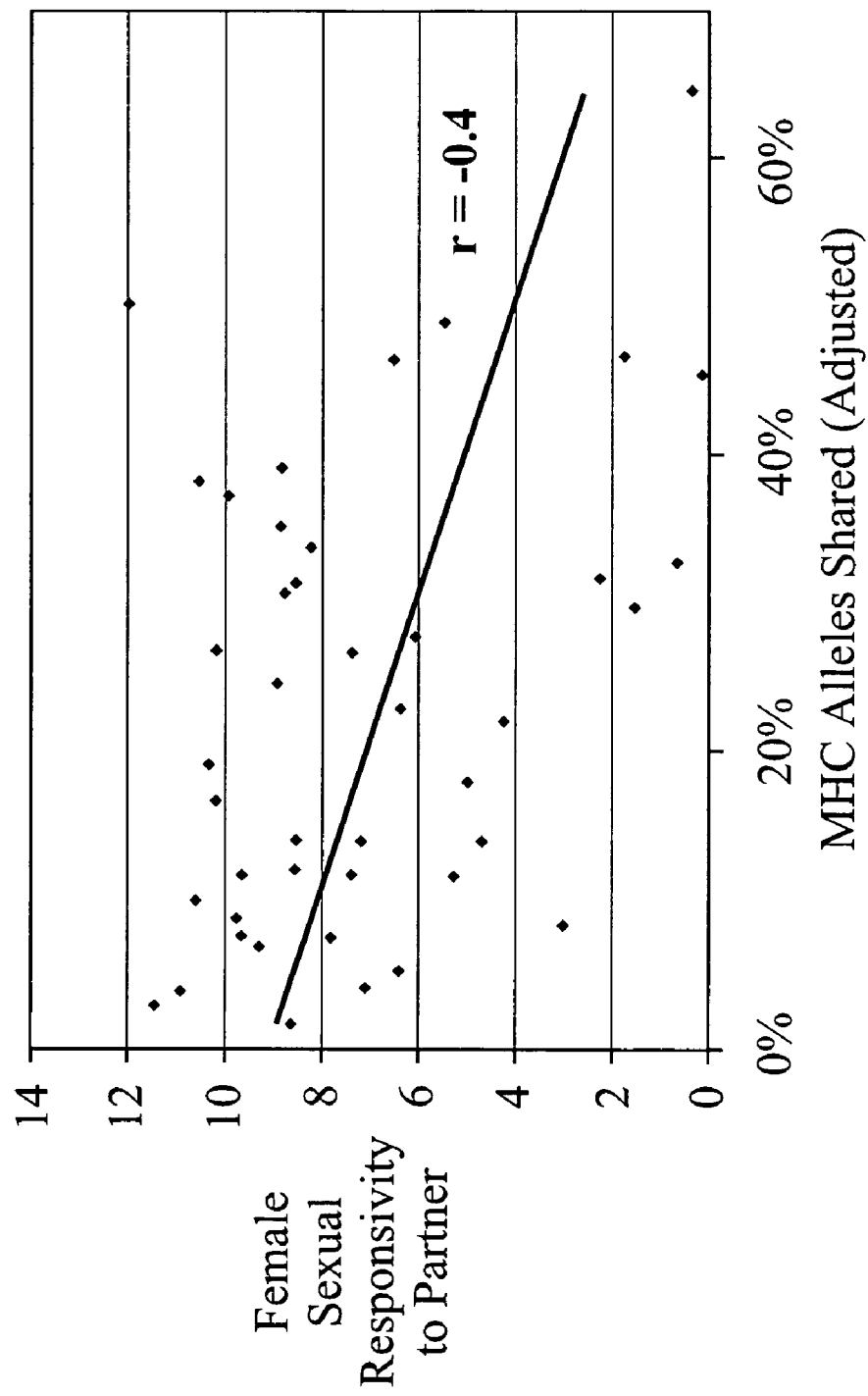

FIG. 36 is a graph of MHC alleles shared on the horizontal axis, a woman's sexual responsivity to partner on the vertical axis.

Figure 37:
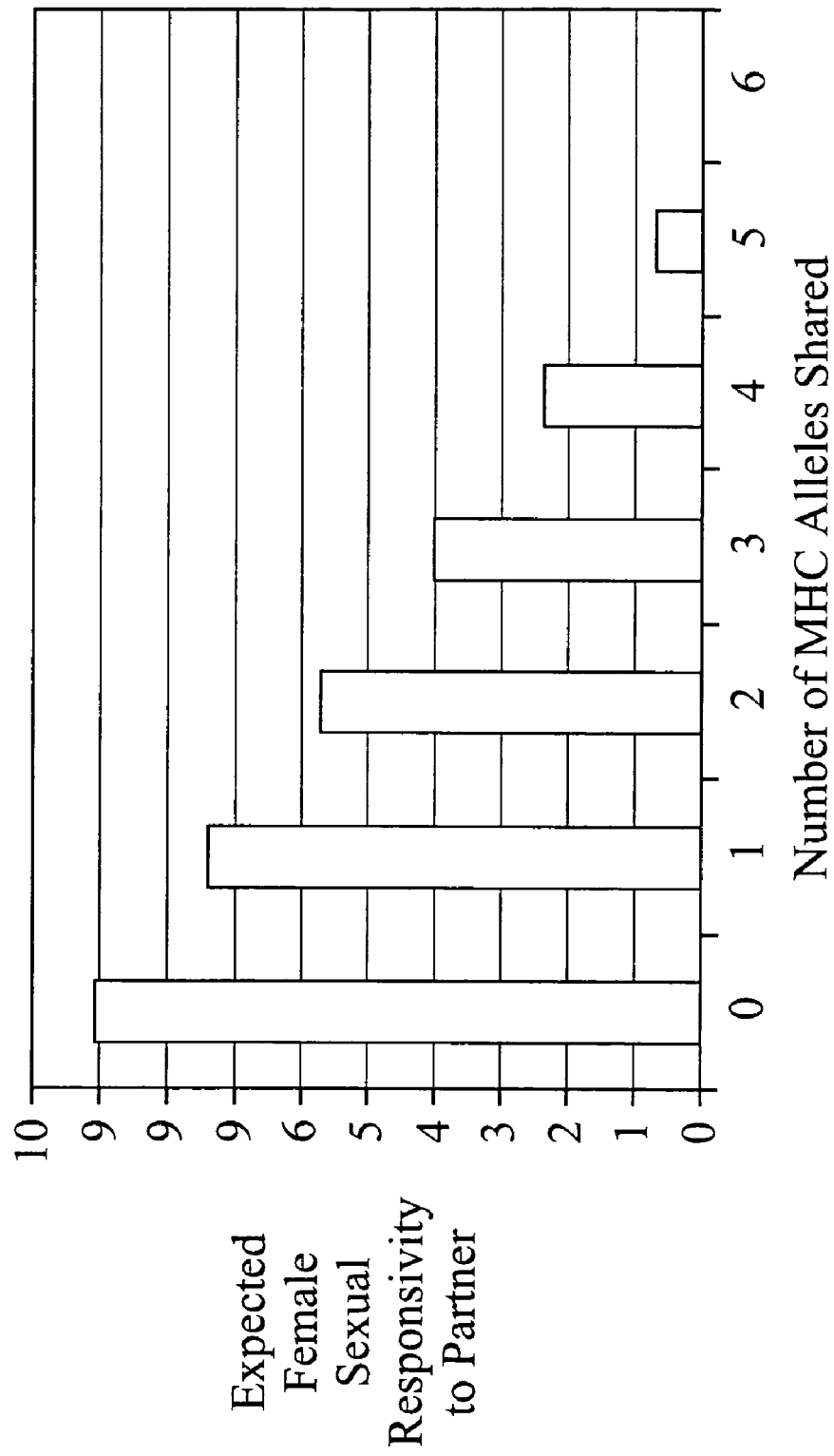

FIG. 37 is a bar chart showing the number of MHC alleles shared on the horizontal axis, and the woman's expected sexual responsivity to her partner on the vertical axis.

Figure 38:
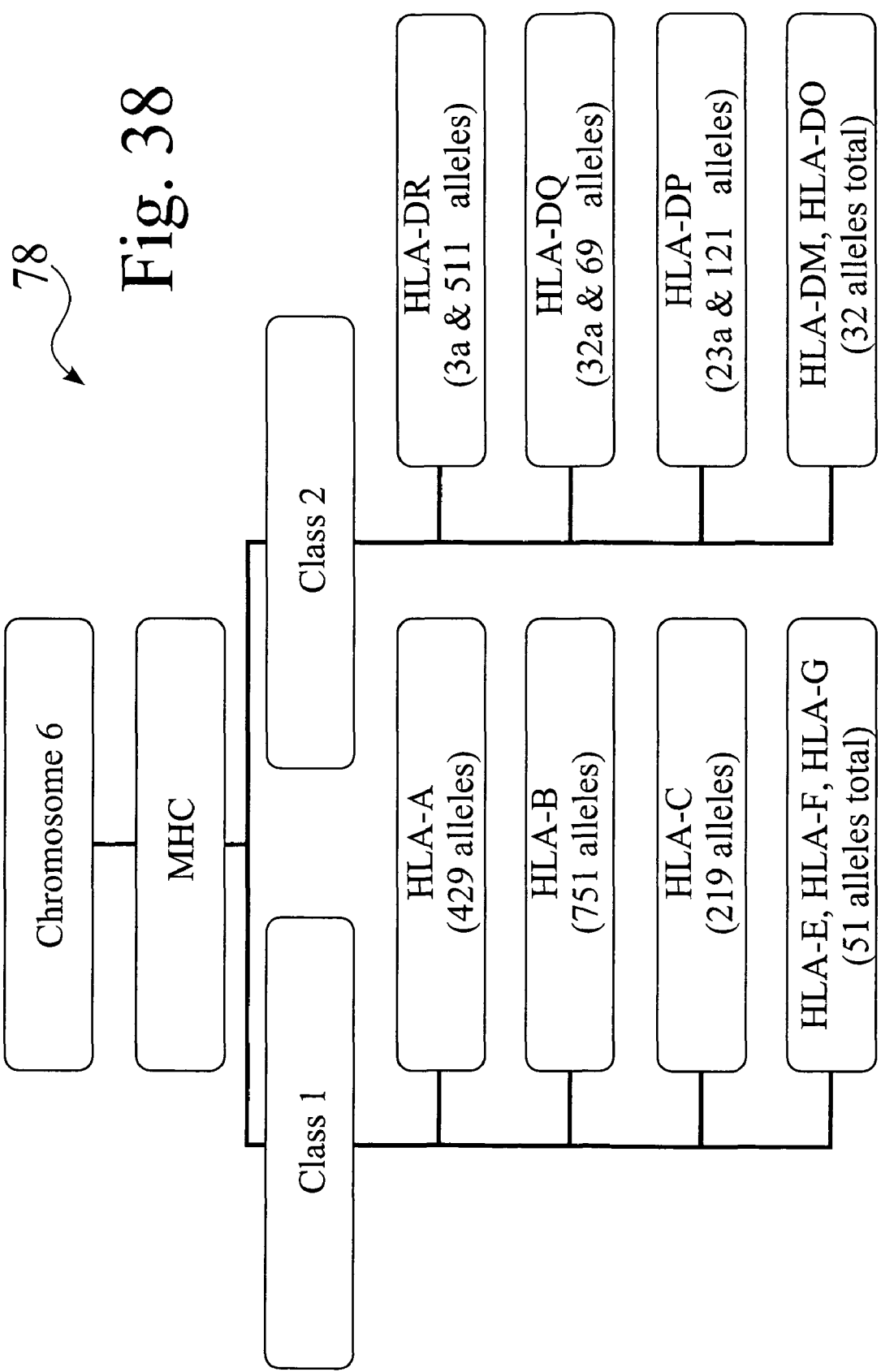

FIG. 38 is a chart that shows the relationship of alleles in the MHC Group on Human Chromosome No. 6.

FIG. 39 reveals the details of the MHC Allele Groups.

Figure 40:
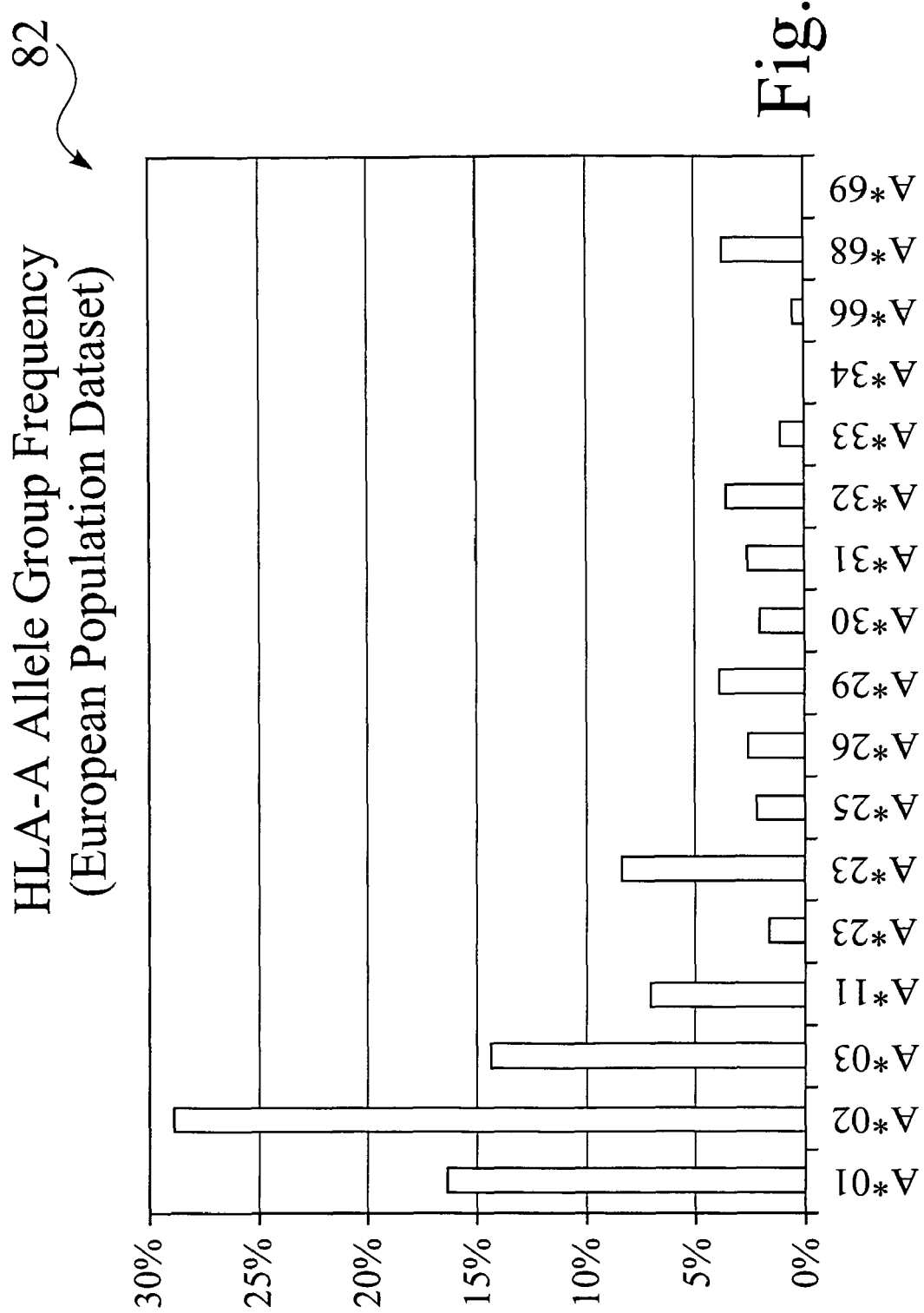

FIG. 40 illustrates HLA-A Allele Group Frequency for a European Population Dataset.

Figure 41:
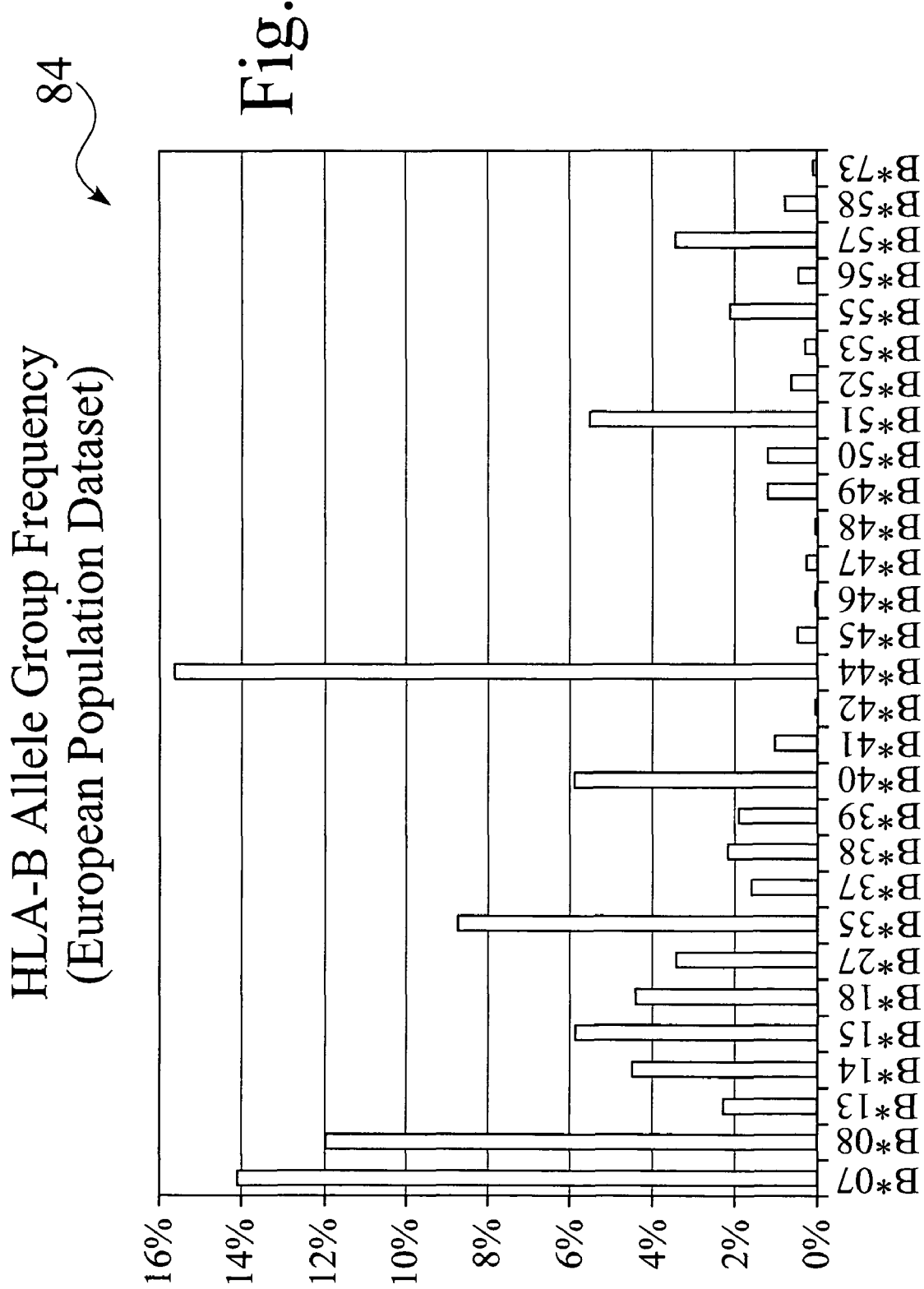

FIG. 41 illustrates HLA-B Allele Group Frequency for a European Population Dataset.

Figure 42:
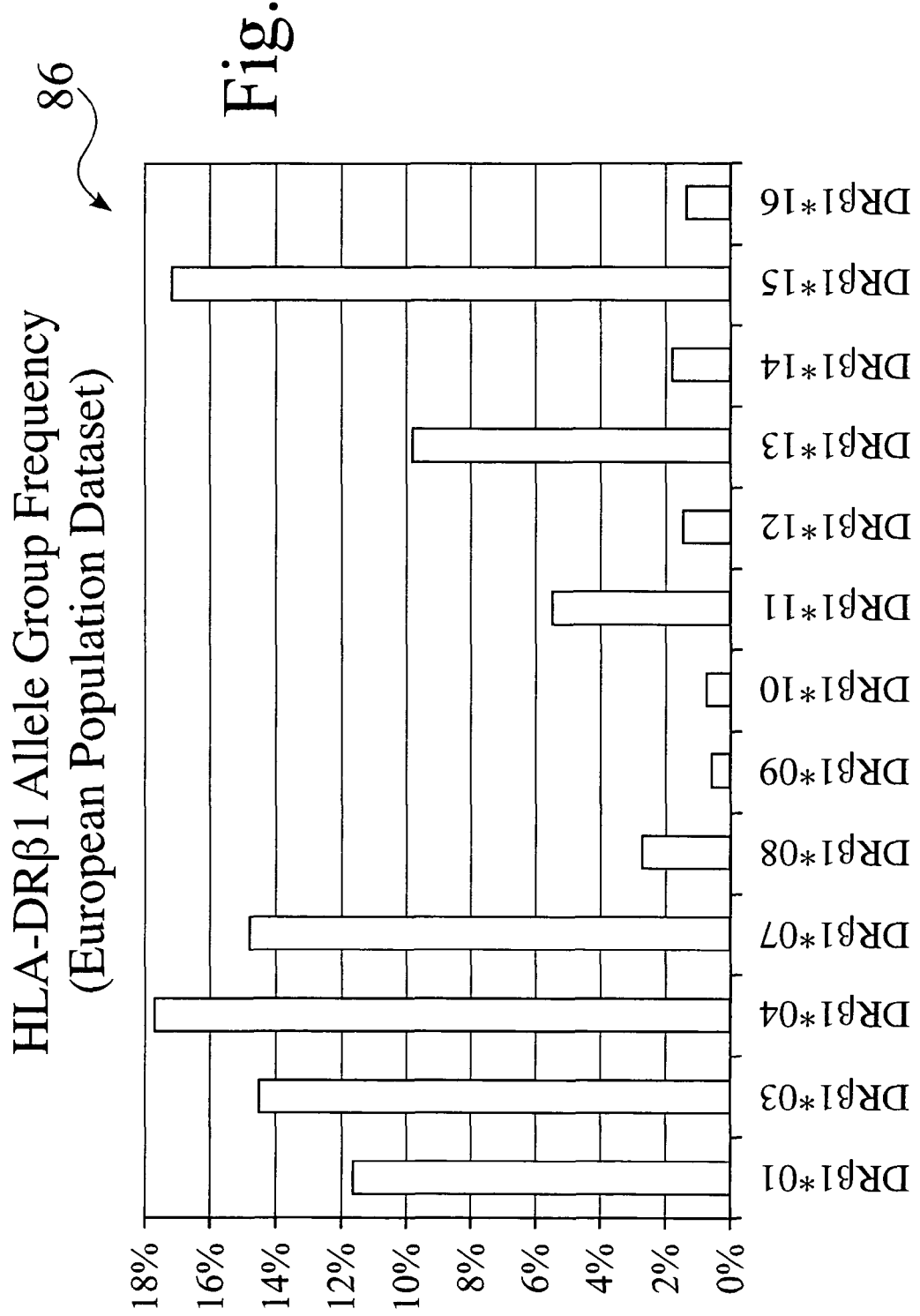

FIG. 42 illustrates HLA-DRβ1 Allele Group Frequency for a European Population Dataset.

Figure 43:
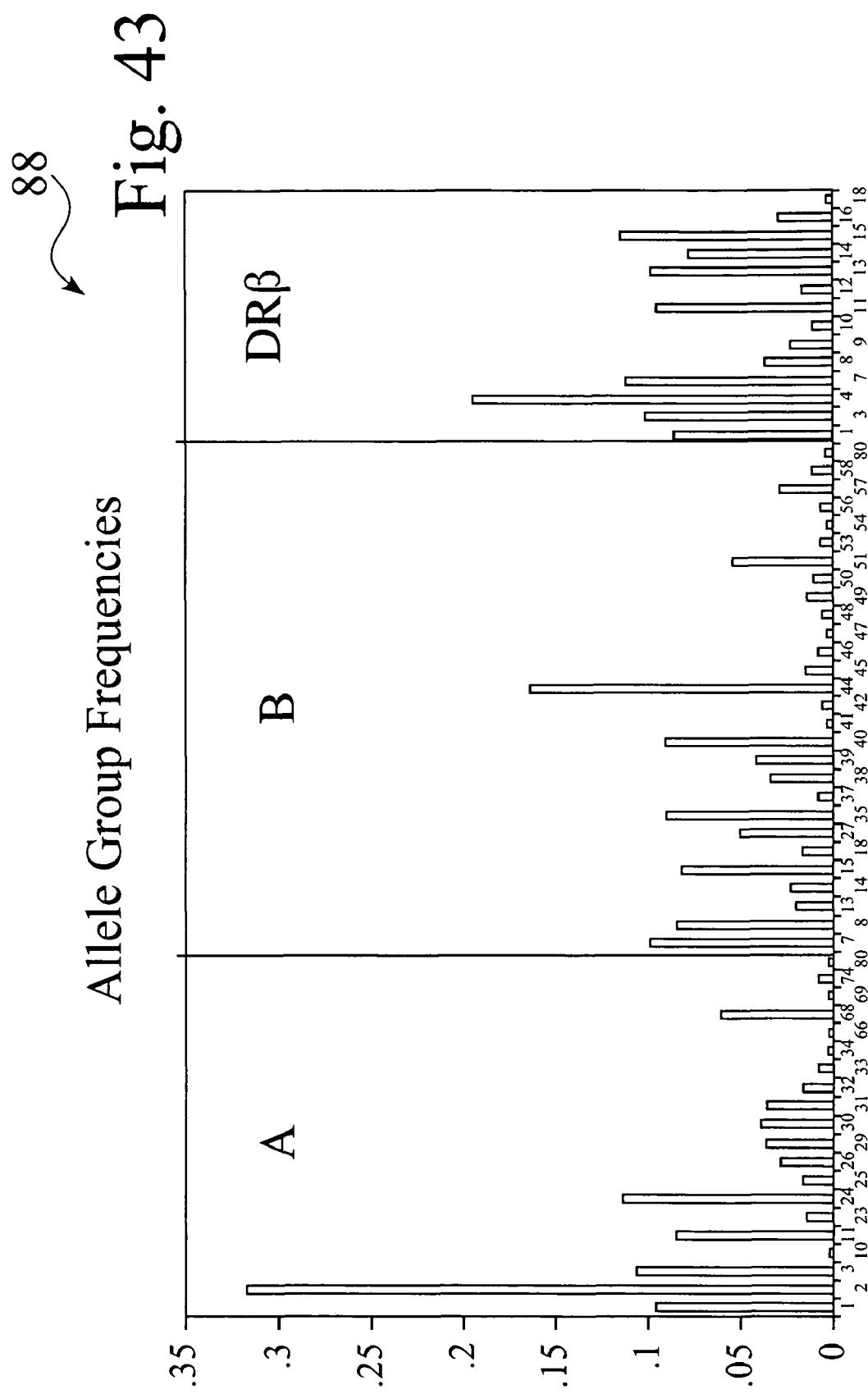

FIG. 43 depicts Allele Group Frequencies.

Figure 44:
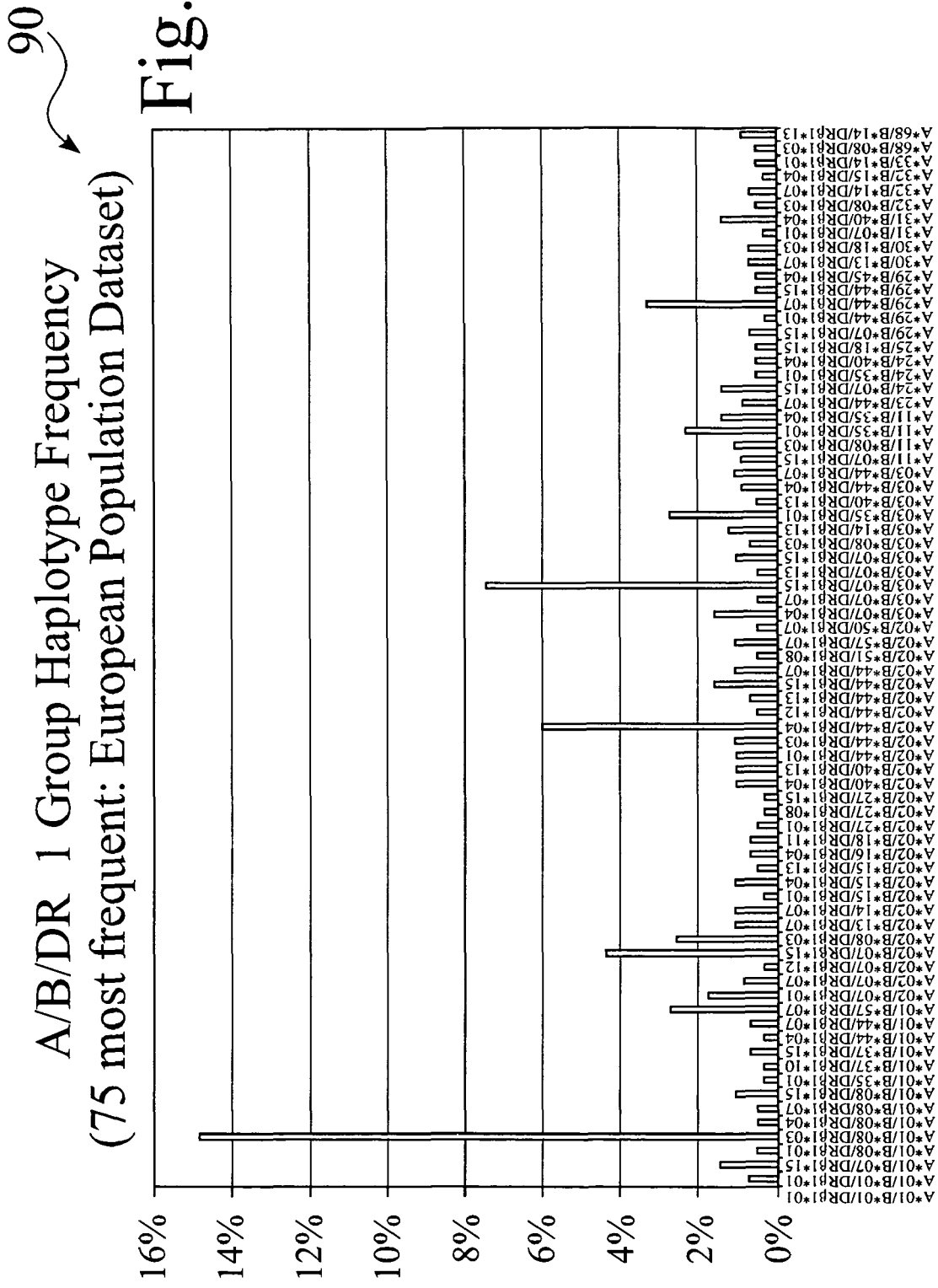

FIG. 44 depicts A/B/DRβ1 Group Haplotype Frequency.

Figure 45:
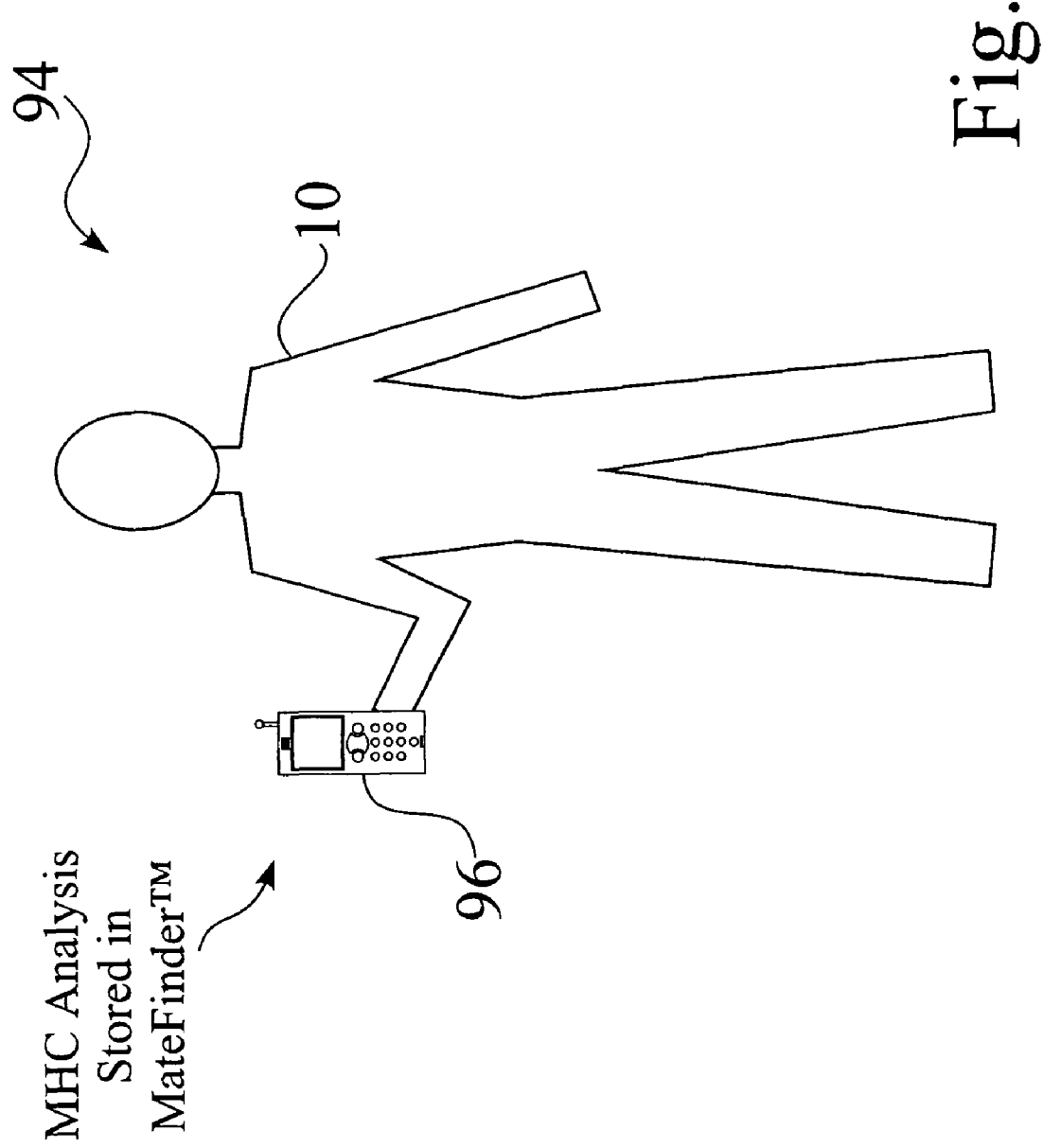

FIG. 45 shows a man using a MateFinder™ device.

Figure 46:
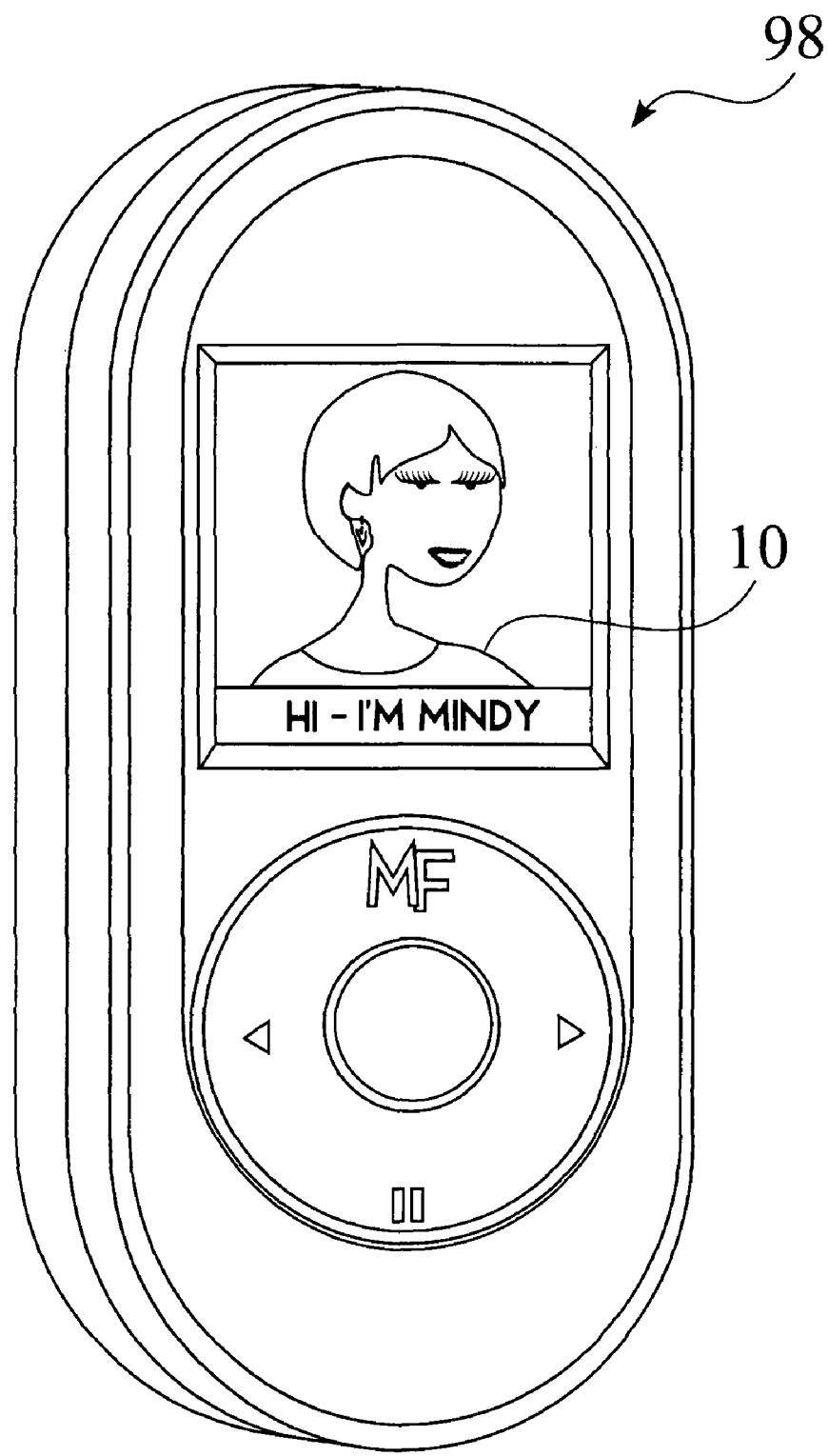

FIG. 46 provides a more detailed view of a MateFinder™ device.

Figure 47:
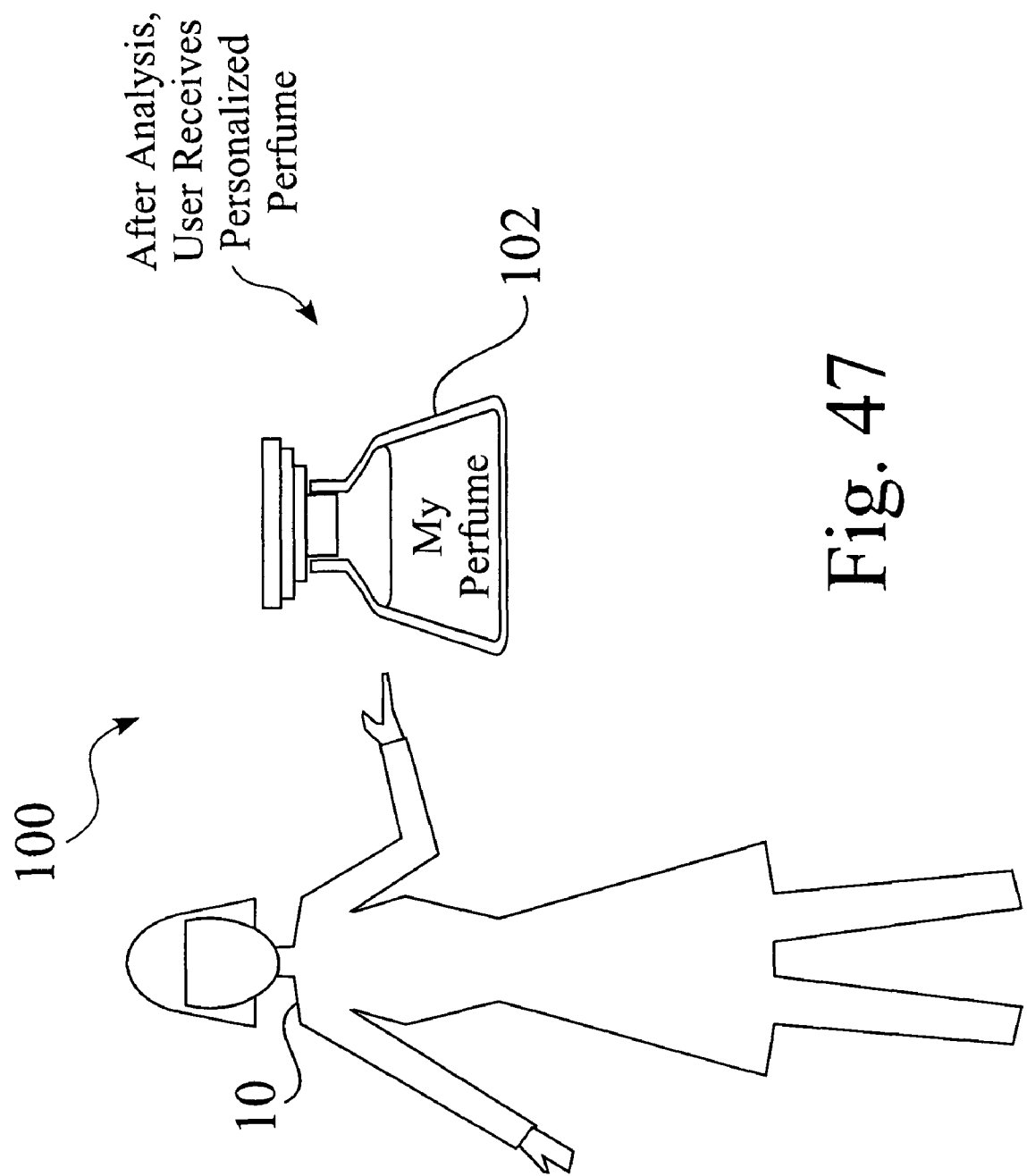

In FIG. 47, a woman whose tissue sample has already been analyzed receives a custom-formulated perfume which contains aromas that correspond to her genetic attributes.

Figure 48:
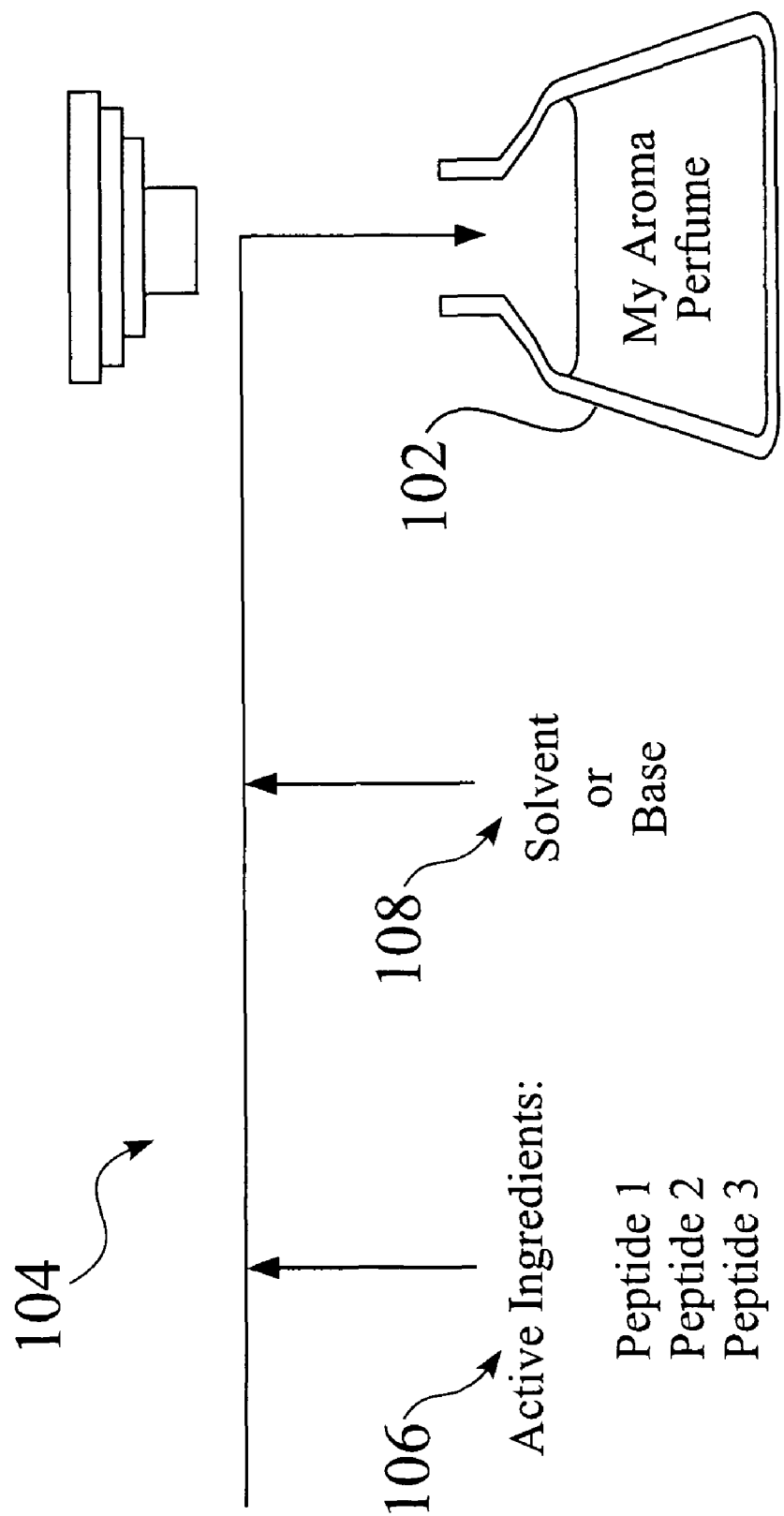

FIG. 48 depicts a method of manufacturing a customized perfume.

Figure 49:
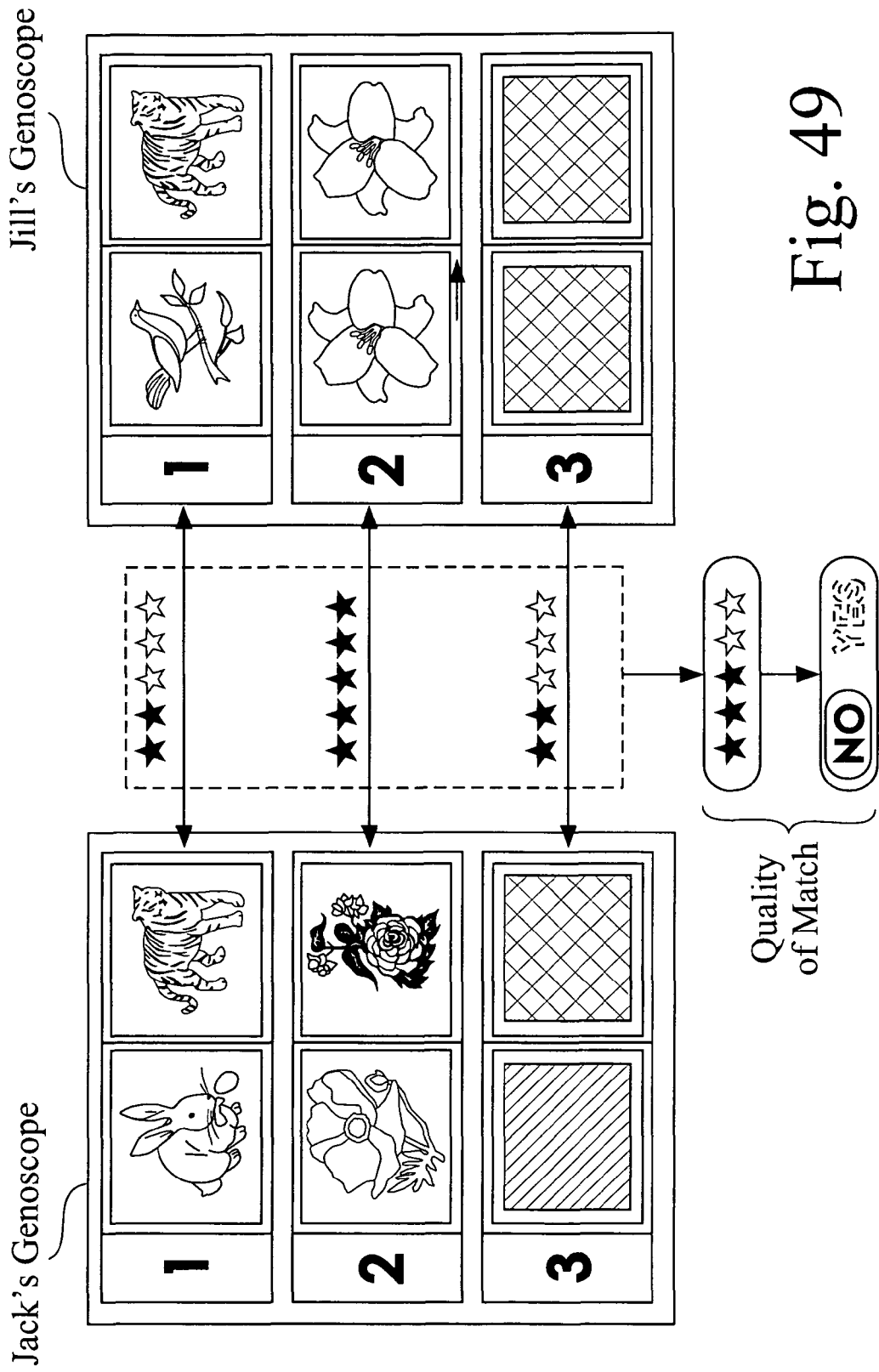

FIG. 49 presents a Genoscope™ graphical aid, which may be used to indicate good or bad matches.

Figure 50:
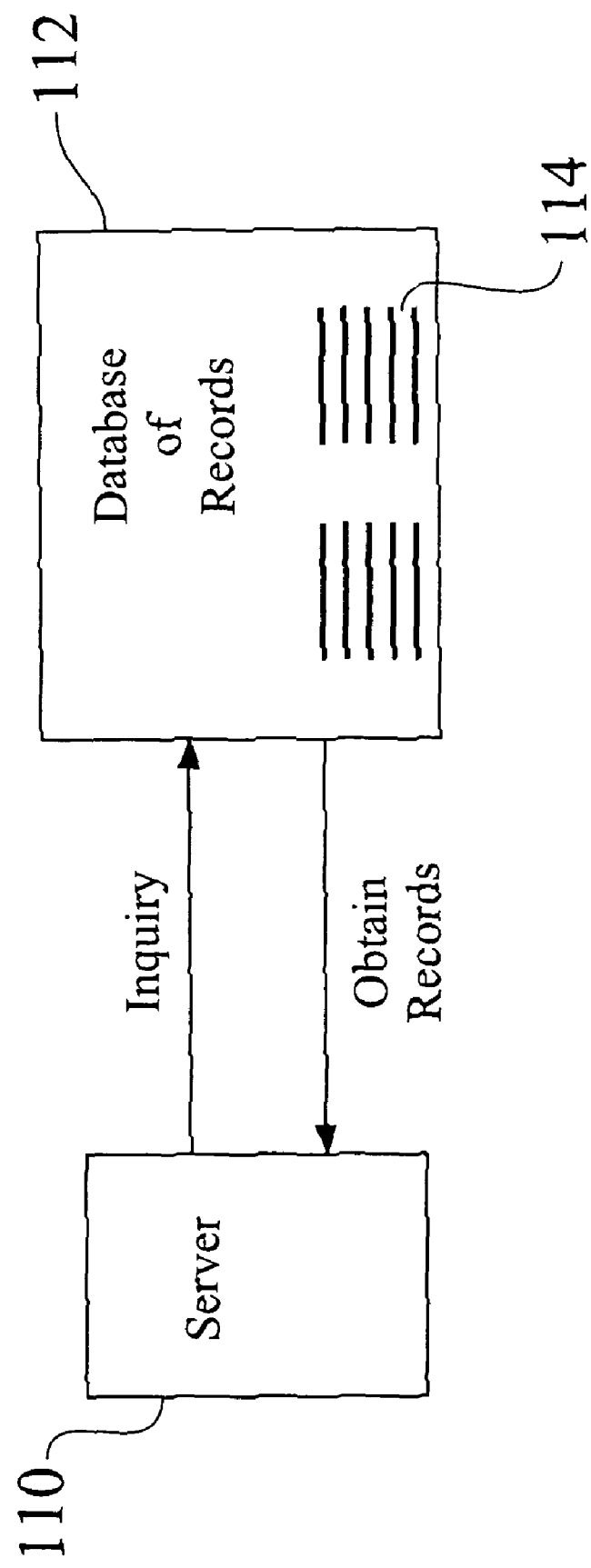

FIG. 50 is a block diagram showing a server and an external database of records.

FIGS. 51 and 52 depict fictitious credit card statements owned by two different individuals.

Figure 53:
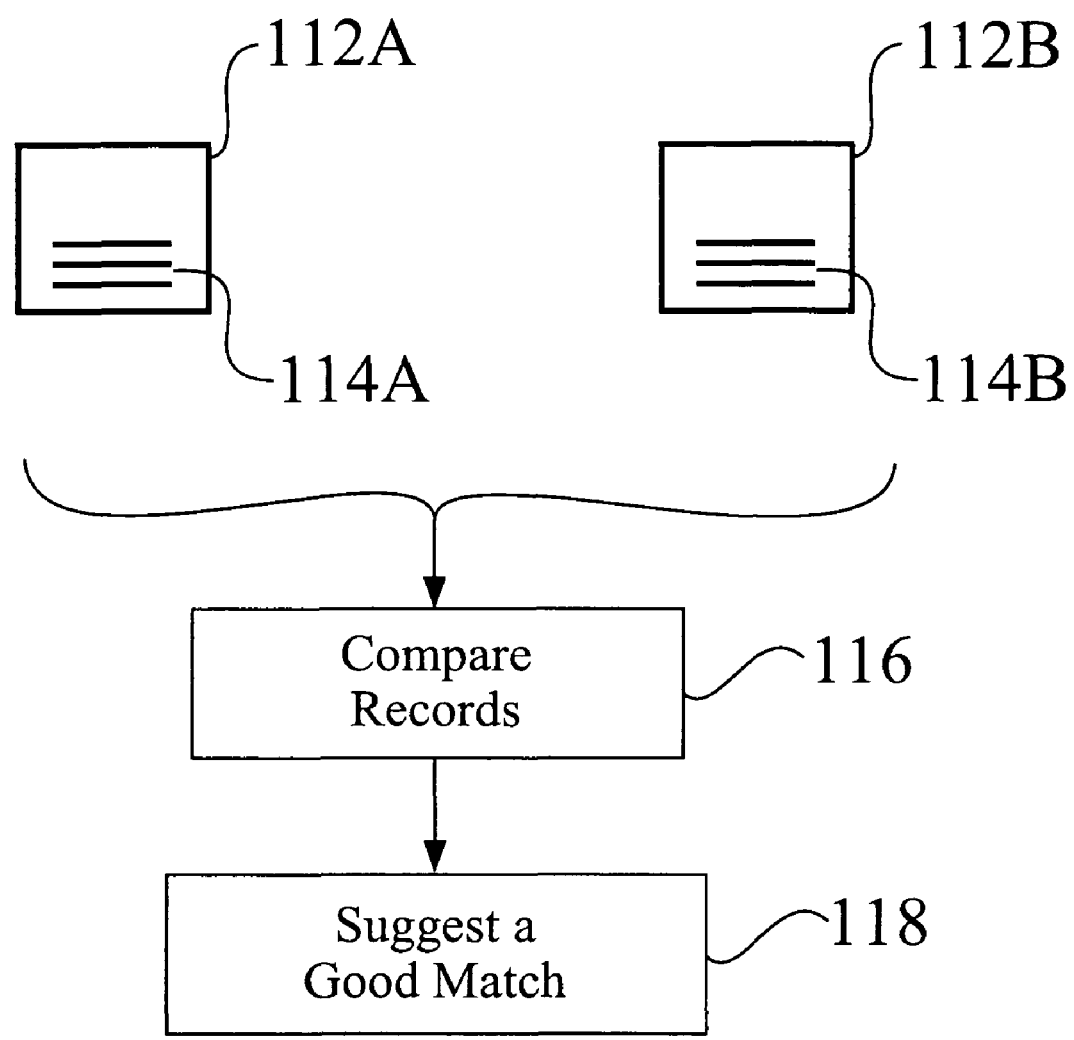

FIG. 53 illustrates the process of comparing the purchases listed in the credit card statements shown in FIGS. 51 and 52 to assist in the process of suggesting a good match.

Figure 54:
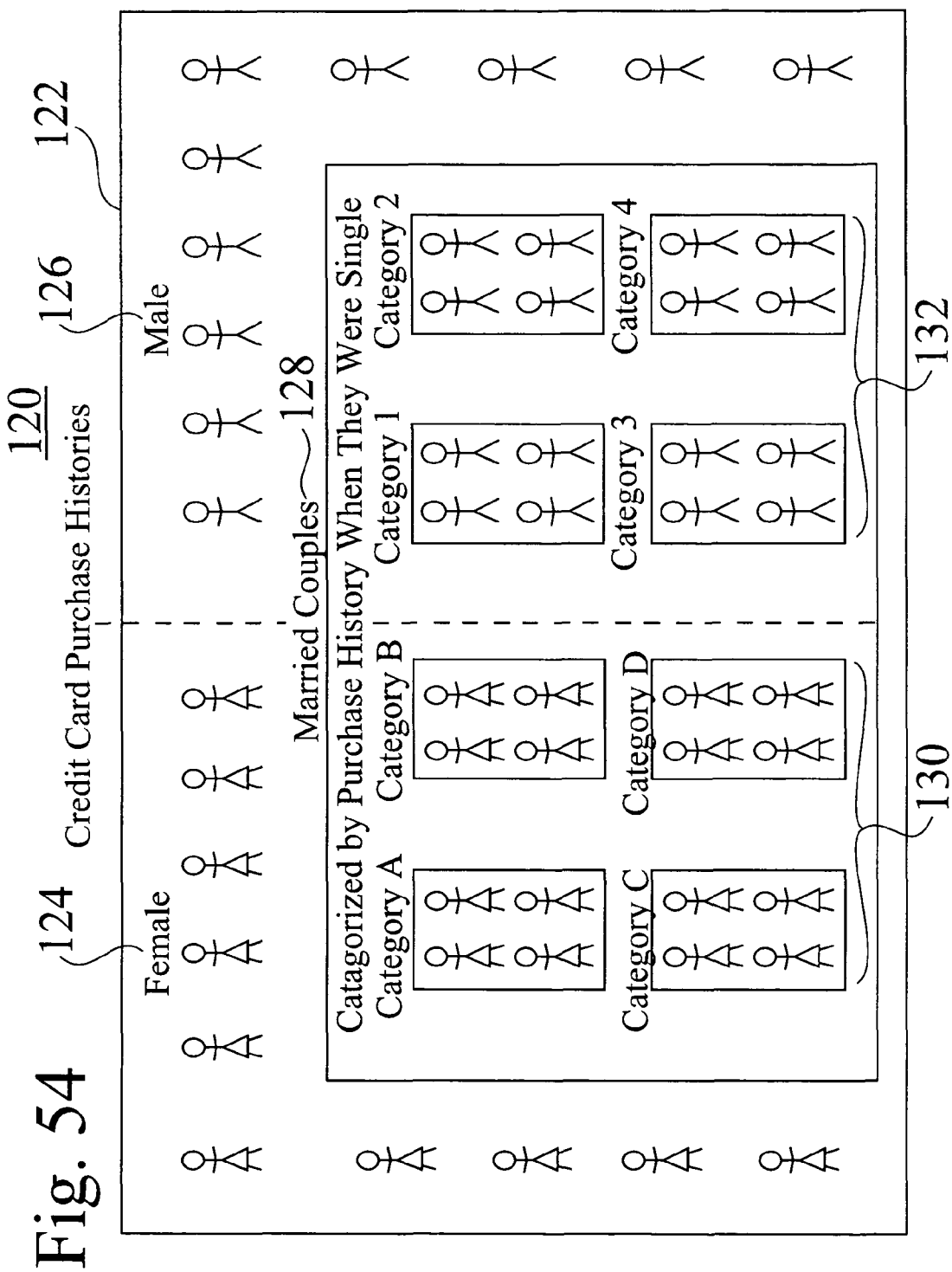
Figure 55:
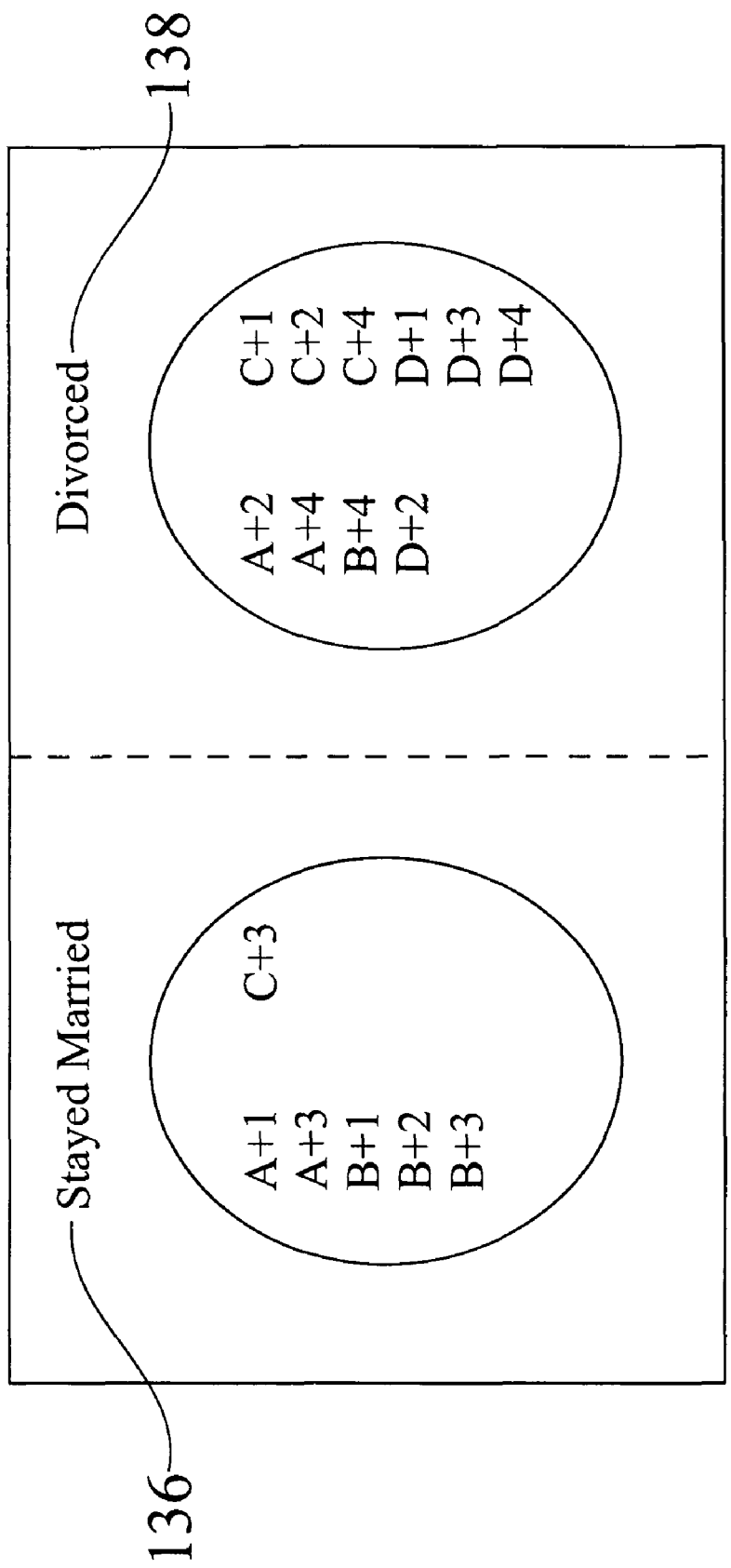
Figure 56:
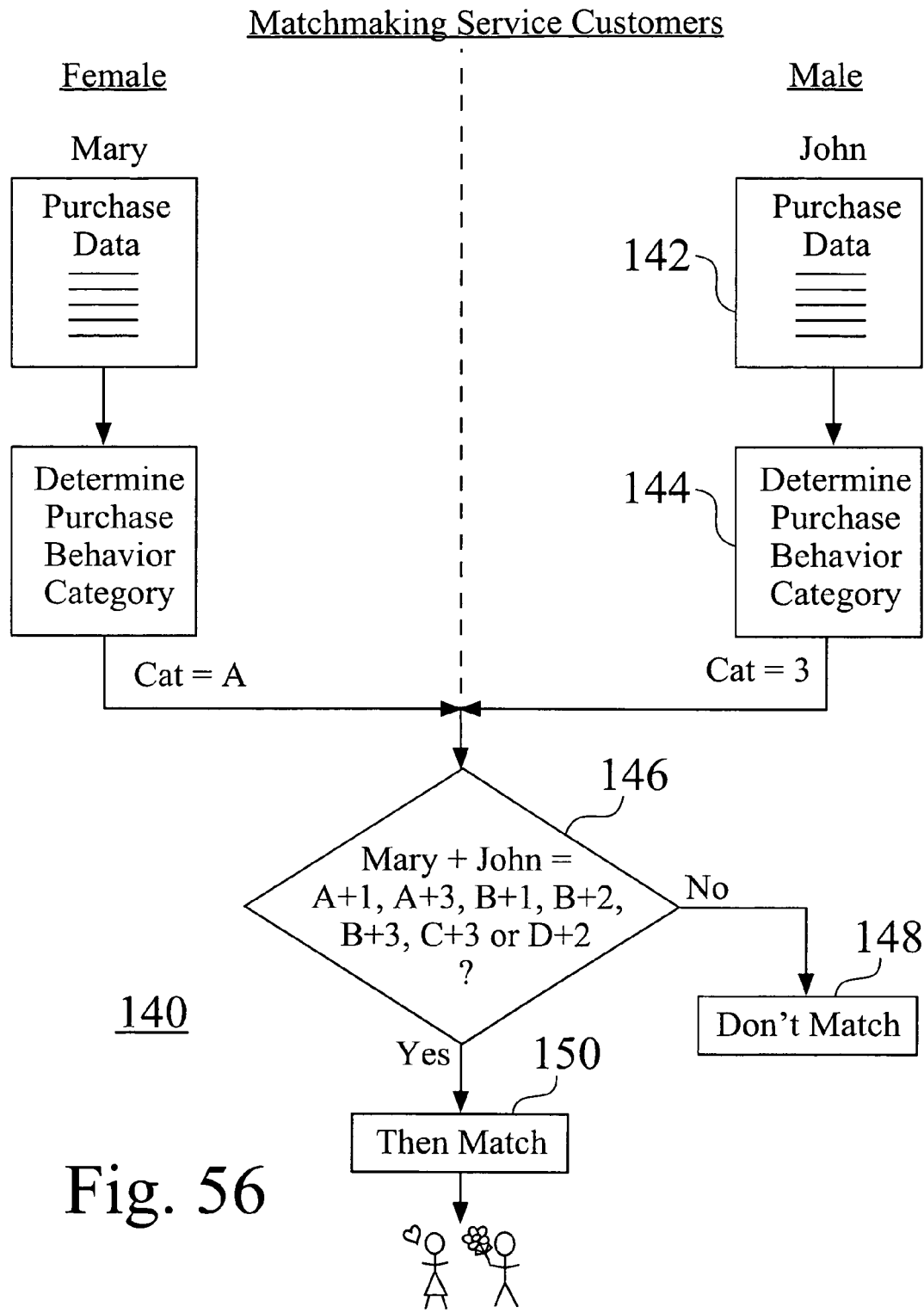

FIGS. 54, 55 and 56 depict fictitious pages of three different members of a social networking website.

Figure 57:

FIG. 57 supplies a diagram that shows how personal characteristics or interests obtained from social networking webpages are used to assist in the process of suggesting a good match.

Figure 58:
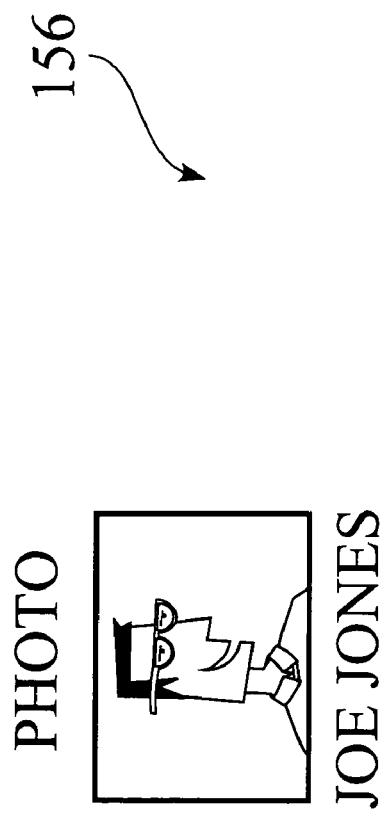

FIG. 58 offers a schematic illustration of credit card purchase history data.

Figure 59:
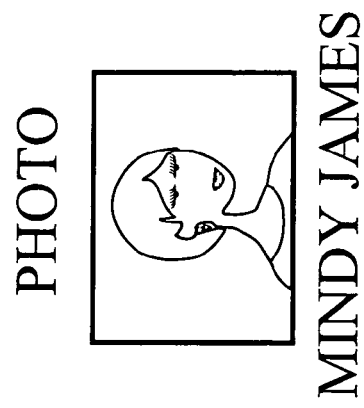

FIG. 59 shows how purchase history data is associated with marital status.

Figure 60:
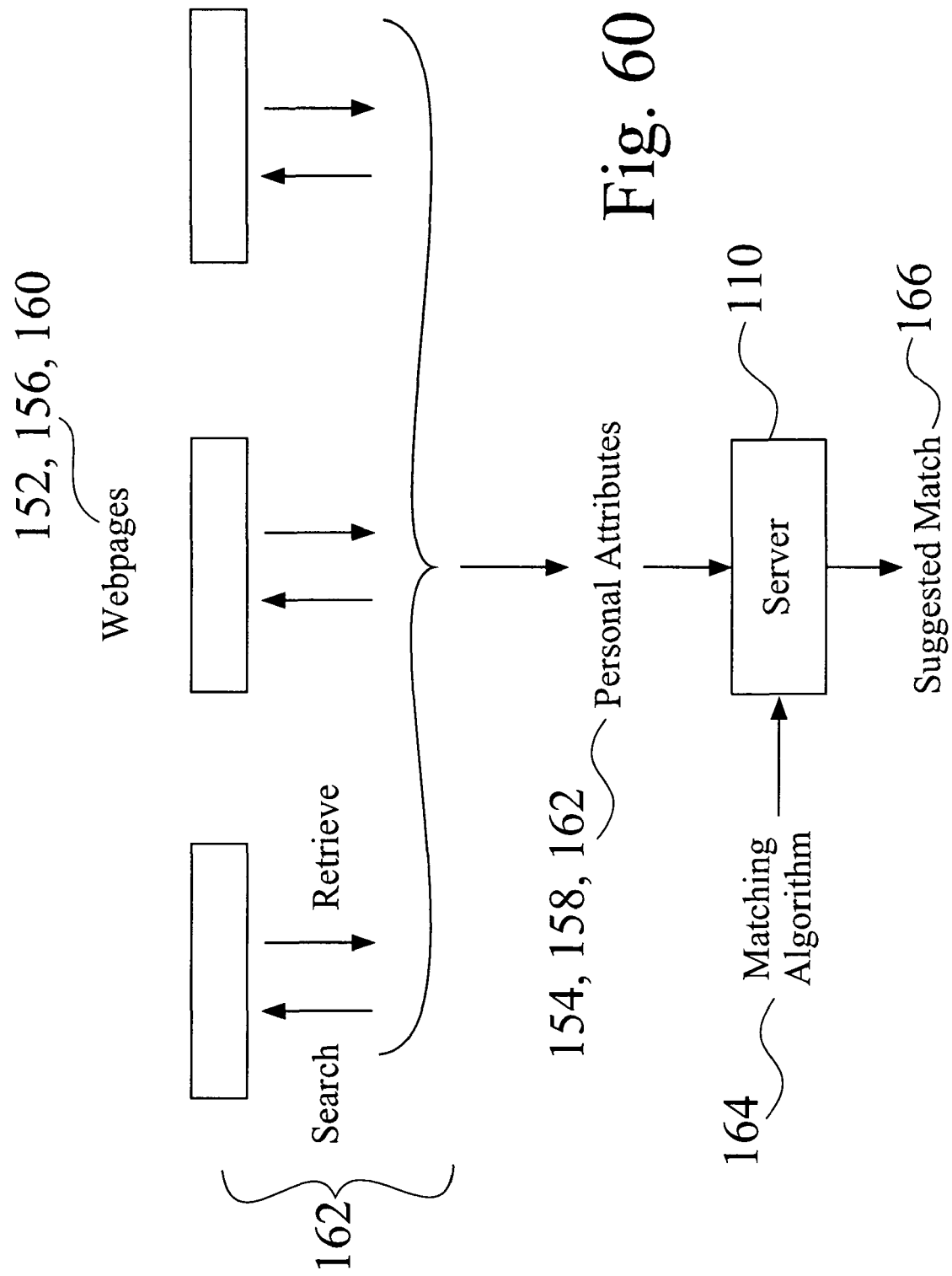

FIG. 60 is a flow chart which depicts a matchmaking method based upon purchase history data and marital status.

Figure 61:
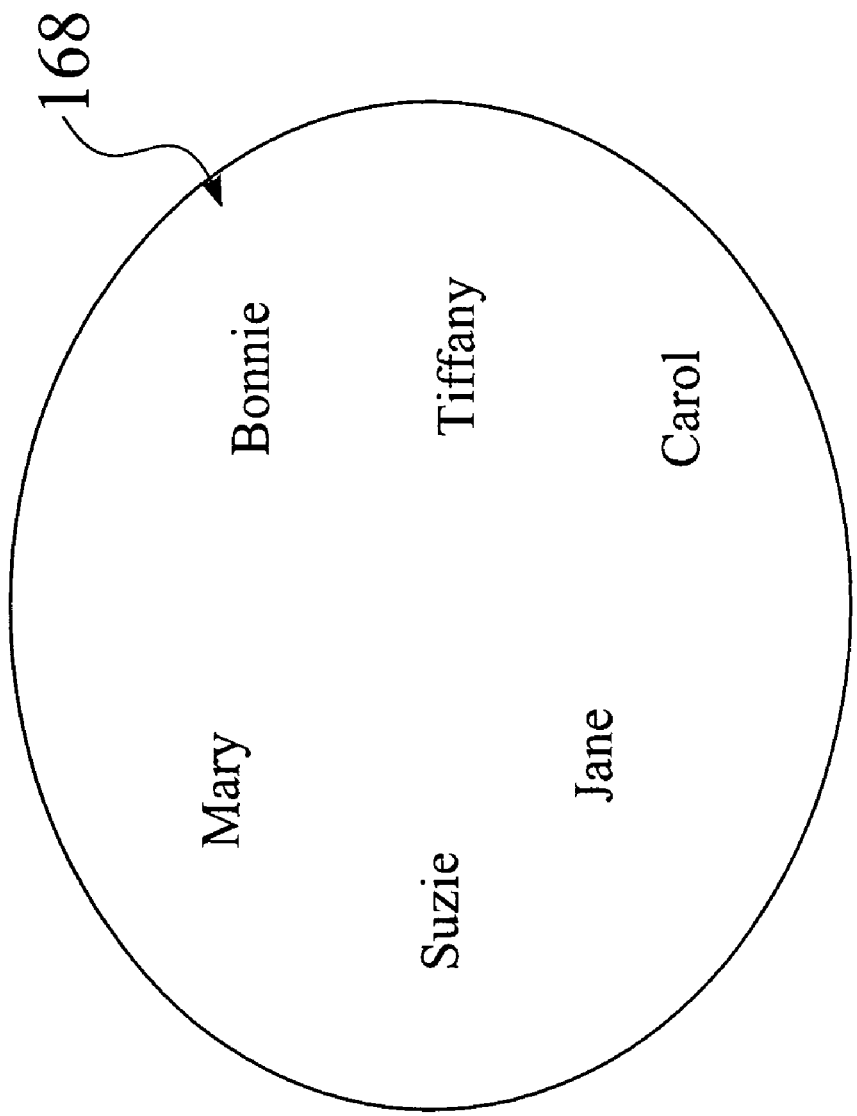

FIG. 61 provides a schematic representation of all the members of a social networking website.

Figure 62:
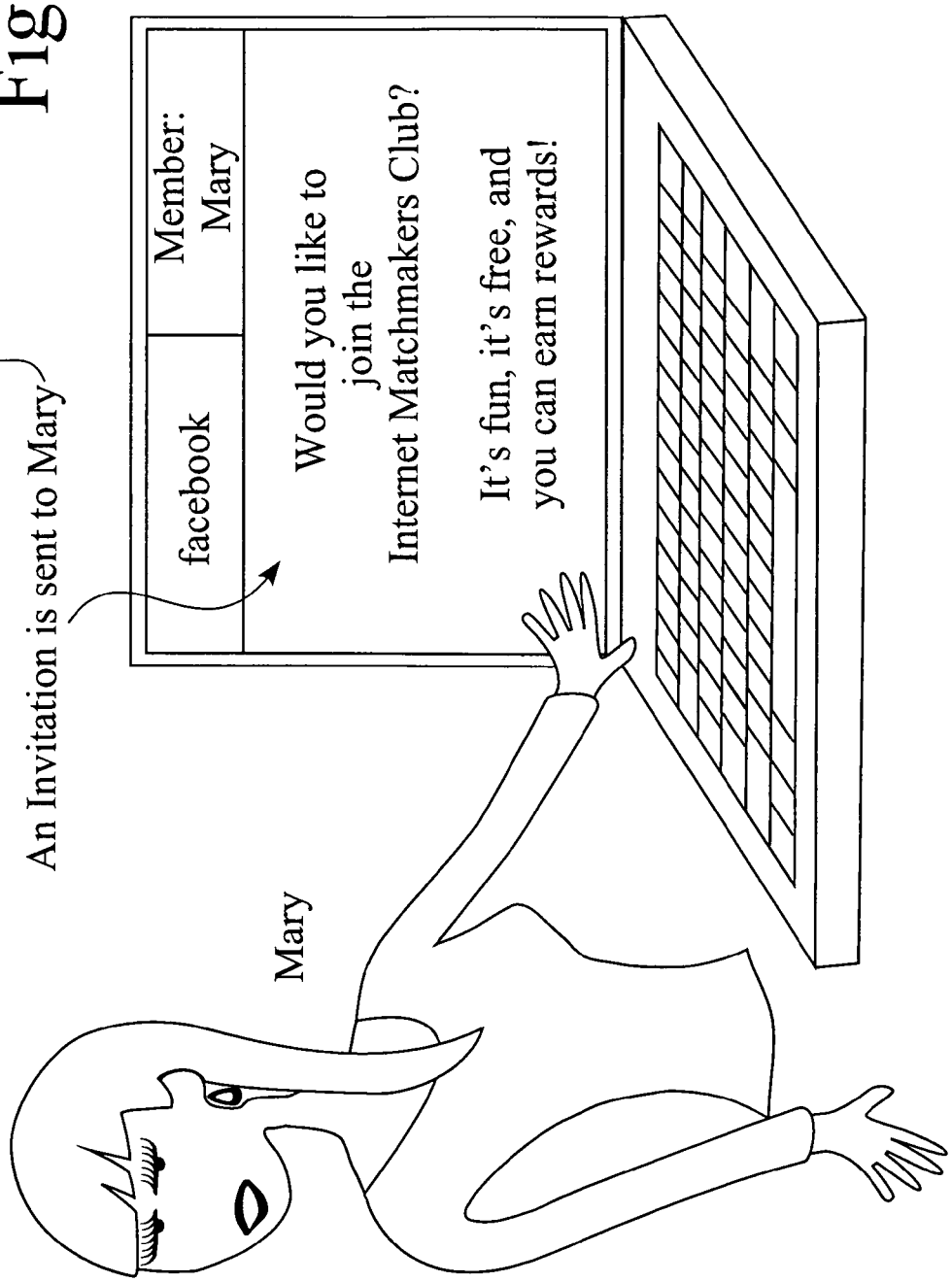

FIG. 62 shows a woman who has visited a social networking website, where she views an offer to join the Internet Matchmaker Club.

Figure 63:
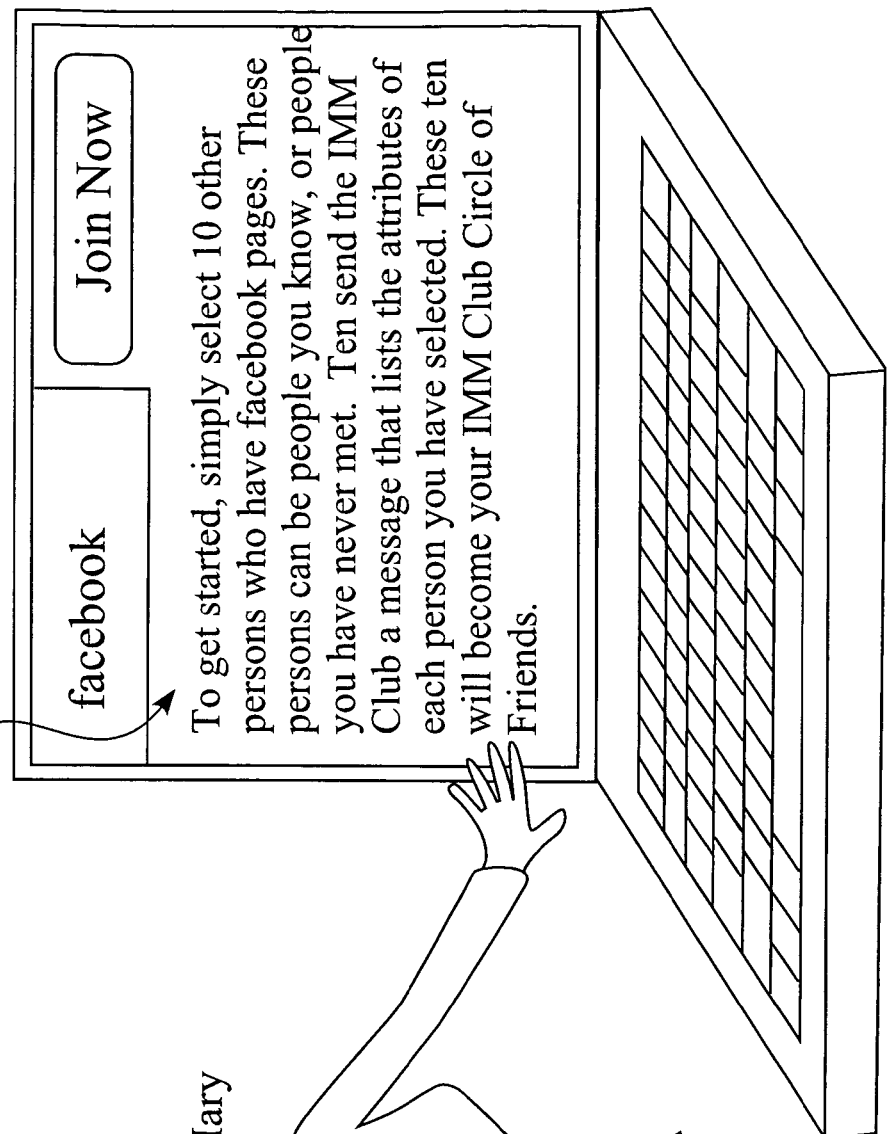

FIG. 63 shows the same woman viewing a message which explains how the Internet Matchmakers Club works.

Figure 64:
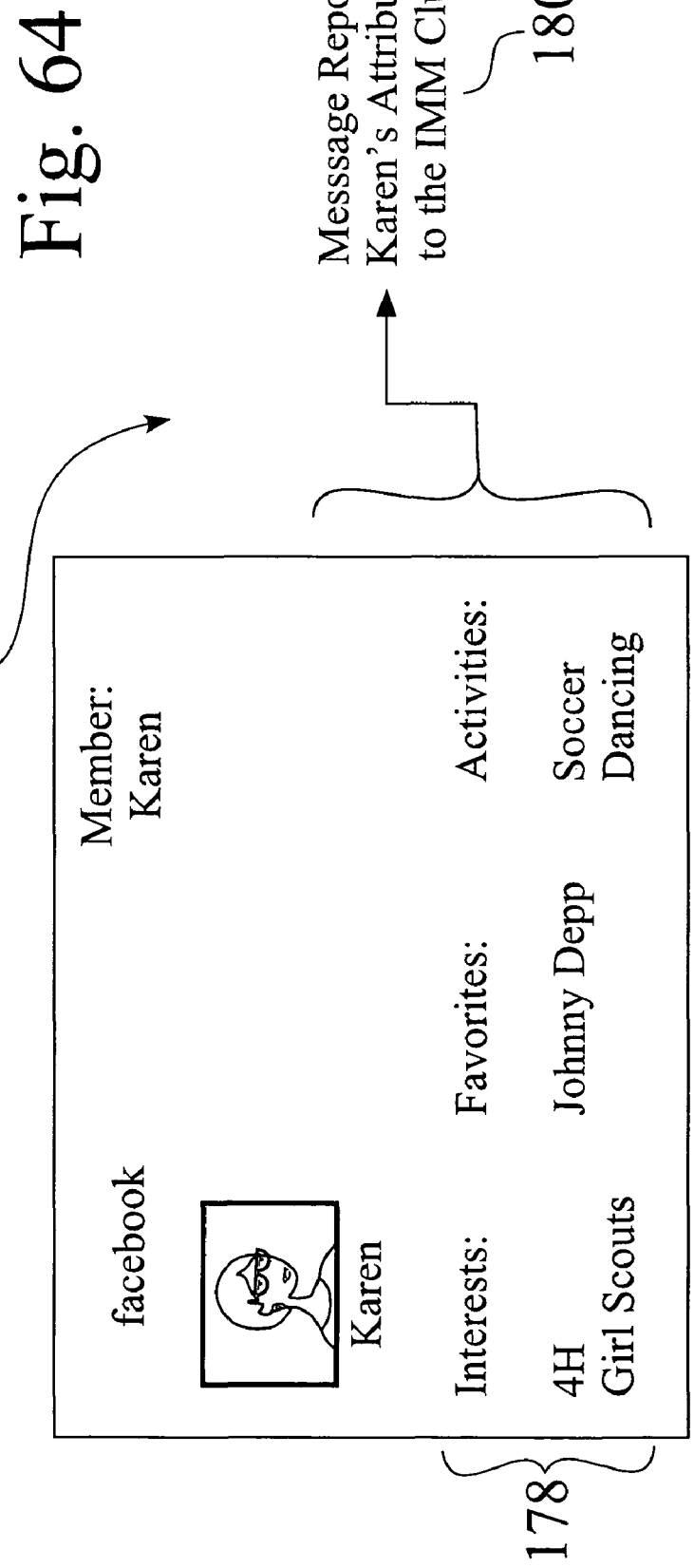

FIG. 64 reveals how one member of a social network reports the personal attributes of another individual who is also a member of the same social network.

Figure 65:
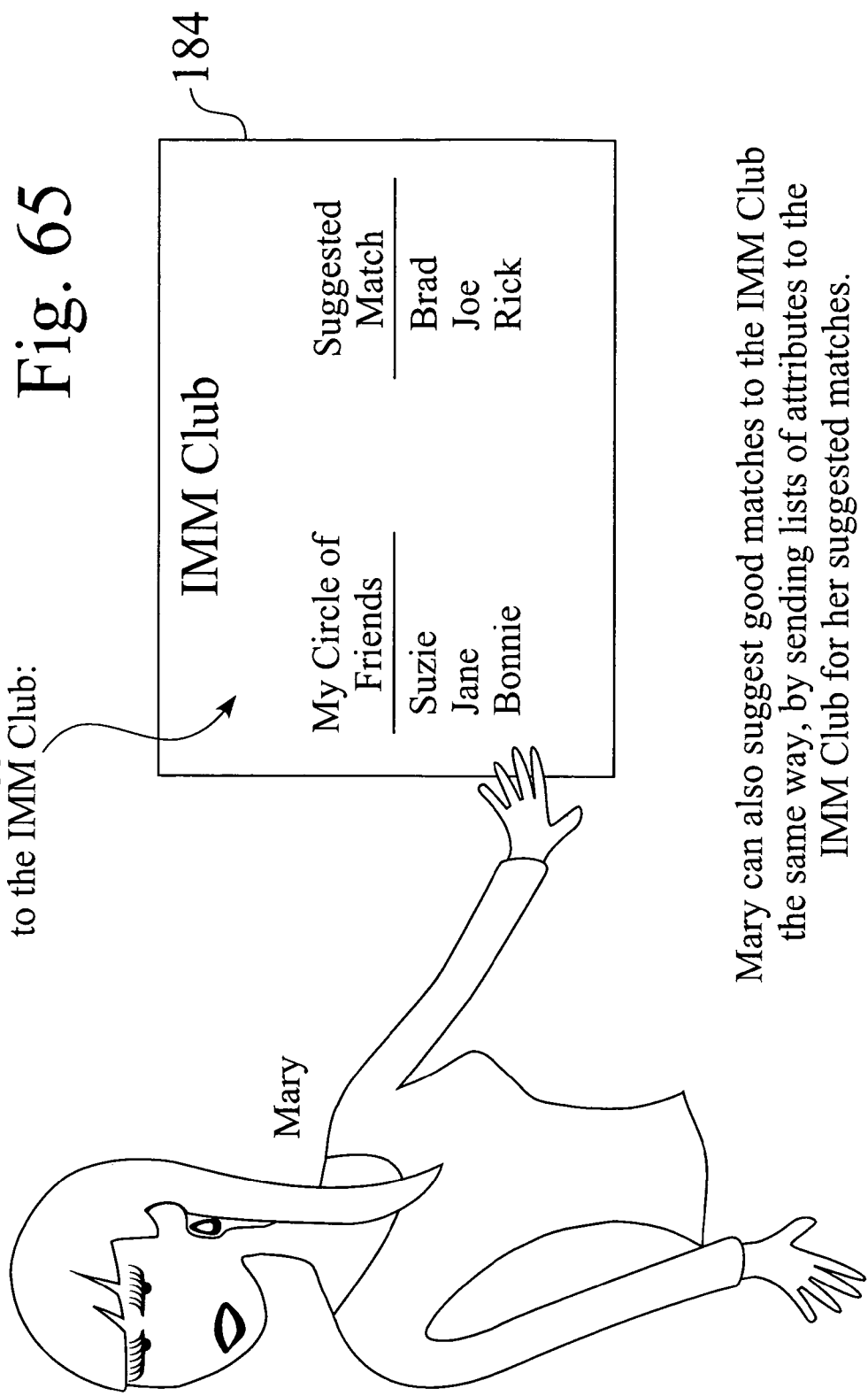

FIG. 65 supplies a view of a member of the IMM Club who has both reported attributes of others to the IMM Club, and has also suggested good matches.

Figure 66:
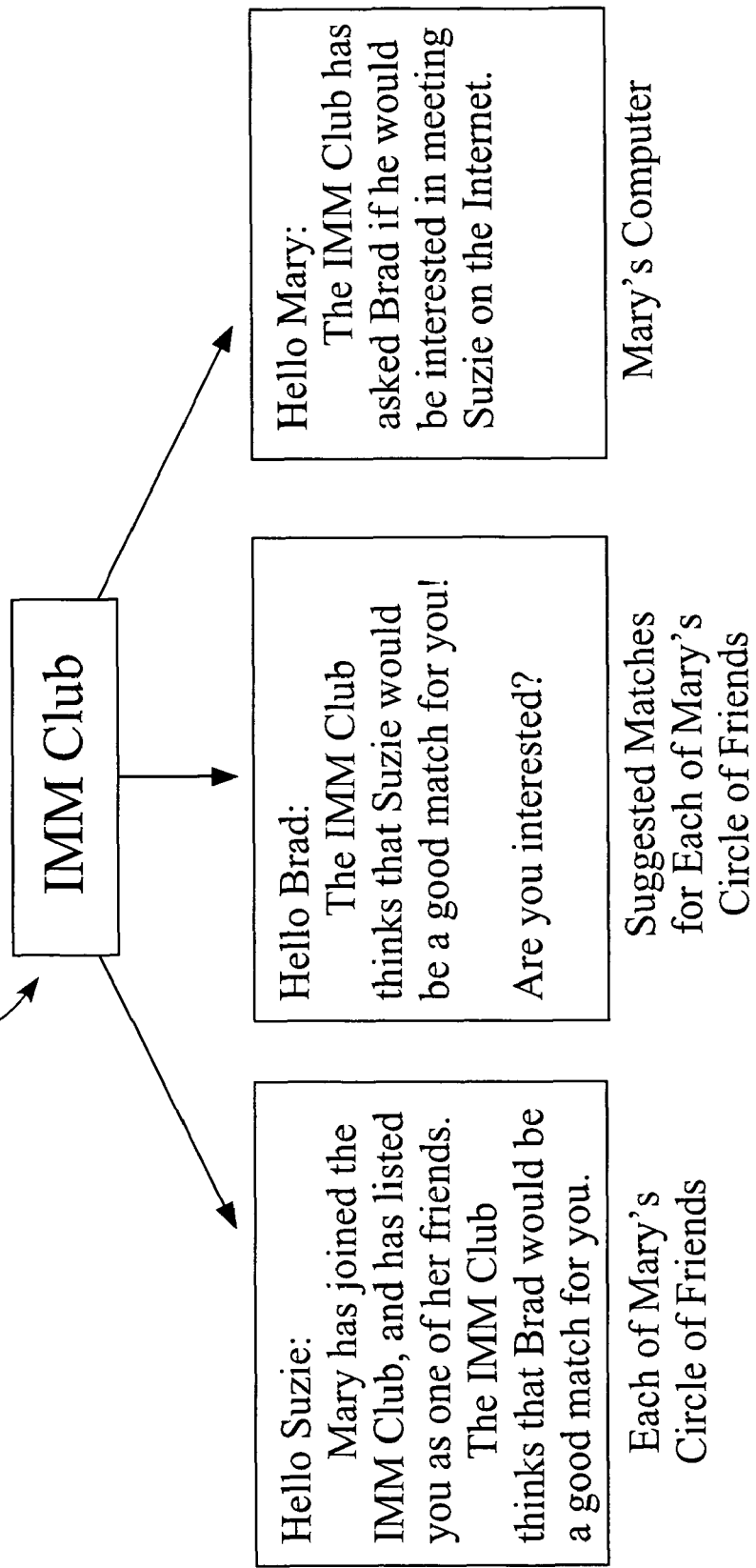

FIG. 66 depicts IMM Club correspondence among the original matchmaker, her circle of friends, and persons who have been suggested as good matches.

Figure 67:
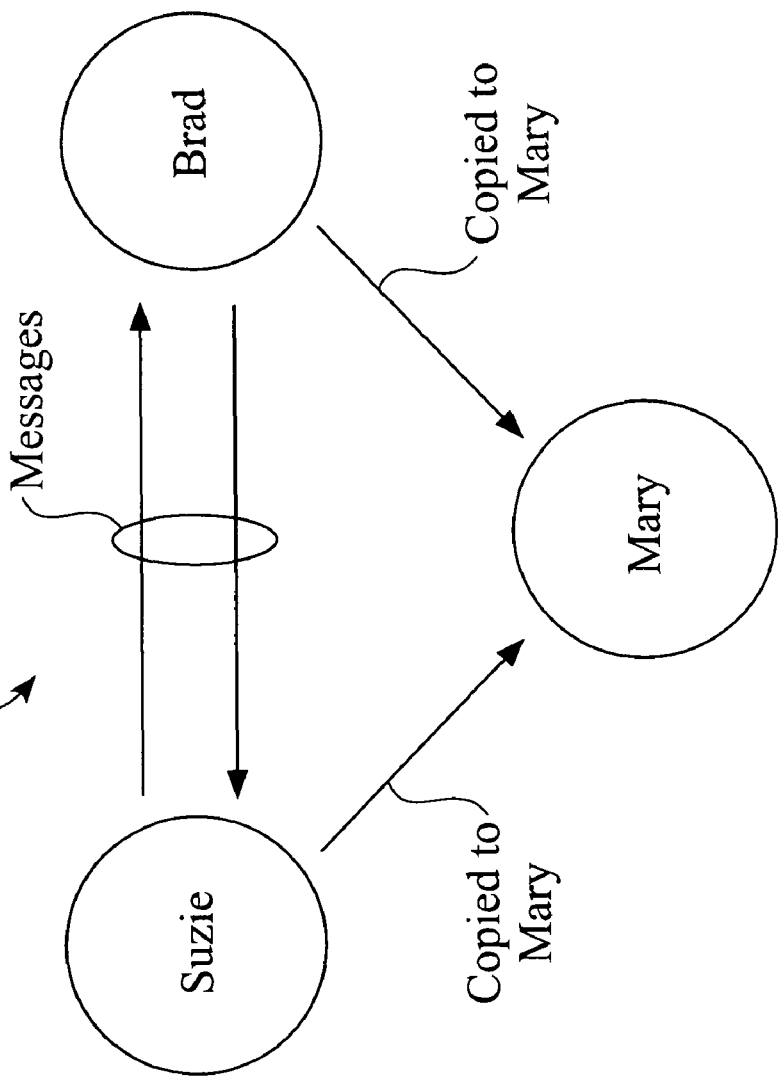

FIG. 67 reveals an alternative embodiment of the invention, which allows the original matchmaker to view the correspondence of her friends and their matches.

Figure 68:
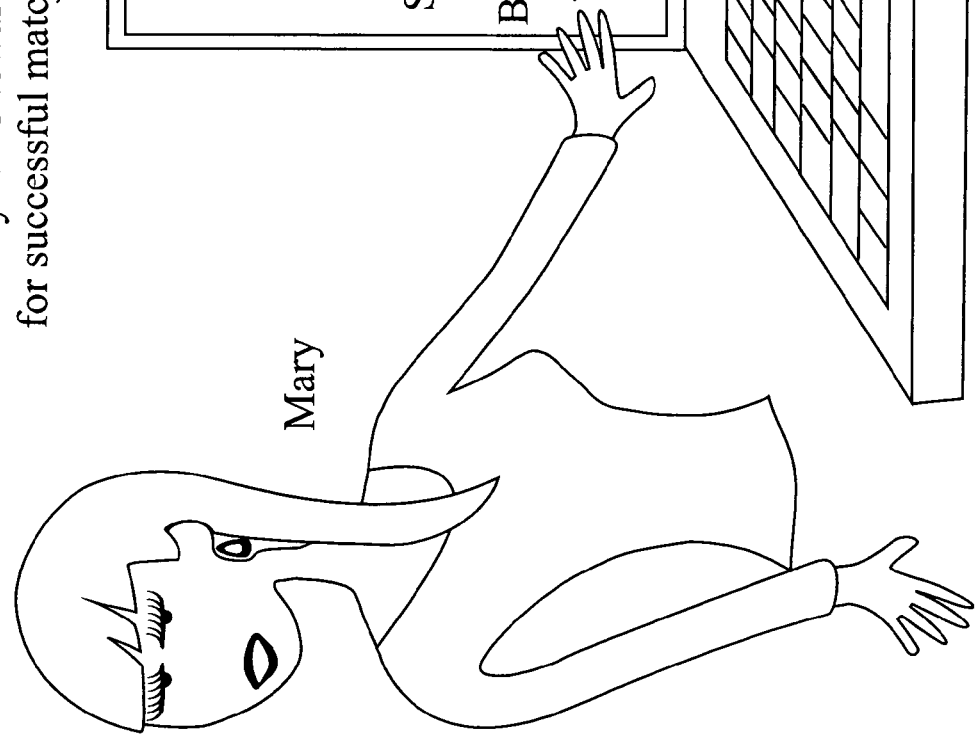

FIG. 68 shows how a matchmaker can earn rewards for making successful matches.

Figure 69:
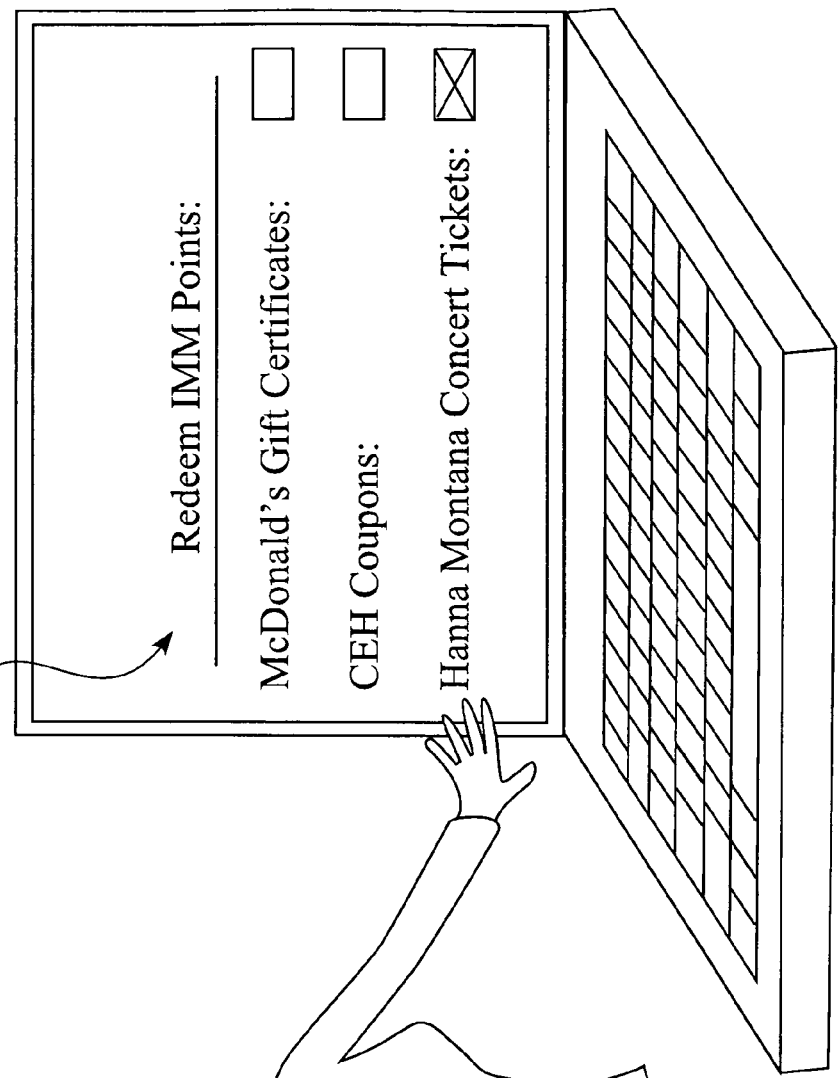

FIG. 69 explains how the Internet Matchmaker Club earns revenue by charging sponsors for advertising. Matchmakers may also use their credits to purchase goods and services offered by the sponsors.

FIG. 70 shows how a matchmaker can use her credits to pay for online dating and matching services.

A DETAILED DESCRIPTION OF PREFERRED & ALTERNATIVE EMBODIMENTS

I. Opening an Account, Obtaining a Test Kit and Submitting Attributes to an Internet Dating Service The present invention comprises methods and apparatus for predicting good relationships or matches. *Merriam-Webster's Online Dictionary* defines the word "relationship" as:

"1: the state of being related or interrelated, e.g., studied the relationship between the variables 2a: the relation connecting or binding participants in a relationship: as a kinship 2b: a specific instance or type of kinship 3a: a state of affairs existing between those having relations or dealings, e.g., had a good relationship with his family 3b: a romantic or passionate attachment"

In this Specification, and in the Claims that follow, the term "relationship" is used to connote a connection, association, affiliation or formal union between two persons. In particular, the relationships described and claimed in this Patent Application pertain to relationships which are premised, engendered or motivated by:

1. a correlation of self-describing attributes and the ideal-match attributes of another person; and
2. a first person's natural response to the genetic attributes of second person.

Figure 1:
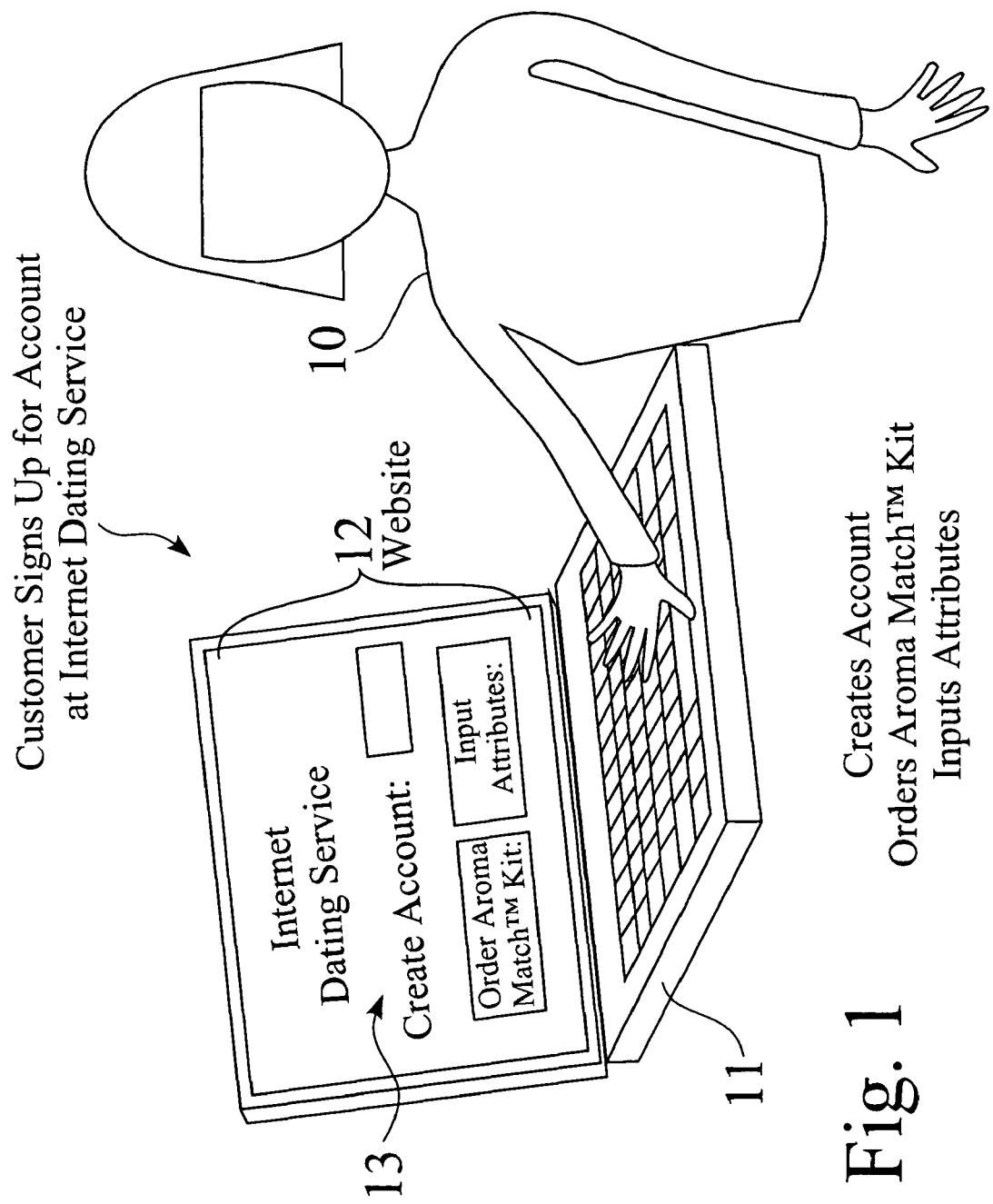
FIG. 1 shows a woman using a personal computer to sign up for an account with a Big Internet Dating Service, and then place an order for an AromaMatch™ Test Kit.
Figure 2:
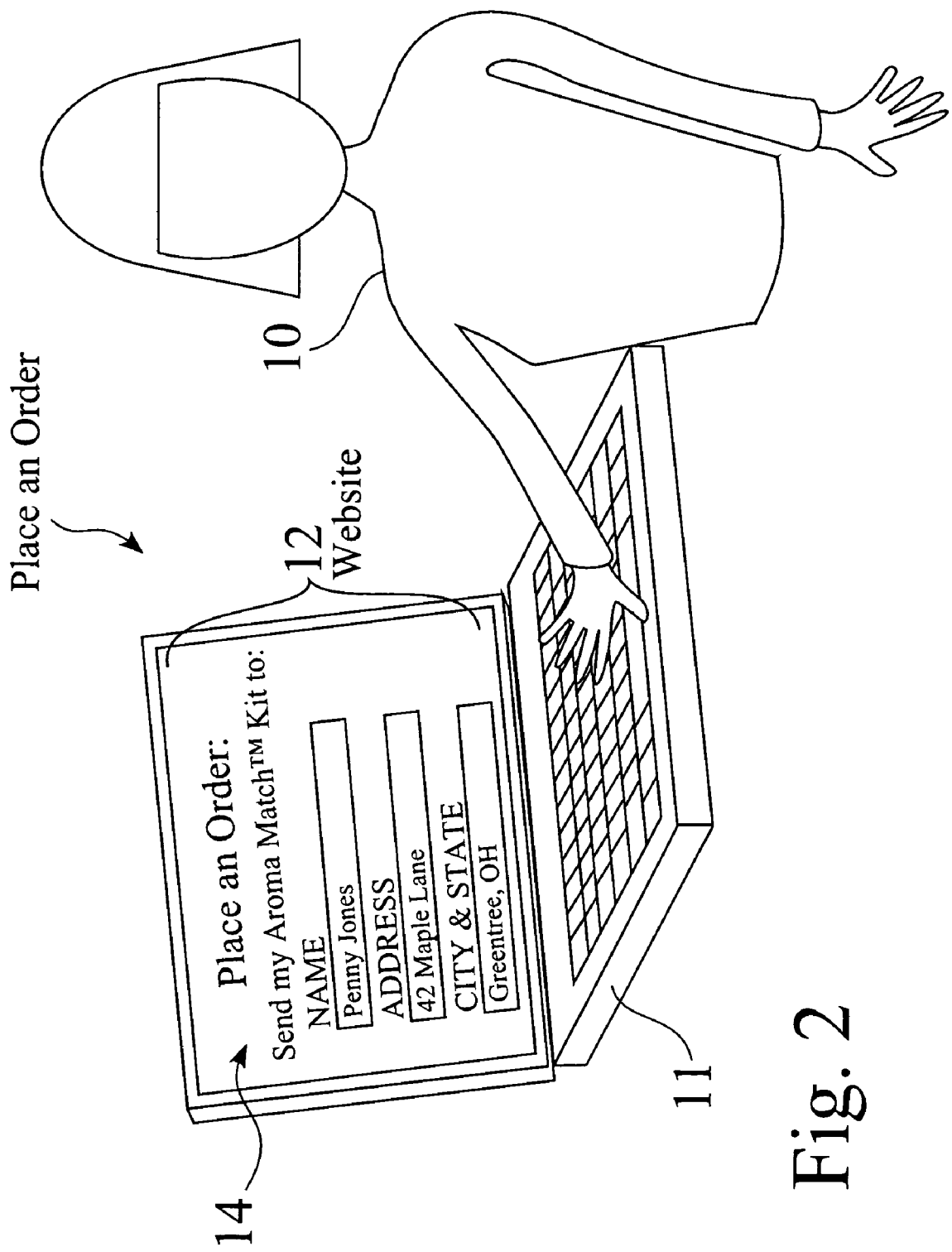
FIG. 2 shows a page from the Big Internet Dating Service website that may be used to place an order.

In one particular embodiment of the invention, the prediction of good relationships is predicated on a female's "responsivity." FIG. 1 shows a woman 10 using a personal computer, personal digital assistant, web-enabled cellular telephone or any other similar information appliance 11 to visit an Internet Dating Service 12 website. The view in FIG. 1 shows a web page 13 for opening a new account. Once the new account is established, the woman 10 proceeds to another page 14 on this website as shown in FIG. 2, which enables the woman 10 to place an order for an AromaMatch™ Test Kit 15. "AromaMatch" is a Trade & Service Mark owned by the Assignee of the Present Patent Application. The website "www.aromamatch.com" is also owned by the Assignee of the Present Patent Application. In one embodiment, the Test Kit 15 will be delivered to the customer 10 by the U.S. Mail, or a courier such as UPS™ or Federal Express®.

Figure 3:
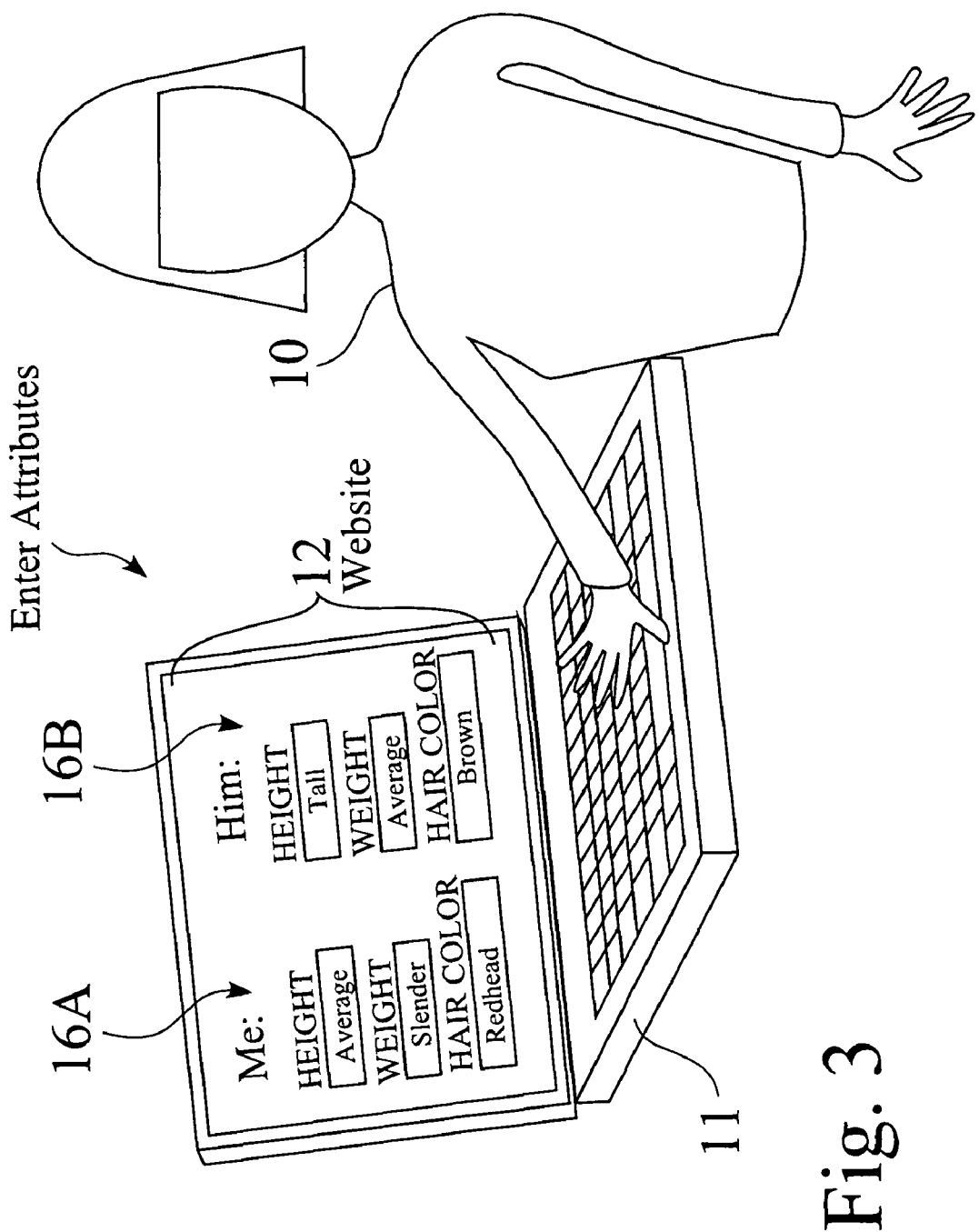
FIG. 3 shows a page from the Big Internet Dating Service that may be used to enter attributes about the customer and his or her ideal match.

FIG. 3 illustrates the same woman 10 entering attributes which describe herself 16A, as well as attributes which describe her perception of a good match 16B. These attributes 16A & 16B may describe physical characteristics, personality traits, educational levels, jobs or careers, personal goals, hobbies, activities or any other information that may provide a basis for predicting a good match.

Figure 4:
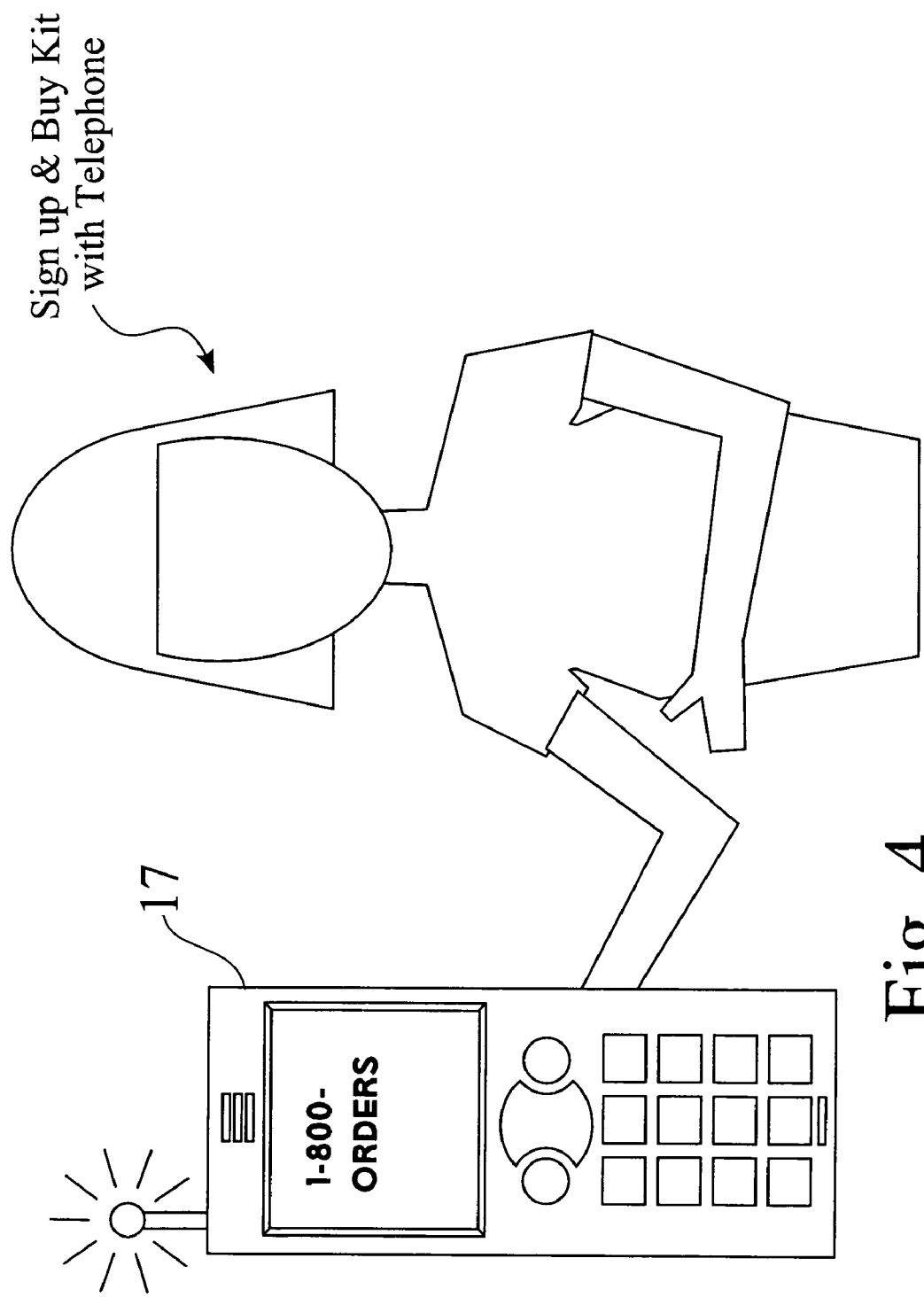
FIG. 4 shows an alternative embodiment of the invention, in which the woman uses a telephone to open the account and to place the order.

FIG. 4 depicts an alternative embodiment of the invention, in which the woman 10 uses a telephone 17 to open an account, place an order and/or submit attributes 16A and 16B to the Internet Dating Service over the phone.

Figure 5:
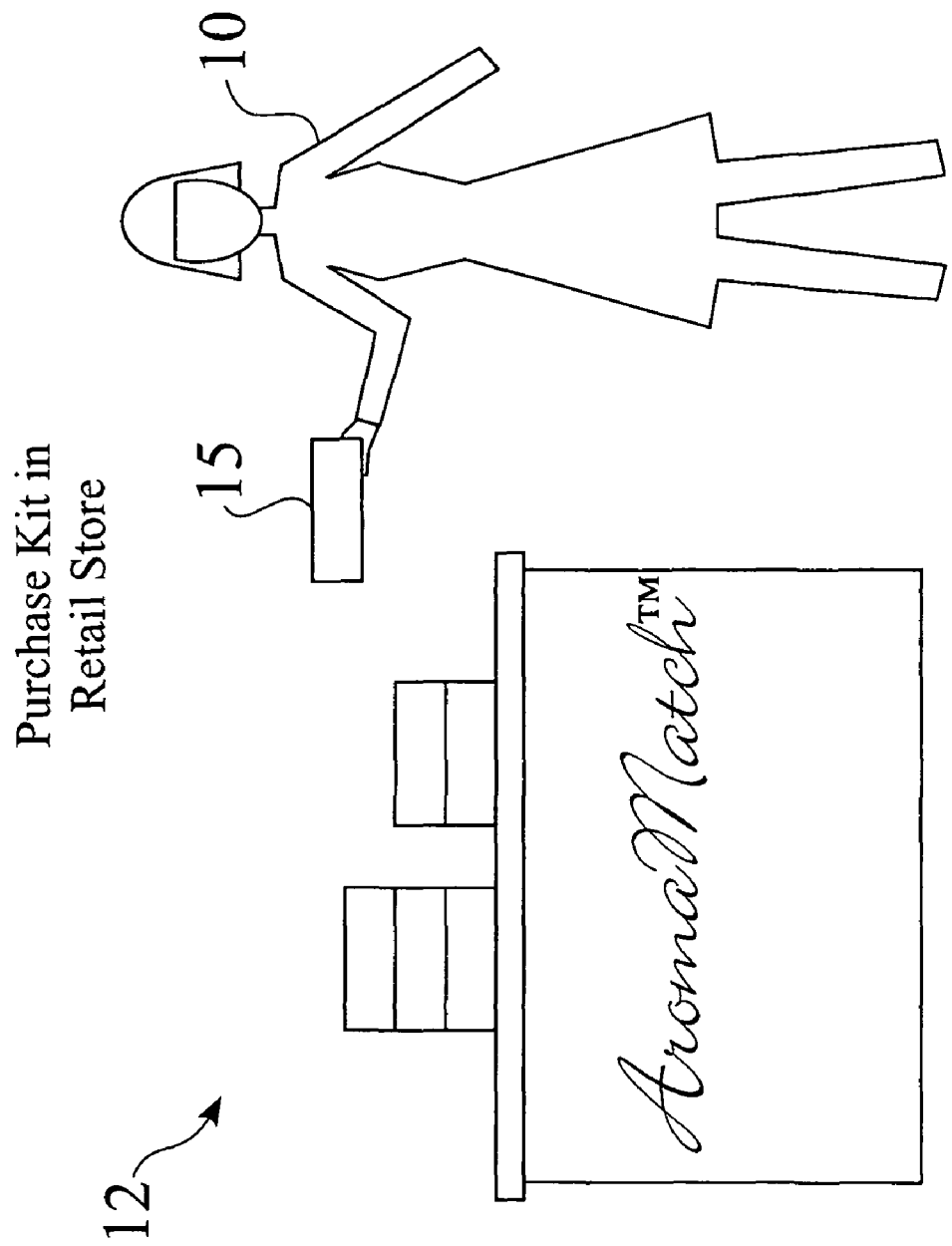
FIG. 5 shows a woman purchasing an AromaMatch™ Test Kit at a retail store.

FIG. 5 reveals another alternative embodiment, in which the woman 10 visits a retail store 18 to open an account, purchase a Test Kit 15, and/or fill out a questionnaire which furnishes attributes 16A and 16B to the Internet Dating Service 12, or other dating or introduction service.

Figure 6:
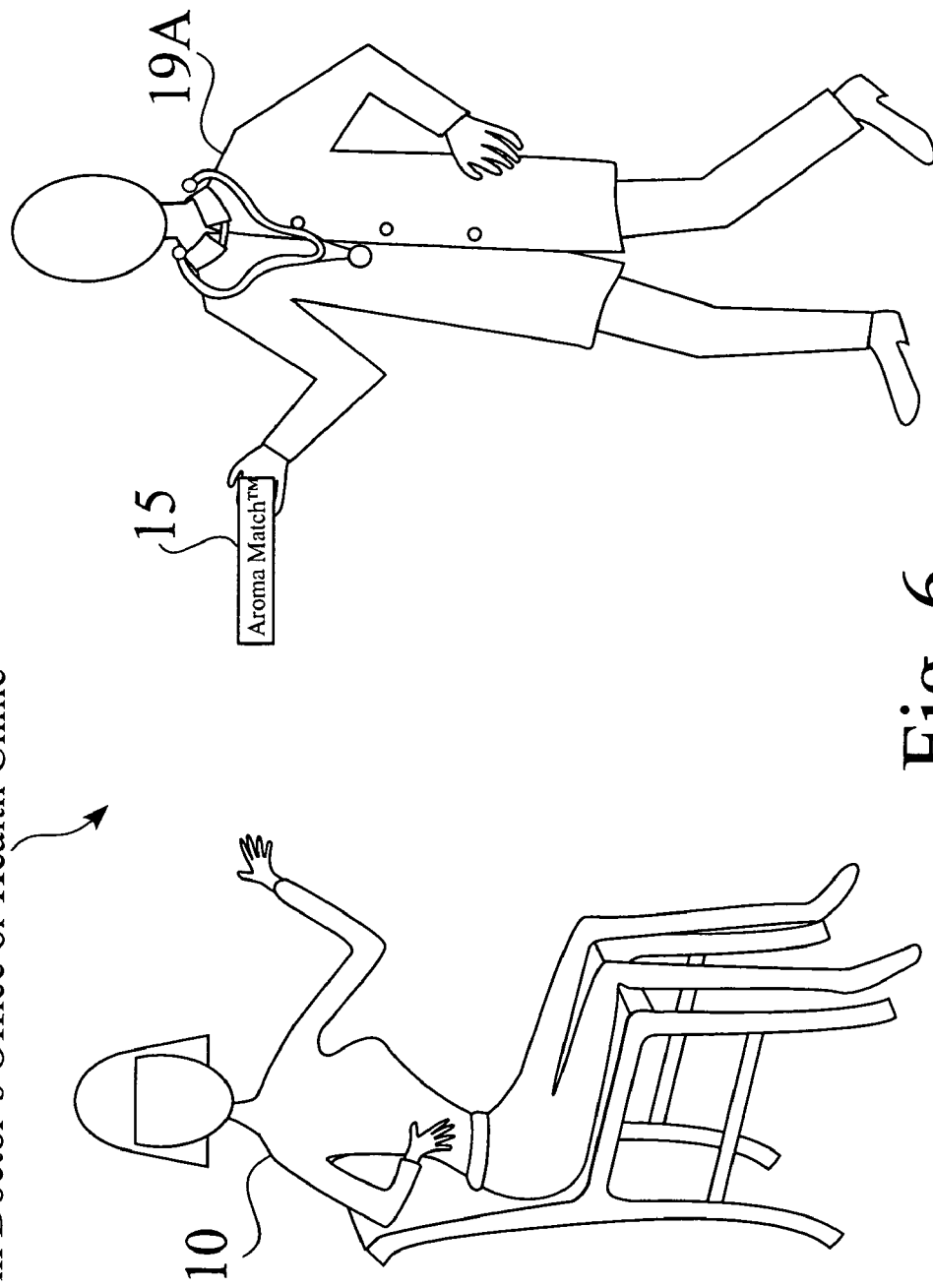
FIG. 6 shows a woman receiving an AromaMatch™ Test Kit in a doctor's office.

FIG. 6 supplies a view of yet another alternative embodiment of the invention, in which the customer 10 may open an account, purchase a Test Kit 15, and/or fill out a questionnaire to supply attributes 16A and 16B at a doctor's office or health clinic. The woman 10 may receive a Test Kit 15 from a physician, nurse, medical assistant or some other health care provider 19A. The customer 10 may provide her tissue sample while visiting the doctor's office, which is then certified by the doctor 19A before it is submitted to the laboratory. In this embodiment, the physician provides the Test Kit 15, and obtains the tissue sample. The physician 19A then sends the tissue sample to a laboratory for analysis, and also certifies that the sample is from a particular person. In this example, the physician acts as a "notary" who insures the identity of the source of the sample. This implementation of the invention guards against the fraudulent submission of a tissue sample from a person who might attempt to supply a misleading identity.

Figure 7:
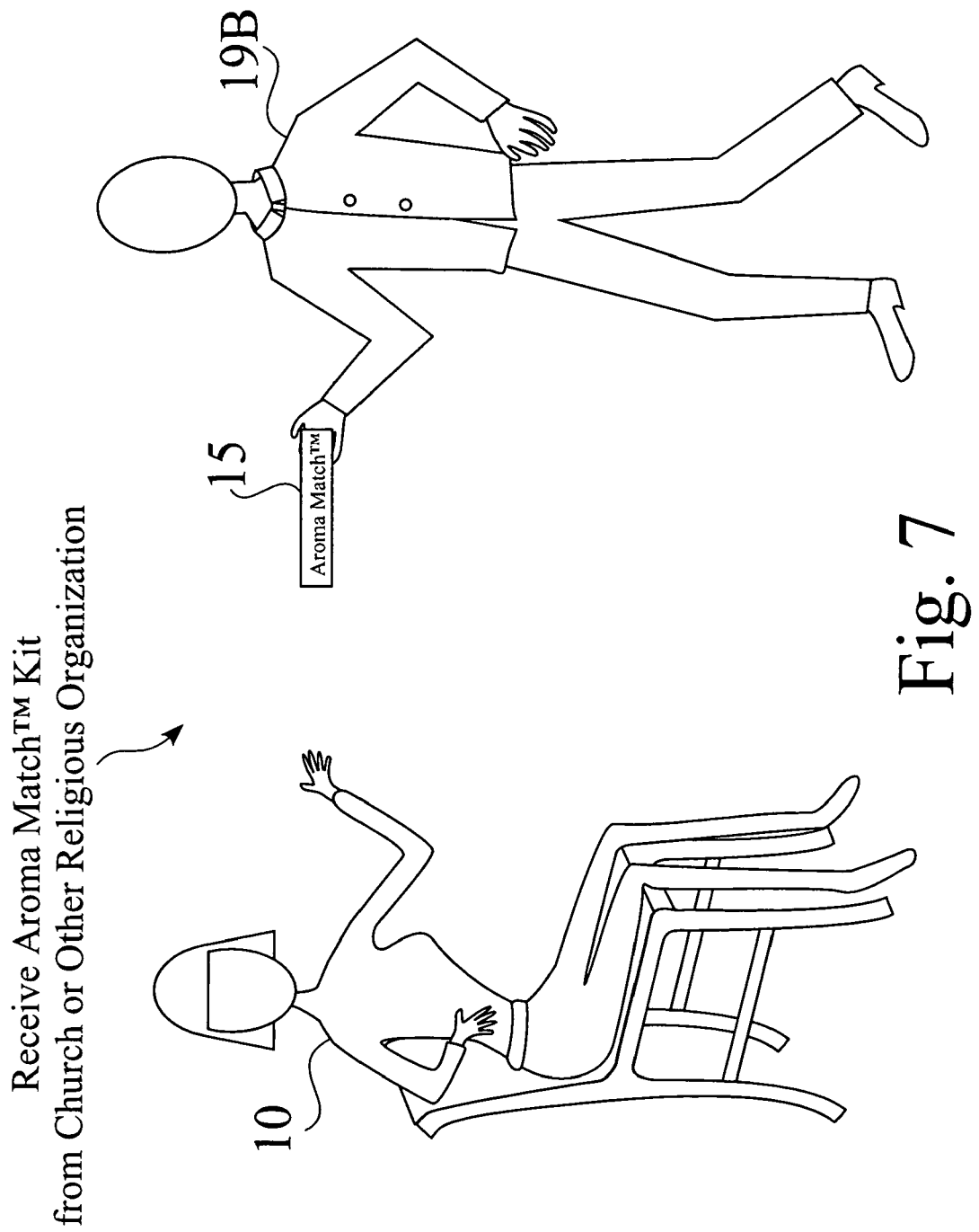
FIG. 7 shows a woman receiving an AromaMatch™ Test Kit from a church or some other religious organization.

In yet another embodiment, FIG. 7 shows the woman 10 receiving a Test Kit 15 from a priest, minister, rabbi or some other religious leader or cleric 19B. In one embodiment, the invention is promoted by a religious or spiritual organization to promote good relationships and/or marriages.

In one embodiment of the invention, customers visit a website to supply information about themselves, and their ideal match. In this implementation of the invention, information is stored electronically in a computer database. In alternative embodiments, information about customers and their test results may be recorded in some other form of database, whether in electronic, paper or other means of media or storage.

In yet another embodiment of the invention, this database of information and/or records may be maintained by an introduction service, which may include a dating or matching service, or some other means for enabling, furnishing or assisting people find romantic or other matches. The introduction service may or may not utilize the Internet and/or electronic record keeping.

II. The AromaMatch™ Test Kit

Figure 8:
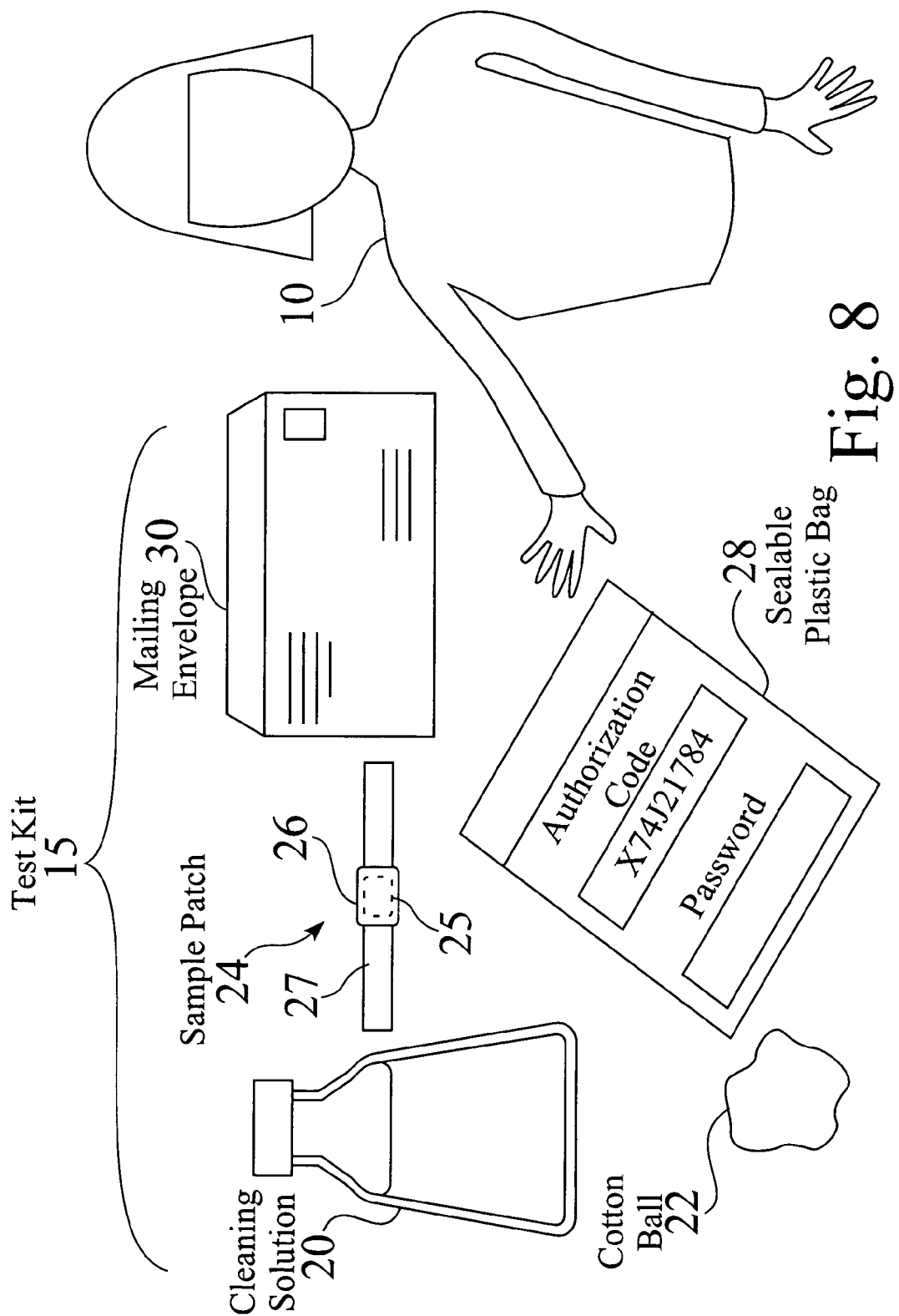
FIG. 8 depicts the woman opening the AromaMatch™ Test Kit to reveal its contents: a bottle, a cotton ball, a sample patch, a sealable plastic bag and a mailing envelope.

FIG. 8 portrays the woman 10 opening and removing the contents of the AromaMatch™ Test Kit 15. In one embodiment of the invention, the Test Kit 15 comprises:
cleaning solution or skin cleaner 20;
a cotton ball or other cleaning medium 22;
an odor-absorbing sample patch 24, which includes a portion of plaster 25 coated with an antibiotic 26 and portions coated with a skin adhesive 27;
a sealable enclosure 28, such as an envelope or bag; and
a mailing or shipping envelope or pouch 30.

The skin cleaner 20 may comprise a liquid cleaning solution such as isopropyl alcohol, or any other, gel, solid, spray or substance that cleans and/or sterilizes a portion of the skin. The application of the skin cleaner 20 removes or neutralizes perfumes and other irrelevant smells.

The cleaning medium 22 is generally a small portion of material that is used to apply the skin cleaner 20 to the skin. In one embodiment, the cleaning medium 22 may be a cotton ball, wad, paper, piece of fabric or some other suitable application device.

FIG. 9 furnishes an illustration of the sample patch 24, which comprises a small central area 24C with two outwardly extending strips 24S. The central area 24C is coated with a portion of plaster 25 which, in turn, has been coated with an antibiotic 26 or some other suitable agent that prevents bacterial growth which might modify the aroma. The strips 24S on either side of the plaster 25 are coated with an adhesive 27 that is suitable for adhering to the skin for a short period of time. Either side of the patch 24 may be coated with adhesive.

In one embodiment, the patch 24 resembles a conventional "Band-Aid® Brand" Adhesive Bandage, such as that manufactured and sold by Johnson & Johnson of New Brunswick, N.J. The patch 24 may be fabricated from plastic, cloth, paper or any other material that will maintain the plaster 25 in generally continuous contact with the skin. The plaster 25 is generally any material that will absorb and then hold an aroma which has been secreted by the skin. The plaster 25 may be composed of any substance that collects and stores an aroma. In this Specification and in the Claims that follow, the term "aroma" encompasses any scent, smell, odor or olfactory component that may or may not be actively or consciously detected, sensed or smelled by a person. In one embodiment of the invention, the plaster 25 is manufactured from any material that may be used as an odor-absorbing poultice.

The plaster 25 is designed so that it will collect enough aromas to provide a sample which may be reliably analyzed. The aromas captured by the plaster 25 must be able to survive for a duration of time that is required for the patch 24 to be mailed to a laboratory.

After the Test Kit 15 is opened, the woman 10 cleans a patch of skin on her arm in preparation for applying the sample patch 24, as shown in FIG. 10. In a preferred embodiment, the patch is placed on the armpit. In FIG. 11, patch 24 has been attached to her skin. The patch 24 may be worn on any portion of the body which allows direct and intimate contact with the skin, and which enables a sufficient collection of body odor.

The woman wears the patch 24 all day, as shown in FIG. 12. The time that is required for the patch 24 to remain in place varies with the effectiveness of the plaster 25 and the sensitivity of the equipment used to analyze the patch 24. In one embodiment of the invention, the user is instructed to leave the patch 24 in place on the skin for at least eight hours. In some instances, the time that is required to wear to patch to obtain a good sample may take longer. One alternative method that may be used to collect a sample is using a simply wearing a shirt or some other article of clothing for an extended time, and then analyzing this worn article of clothing.

After wearing the patch 24 all day, the woman 10 removes the patch 24 later that evening, as shown in FIG. 13. After the patch 24 is removed, she then immediately places the patch 24 in the enclosure 28, as illustrated in FIG. 14. The enclosure is sealed 28 to prevent any degradation of the aromas stored in the plaster 25.

She then writes her username, password, code or some other identifying information on the bag 28, as shown in FIG. 15. This enclosure 28 is large enough to hold the sample patch 24, may be easily sealed against the intrusion of outside air by the user, and is generally an impermeable container or barrier that preserves the aromas imparted to the plaster 25 on the patch 24. In one embodiment of the invention, the enclosure 28 is a plastic bag with a compression seal, which is commonly known as a "zip-lock" or "slide-lock" closure. In one implementation, the bag 28 bears a pre-printed authorization code.

The patch 24 which stores the odor sample which has been sealed in the bag 28 is then placed in the mailing envelope, as shown in FIG. 16.

FIG. 17 portrays the customer posting the pre-addressed mailing envelope 30 which contains the worn patch 24 in the bag 28. This envelope 30 will convey the patch 24 to a laboratory where the plaster 25 will be analyzed. As an alternative, the patch 24 may be shipped to a laboratory using a courier. The patch 24 may also be delivered to a local laboratory, doctor's office or pharmacy for analysis. In a more advanced embodiment of the invention, the user may analyze the patch 24 using a home analysis kit.

FIG. 18 shows a laboratory technician 32 using an analyzer 34 to determine the genetic attributes of the tissue sample that has been received from the customer 10. In one embodiment, a probe from an analyzer 34 may be inserted into the bag 28, which will convey the aromas to a chamber where a chemical analysis is conducted.

Several devices and systems for analyzing a sample are currently available which may be used to implement the present invention. One device called an "Electronic Nose" has been described by The Lewis Group of The California Institute of Technology, and is based on readily fabricated, chemically sensitive conducting polymer films. According to information presented on their website:

"An array of sensors that individually respond to vapors can produce a distinguishable response pattern for each separate type of analyte or mixture. Pattern recognition algorithms and or neural network hardware are used on the output signals arising from the electronic nose to classify, identify, and where necessary quantify, the vapor or odors of concern. This response is much like the way the mammalian olfactory sense produces diagnostic patterns and then transmits them to the brain for processing and analysis.

"This approach does not require development of highly specific recognition chemistries, one for each of the many possible analytes of interest. Instead this approach requires a broadly responsive array of sensors that is trainable to the target signature of interest and then can recognize this signature and deliver it to the sensing electronics in a robust fashion for subsequent processing by pattern recognition algorithms. The Caltech electronic nose functions at atmospheric pressure, functions in a variety of ambients, exhibits near-real time detection, and has already been demonstrated to track vapors in air.

"The underlying principle of the Caltech electronic nose is extraordinarily simple. When a polymer film is exposed to a gaseous vapor, some of the vapor partitions into the film and causes the film to swell. In the electronic nose, this swelling is probed electrically because the sensor films each consist of a composite that contains regions of a conductor that have been dispersed into the swellable organic insulator. The vapor-induced film swelling produces an increase in the electrical resistance of the film because the swelling decreases the number of connected pathways of the conducting component of the composite material. The detector films can be formed from conducting polymer composites, in which the electronically conductive phase is a conducting organic polymer and the insulating phase is an organic polymer, or from polymer-conductor composites in which the conductive phase is an inorganic conductor such as carbon black, Au, Ag, etc and the insulating phase is a swellable organic material. The electrical resistance of the device is then read using simple, low power electronics.

"Any individual sensor film responds to a variety of vapors, because numerous chemicals will partition into the polymer and cause it to swell to varying degrees. However, an array of sensors, containing different polymers, yields a distinct fingerprint for each odor because the swelling properties over the entire array are different for different vapors. The pattern of resistance changes on the array is diagnostic of the vapor, while the amplitude of the patterns indicates the concentration of the vapor."

See: The Lewis Group, California Institute of Technology, Pasadena, Calif.

A second device that may be used to implement the present invention is called the "Cyranose," and is described by Rodney M. Goodman, in his article entitled "The Electronic Nose." According to Goodman:

"The technology uses sensors mixed with carbon black to make them conductive. The polymers swell with an odorant and their resistance changes. An array of different polymers swell to different degrees giving a signature of the odorant. This technology has been commercialized by Cyrano Sciences and a handheld electronic nose has been launched as a product."

A third device that may be used to implement the present invention is described by Smiths Detection of Danbury, Conn., which produces and sells devices for identifying materials.

In FIG. 19, the customer 10 uses her computer 11 to visit the Internet Dating Service website to obtain the results of the laboratory analysis 35. In one embodiment, the analysis includes a listing of MHC alleles, MHC-determined peptides, MHC-odors or some other MHC-dependent profile. In an alternative embodiment, the results may be dispatched to the customer by regular mail or by e-mail.

In an alternative embodiment of the invention, the customer pays for the Test Kit 15 and the analysis when he or she obtains the results of the analysis.

In FIG. 20, the website reports the results 36 of a matching process that has been performed by comparing the customer's attributes to the attributes of a library of candidates. In one embodiment of the invention, the matching process correlates the set of self-describing attributes and the set of ideal-match attributes provided by the customer. Examples of attributes are supplied in Table One:

TABLE ONE

| Category | Examples of Attributes |
| --- | --- |
| Gender | Male, Female |
| Age | |
| Appearance | Handsome/Knockout, Attractive/Cute |
| Marital history | Single, Divorced |
| Residence location | |
| Height | Tall, Average, Short |
| Weight | |
| Hair Color | Blonde, Brunette, Redhead |
| Occupation & Income | |
| Religiosity | Yes/No; Denomination |
| Political preferences | Conservative, Liberal, None |
| Interests or hobbies | |
| Educational level | |
| Social Class Marker | |

The correlation process may involve comparing responses to individual preferences or predilections, or may involve more complex matching methods, such as those described in related U.S. patent application Ser. No. 11/881,153, entitled Searching Methods, which was filed on 24 Jul. 2007.

In FIG. 21, the customer 10 is shown receiving her test results 36 from a postal worker 38, while FIG. 22 shows the customer 10 receiving her test results 37 from a physician or other health care worker 19A in a doctor's office or clinic.

FIG. 23 reveals yet another alternative embodiment, in which a tissue sample 40 is obtained using a cheek swab. In other embodiments, a tissue sample may be obtained from any suitable bodily material or fluid, including, but not limited to, blood, saliva, exhaled breath, fingerprint, urine, hair, nail, or skin. One device that may be used to implement this portion of the present invention is produced and sold by DNA Genotek of Ottawa, Ontario, Canada, which produces and sells the Oragene™ DNA Self-Collection Kit, for collecting and preserving large amounts of DNA from saliva.

FIG. 24 exhibits an alternative embodiment, which collects a sample directly from the air 46 surrounding a customer 10 standing near a kiosk 44 that has been installed in a shopping mall 42. In yet another embodiment, a sample collecting tube may briefly be placed under a portion of a customer's clothing to obtain an air sample.

In an alternative embodiment of the invention, an automatic machine or device which accepts a DNA sample may be used to obtain an analysis without the intervention of a technician or clerk.

III. One Specific Embodiment for Obtaining a Sample: Collection of Saliva

In one particular embodiment of the present invention, the customer 10 provides a saliva sample for analysis by a laboratory. FIG. 25 depicts the collection of a saliva sample 48 in a disc-shaped container or cup 50. In FIG. 26, a cap 54 is screwed on to the cup, and the sample is mixed 52. FIG. 27 illustrates the step 56 of placing the closed cup in a sample bag 28, and the bag 28 is sealed. FIG. 28 shows the step 58 of placing the sample bag 28 in a mailing box 30. FIG. 29 depicts the step 60 of sealing the mailing box, and FIG. 30 depicts the step 62 of mailing the box 30. More details concerning particular embodiments of sample collection and analysis that may be used to implement the present invention may be found by visiting the website for DNA Genotek, Inc. of Ottawa, Ontario, Canada.

The present invention may be implemented by obtaining any sample from a customer which may be analyzed to determine genetic characteristics.

IV. Business Methods: Predicting a Good Match

FIG. 31 is a flow chart which illustrates laboratory collection kit preparation tasks.

FIG. 32 is a flow chart which illustrates dating service tasks.

FIG. 33 is a flow chart which illustrates customer tasks.

FIG. 34 is a flow chart which illustrates laboratory analysis, matching and reporting tasks.

FIG. 35 is a flow chart which illustrates dating service and laboratory cooperative tasks.

V. MHC Biology

FIG. 36 is a graph which plots experimentally measured human female sexual responsivity to another person on the y-axis, and the number of MHC alleles shared with that other person on the x-axis. The graph shows that a woman's sexual response, or responsivity, to a man is much higher if the man has MHC alleles which are different from her own. The greater the dissimilarity, the greater her response. The highest responsivity occurs when the proportion of shared MHC alleles is zero percent, while the lowest responsivity occurs when the proportion of shared MHC alleles approaches seventy percent.

FIG. 37 depicts similar experimentally measured data in the form of a bar chart, and shows an expected female sexual responsivity to a partner along the y-axis, and the number of shared MHC alleles on the x-axis.

After a sample that has been obtained from a customer is received at a laboratory, the sample is processed to extract DNA. DNA is the chemical inside the nucleus of a cell that carries the genetic instructions for making living organisms. A cell is the basic unit of any living organism. It is a small, watery, compartment filled with chemicals and a complete copy of the organism's genome. Each cell contains a nucleus, which is the central cell structure that houses the chromosomes. Chromosomes are one of the threadlike "packages" of genes and other DNA in the nucleus of a cell. Chromosomes enclosed within the nucleus, which is, in turn, enclosed in the center of the cell.

Different species have different numbers of chromosomes. Humans have twenty-three pairs of chromosomes, forty-six in all: forty-four autosomes and two sex chromosomes. Each parent contributes one chromosome to each pair, so children get half of their chromosomes from their mothers and half from their fathers.

Part of the chromosome is called a gene. The gene is the functional and physical unit of heredity passed from parent to offspring. Genes are pieces of DNA, and most genes contain the information for making a specific protein.

A strand of DNA comprises a pair of helical ribbons attached by bases that resemble the rungs of a ladder. These bases are named adenine, thymine, guanine and cytosine. Sometime uracil is substituted for thymine. A section of one of the spiral sides of the DNA together with one of the bases comprises a nucleotide. Nucleotides are one of the structural components, or building blocks, of DNA and ribonucleic acid (RNA). A nucleotide consists of a base (one of four chemicals: adenine, thymine, guanine, and cytosine) plus a molecule of sugar and one of phosphoric acid.

Another set of chemicals that are important building blocks in humans are amino acids. Amino acids are the "building blocks" of proteins. There are twenty different kinds of amino acids in the human body. When two or more amino acids are bonded together, they form a peptide.

An allele is one of the forms of a gene at a particular location or "locus" on a chromosome. Alleles are specific sequences of base pairs that can be present at a given locus. For example, at the HLA-A locus in a particular individual, alleles in the A*01 and A*02 groups may be found. The "*" in the allele group name indicates that it was determined by DNA typing, as opposed to serological methods.

Different alleles produce variation in inherited characteristics such as hair color or blood type. In an individual, the dominant form of the allele is expressed, while the recessive form is not expressed. An exception to this rule is the case in which the genes at a particular locus are expressed codominantly, in which case they are both expressed.

In accordance with the present invention, small amounts of DNA are obtained from the sample submitted to a laboratory by a user who has submitted a saliva sample or skin scraping. In one embodiment of the invention, personnel at the laboratory cut the sample using a punch to make three separate disc-shaped pieces. These pieces are each placed in a different test tube. All the pieces are washed several times with chemicals that purify the sample on each piece. After washing, each piece is dried in its tube.

In an alternative embodiment, if a saliva sample is obtained from the customer, the saliva is poured directly into three separate test tubes, washed and then the DNA analysis is performed.

When DNA is analyzed, a laboratory technician looks at particular places or "loci," (which are the positions in a chromosome in which specific genes are known to occur) to determine the particular allele (variation of the gene). Previous research has determined that every person has a characteristic sequence of genetic material (allele) that resides at each of his or her genetic loci.

The laboratory technician basically examines particular sets of alleles that are found at a particular group of loci on a particular chromosome. To match alleles in the MEC region of the genome, the technician "takes an inventory" of the genetic material in the MHC region on Chromosome 6. Parts of the MHC are broken down into smaller groups of genetic material, and are given names. In one embodiment, the parts of the MHC that need to be inventoried are named "HLA-A," "HLA-B" and "HLA-DRβ1." These parts of the MHC are on a particular region of a particular chromosome. All these relationships 78 are illustrated in FIG. 38.

The term "allele groups" are also known as "2-digit alleles" and "2 alleles." "High resolution alleles" are also known as "4-digit alleles" and "4 alleles."

There are 21 HLA-A allele groups, 37 HLA-B allele groups, and 13 HLA-Dβ1 allele groups. The various MEG Allele Groups 80, such as "A*01," "A*02" and "A*03" are presented in FIG. 39. FIG. 40 depicts HLA-A Allele Group Frequency 82. FIG. 41 depicts HLA-B Group Frequency 84. FIG. 42 depicts HLA-DRβ1 Group Frequency 86. FIG. 43 depicts Allele Group Frequencies 88. FIG. 44 depicts A/B/DRβ1 Group Haplotype Frequency 90.

The sequence-specific oligonucleotide probe (SSOP) method is used. The basis of this method is HLA locus-specific amplification by polymerase chain reaction (PCR), and the subsequent probing of the resulting product by SSOP. A battery of probes is required. The pattern of reaction to these probes distinguishes the HLA alleles.

For each sample, the laboratory uses PCR for HLA locus-specific amplification at HLA-A, HLA-B, and HLA-DRβ1. Each of the three PCR amplifications results in a product. Each of the three products is then tested with a battery of probes. The HLA-A amplified product is tested with 12 probes at exon 2 and 16 probes at exon 3. The HLA-B amplified product is tested with 18 probes at exon 2 and 18 probes at exon 3. The HLA-DRβ1 amplified product is tested with 25 probes at exon 2. These are sufficient numbers of probes so that the reaction patterns will distinguish the HLA allele groups (2-digit alleles), for example, A*02.

After all the genetic codes that are contained on a sample piece is identified, this information is entered into a database along with the personal information and match preferences of the customer who submitted the sample.

Previous scientific research has determined that a woman's attraction to a particular man and her sexual response to him is based on the correlation between the alleles in the woman's MHC, and in the man's MHC. Specifically, a woman and a man who have different MHC genetic codes are more sexually compatible than a man and a woman who have similar MHC genetic codes.

So, when the lab technician takes an inventory of all the different allele groups (2-digit alleles) in a user's DNA sample, the technician is creating an identification or map of the person who submitted the sample. By comparing this identification or map with that of a different person, a technician can predict which other people will be attractive and sexually responsive to the customer, all based on the genetic code of each individual. In addition to the HLA-A, HLA-B and HLA-DRβ1 loci specified above, genetic information from other loci on Chromosome 6 or any other chromosome may be used to enhance a match.

In alternative embodiment of the invention, genetic attributes are determined by analyzing serologically typed HLA antigens. While "allele groups" are determined by genetic testing, such as PCR-SSOP, HLA antigens are determined by serological, or blood reaction, testing. Serological typing provides approximately the same resolution as "2-digit alleles." It cannot provide the higher resolution comparable to "4-digit alleles."

More detailed information concerning this analysis may be found in *Methods in Molecular Biology, Vol.* 210: *MHC Protocols*, edited by S. H Powis and Robert W. Vaughan, Humana Press Inc., Totowa, N.J., 2003. (See Chapter 5, "PCR-Sequence-Specific Oligonucleotide Probe Typing for HLA-A, -B, and -DR, by Derik Middleton and F. Williams). Another useful publication is *Histocompatibility Testing*, edited by Jeffrey L. Bidwell and Cristina Navarrete, Imperial College Press, 2000. (See Chapter 6, "PCR-SSOP Typing" by D. Middleton.) These publications explain how to type the MHC loci of interest using a two-tier system. The first level of resolution determines the allele group (2-digit alleles), and the second level uses this knowledge to determine the allele subgroup (4-digit alleles). Alleles in the MHC region may also be identified by the antigens produced by the proteins manufactured in the cells, using the "blueprint" provided by the allele. These Human Leucocyte Antigens (HLAs) may be typed by the complement-dependent lymphocytotoxicity.

HLA typing can be performed by the complement dependent lymphocytotoxicity reaction (serology). Live peripheral blood mononuclear cells are required for this assay (CD8+ T-cells and/or CD19+). B-cells are purified from whole blood, and incubated against a panel of antibodies with specificity against polymorphic epitopes expressed on HLA-A and -B proteins. In the presence of complement cells expressing HLA proteins which react with a particular antibody are lysed, allowing these damaged cells to uptake a stain which is detected by fluorescent microscopy. The pattern of negative and positive reactions is scored and interpreted to give an HLA serological type. HLAs may also be identified by their odor, and it is this method that humans and other mammals use for mate selection and personal identification, and by the electronic odor sensing process described above.

Additional information concerning HLA analysis may be found in *Histocoinpatibility Testing*, edited by Jeffrey L. Bidwell and Cristina Navarrete, Imperial College Press, 2000. (See Chapter 1, "HLA Typing by Alloantibodies and Monoclonal Antibodies" by G. M. Th. Schreuder; and Chapter 2, "Screening for HLA-Specific Antibodies" by C. Brown and C. Navarrete.) These publications explain how to type the MHC loci of interest using antibody reactions.

As genome sequencing has become less expensive, there has been a great deal of interest in pairing variations in certain genes with variations in behavior ("Molecular Psychiatry"). This science is still young: the following are recent discoveries. This invention can be used to refine its relationship-predicting service by including some or all of these genetic loci:

The brain neuropeptide arginine vasopressin (AVP) is a pituitary hormone which regulates blood pressure and kidney function in mammals. Studies of voles (one of the few non-human mammals that exhibit pair-bonding) found that AVP exerts a strong influence on their pair-bonding. This work has recently been extended to humans, and has revealed an association between one of the alleles of the AVPR1a gene (this gene codes for cellular receptors for AVP) and traits reflecting pair-bonding behavior in men, including partner bonding, perceived marital problems and marital status. The study also shows that it affects marital quality as perceived by their spouses. See Walum, Hasse et al., "Genetic variation in the vasopressin receptor 1a gene (AVPR1a) associates with pair-bonding behavior in humans," Proceedings of the National Academy of Sciences, Vol. 105, No. 37, Sep. 16, 2008).

Oxytocin is a hormone " . . . which seems to modulate a wide range of sexual and social behaviors from social recognition, pair bonding, mate guarding and parental care in rodents, to love, trust or fear in humans." Certain alleles of the CD38 gene lead to impaired nurturing behaviors, social amnesia (failure to recognize others) and is suspected of causing " . . . some forms of impaired human behavior in the spectrum of autism disorders." See Jin, Duo et al., "CD38 is critical for social behavior by regulating oxytocin secretion," Nature, Vol. 446, pp. 41-45 (2007).

Variations in a dopamine receptor gene (DRD4, on Chromosome 11 in humans) contribute to individual differences in human sexual behavior: desire, arousal and sexual function, and in particular predicts overall sexual interest. Studies that have shown this effect in animals have now been extended to humans and show similar results. See Ben Zion, I Z, et al., "Polymorphisms in the dopamine D4 receptor gene (DRD4) contribute to individual differences in human sexual behavior: desire, arousal and sexual function," Molecular Psychiatry Vol. 11, pp. 782-786 (2006), and Pearson, Helen, "Sexual desire traced to genetics," Nature Online, doi:10.1038/news060529-6 (Published online 31 May 2006).

Recently-published work finds that variations in the ER (Chromosome 6) locus predict psychoticism, neuroticism, non-conformity and extraversion in women, including sexual behavior. See Westberg et al., Association between a dinucleotide repeat polymorphism of the estrogen receptor alpha gene (ERα) and personality traits in women, Molecular Psychiatry 8, Pages 118-122 (2003).

A more detailed description of matches using the information obtained by analyses of MHC, HLA and other genome loci such as those described above, as well as the Attributes listed in Table 1, may be found in a related Pending U.S. patent application Ser. No. 11/514,285, entitled Matching System, which was filed on 30 Aug. 2006.

VI. Finding Good Matches with a MateFinder™

FIG. 46 shows the step 94 of a customer using a MateFinder™ device 96 which has been programmed with his genetic attributes, as determined in accordance with the present invention. FIG. 47 offers a detailed view of one embodiment of a MateFinder™ device 98.

In one particular embodiment, the MateFinder™ comprises a radio and a microprocessor with a non-volatile memory, such as a static random-access memory (RAM). Information that describes both the user and the ideal match can be written to the non-volatile memory. The radio automatically and periodically broadcasts a "seeking signal" over a short range. When the seeking signal is received by another MateFinder™, it is analyzed to determine the degree of correlation with the receiver's preferences. If the degree of correlation exceeds a preset minimum, the sender, the receiver, or both are alerted.

Another embodiment combines the MateFinder with a network radio or device, such as a cellular or Voice over Internet Protocol (VoIP) telephone or some other suitable device to provide communications over a wireless network. This combination enables voice calls, text-messaging, instant messaging, e-mails and Internet browsing. The user may also arrange to transfer gifts of music, photographs, video clips and other matter purchased from a third party. The MateFinder may be connected to a network using Wi-Fi, Wi-MAX, UltraWide Band (UWB) radio or any other suitable wireless system. The MateFinder may also communicate over a wired network such as the conventional telephone network, the Internet or may use VoIP.

In another embodiment of the invention, the MateFinder is programmed with information concerning the genetic attributes of a number of individuals. Romantic matches are suggested by correlating the genetic attributes of different individuals. These genetic attributes are first determined by testing tissue or fluid samples.

A more detailed description of this aspect of the present invention may be found in a related Pending U.S. patent application Ser. No. 11/514,285, entitled Matching System, which was filed on 30 Aug. 2006.

VII. Benefits of the Invention

Reducing Consanguinity

The present invention includes a method for selecting candidates for a relationship based on diversity in the Major Histocompatibility Complex (MHC) region of their genomes. This method of the invention reduces the risk of couples' producing children with birth defects that may arise from parents who are too closely related, and who may carry the same deleterious recessive gene. When two individuals share similar genetic characteristics, their relationship may be described as "consanguineous." According to Wikipedia, the terms consanguineous and consanguinity indicate a relationship in which two persons are "of the same blood or origin; specifically: descended from the same ancestor."

It has been known since prehistoric times that closely-related members of a mated pair, be they plants, domesticated animals or humans, are at a much higher risk of having offspring with birth defects and other weaknesses, or to lose their progeny as embryos or fetuses. It has also been recognized since antiquity that outbred offspring tend to have better health and general fitness. This is the origin of the term, "hybrid vigor," or heterosis.

This effect also drives a major facet of human ethical behavior. Few human transgressions are viewed with as much odium is incest; all known cultures have strong taboos prohibiting this activity. Inbreeding avoidance is also seen in many non-human species, including invertebrates.

The deleterious effects of inbreeding are well-explained in Wikipedia:

"Two leading hypotheses explain the genetic basis for fitness advantage in heterosis.

"The overdominance hypothesis implies that the combination of divergent alleles at a particular locus will result in a higher fitness in the heterozygote than in the homozygote. Take the example of parasite resistance controlled by gene A, with two alleles A and a. The heterozygous individual will then be able to express a broader array of parasite resistance alleles and thus resist a broader array of parasites. The homozygous individual, on the other hand, will only express one allele of gene A (either A or a) and therefore will not resist as many parasites as the heterozygote.

"The second hypothesis involves avoidance of deleterious recessive genes (also called the general dominance hypothesis), such that heterozygous individuals will express fewer deleterious recessive alleles than its homozygous counterpart."

Since the MHC region of the genome has a very high degree of variation among individuals, similarity in the MHC region argues for close relationship, and thus for the defective offspring. Use of the present invention for pair matching strongly increases the chances that offspring will be healthy.

For over two centuries in Western cultures, people of childbearing age have been highly mobile and thus often have obscure ancestry. People can thus not always be sure they are not pairing themselves with closely-related partners. The present invention provides a safe, confidential and discreet way of managing this issue.

Increasing Fertility

The present invention includes a method which selects for more diversity in a couple's children's immune systems, increasing the chance that its children will survive, thrive, and increase the couple's fertility.

The term "fertility" is usually defined as a measure: "fertility rate" is the number of children born per couple, person or population. In this Specification, and in the Claims that follow, the term "fertility" is used in a longer-term sense, describing the number of a couple's descendants over a few generations compared to that of the population as a whole.

It has been known since antiquity that couples who are closely related have relatively few children who survive until adulthood. The couples often fail to conceive, and their offspring suffer a higher-than-average number of birth defects. As we have shown elsewhere, fetal loss from defects in the embryo, premature delivery and complications of pregnancy are higher for closely-related couples.

The fertility (as defined above) of couples who are first or second cousins is poor. First and second cousins had very few grandchildren, while third and fourth cousins had the largest number. In more distant relationships, fertility declined, so that sixth cousins have about the same number of grandchildren as first cousins. Fertility tends to level off at seventh cousins and more distant relationships.

This loss of fertility is not inconsistent with the linear increase in attraction and responsivity noted above. It is important to note that humans and their hominid forebears lived for 3 million years—until about 50,000 years ago—in hunting-gathering camps that contained no more than 50 people; usually about 30. Many times, depending on the culture, men or women would move to a neighboring camp to take a mate. Thus the likelihood of outbreeding beyond fifth or sixth cousin was very low, and there was no evolutionary pressure to limit the degree of outbreeding. A linear increase in attraction and responsivity is completely consistent with those anthropological findings.

Increasing Fitness

The present invention increases the likelihood of reproductive success. This benefit is accomplished by ensuring that the couple is not, without its knowledge, closely-enough related that their children run a high risk of defects arising from inbreeding, for example those arising from each partner's carrying a recessive deleterious gene.

The term "fitness" is defined as "the probability of reproductive success through one's own offspring." People who select mates with alleles of genes in the Major Histocompatibility Complex (MHC) that are different from theirs in accordance with the present invention will have more successful pregnancies, offspring with more robust immune systems, and in many cases a greater number of grandchildren. These beneficial consequences comprise the elements of reproductive success.

Enhancing Immune System Diversity

The present invention enhances the immune system diversity of offspring. One method of the invention selects for more diversity in the immune systems of children, increasing the chance that the children will survive and thrive, and since their children will pass their more-diverse genomes to their own children, thus enhancing their chances of survival and reproduction, the couple's fertility is increased.

Genes in the Major Histocompatibilty Complex (MHC), a region of the short arm of Chromosome 6 in humans, contain information on foreign substances from the environment such as bacteria or viruses causing infectious diseases (antigens) that have been experienced and overcome by individuals and their ancestors. Like most genes, MHC genes contain instructions for cells to manufacture proteins. When an MHC protein is made, mechanisms in the cell clip (ligate) short strands of protein (peptides) from the large protein molecule. These ligands or peptides contain information on the molecular structure of the foreign substances listed above. They migrate to the cell's surface, and inform the immune system of the structure of these legacy substances, and are thus also called antigens (antigen is a general name for a substance that elicits an immune response). The antigens generated by the MHC genes may be called either "histocompatibility antigens" or "human leucocyte antigens." Cells bearing these antigens on their surfaces are called antigen-presenting cells. That term applies to any of various cells (as a macrophage or a B cell) that take up and process an antigen into a form that, when displayed at the cell surface in combination with a molecule of the Major Histocompatibility Complex, is recognized by and serves to activate a specific Helper T cell. Helper T cells are an important part of the human immune system.

Alleles in the MHC genes are codominantly expressed, meaning that if the mother and father carry different alleles (that is, variations) of the same gene, each allele is expressed. The offspring thus carry information on the antigens that have beset both of their ancestral lines. For this reason, if a child's parents' MHC alleles are more diverse (that is, if they share fewer alleles in the MHC region), the offspring have innate immunity to a larger number of diseases.

The present invention's matching method, which selects possible parenting partners on the basis of greater diversity in their MHC alleles, also selects for more diversity in the couple's children's immune systems. This increases the chance that their children will survive and thrive, thus increasing the couple's fertility.

The children not only receive information from infections overcome by their parents' ancestors, but also from those overcome by the parents themselves, since the body has a recently-discovered (and quite complex) mechanism to modify its own genome in response to infections. These modified genes are passed on to those of their offspring who are conceived after the parents have survived the infections.

Greater Marital Stability

A match predicted by the present invention leads to greater stability of a couple's marriage. Women who are paired with men who have dissimilar alleles in the Major Histocompatibility Complex (MHC) of their genome are not only more strongly attracted to their mates and are more responsive to them, but are also more faithful to them. Men in such pairings are also more faithful to their partners. Men are more likely to be faithful to a partner who not only holds him in high regard, but who is more responsive to him during coitus. See Garver-Apgar, C. E., Gangestad, S. W., Thornhill, R., Miller, R. D., & Olp, J. J., "Major Histocompatibility Complex Alleles, Sexual Responsivity, and Unfaithfulness in Romantic Couples." Psychological Science, Vol. 17 No. 10, Pages 830-835 (2006).

Pair-bonded women who were near ovulation reported greater extra-pair flirtation and greater mate guarding by their primary partner. As predicted, however, these effects were exhibited primarily by women who perceived their partners to be low on hypothesized good genes indicators (low in sexual attractiveness relative to investment attractiveness). See Haselton, "Conditional expression of women's desires and men's mate guarding across the ovulation cycle," Hormones and Behavior, Vol. 49, Pages 509-518 (2006).

By analyzing the genomes of offspring of an inbred human population, Ober found strong evidence that there was a greater-than-chance probability that a child's parents had assortative (different) alleles in the MHC region. This implies that couples who had different MHC alleles were responsible for more offspring, whether they were married to each other or not, and further implies that those married couples who had different alleles tended to be more faithful. See Ober, C. Weitkamp, L. R., Cox, N., Dytch, H., Kostyu, D., Elias, S., "HLA and mate choice in humans." American Journal of Human Genetics, Vol. 61, Pages 497-504 (1997).

Hormonal birth control ("The Pill") reverses women's preference for complementary MHC alleles. The reason for this is that hormonal birth control (HBC) mimics pregnancy, and that pregnant women prefer to be with their own family, whose MHC alleles are similar to hers. When a woman who is not using hormonal birth control is not pregnant, her unconscious search for the best complement of genes for her children, i.e., a man whose MHC alleles are different from hers, may lead her to be unfaithful to her husband if his alleles are similar to hers.

A couple who meet and marry while the woman is using hormonal birth control is likely to have similar MHC alleles; and thus, it is also more likely that, if for any reason she stops her HBC regimen, she will be less attracted to her husband and more attracted to men with complementary MHC alleles, and thus more likely to stray. Put another way, she will be less attracted to her husband and more likely to stray. The present invention provides a powerful means of counteracting that effect, since it predicts the man's attractiveness to the woman after their marriage has been solemnized, thus leading to a more stable union.

Mate Assessment

The present invention provides the following benefits:

1. Subscribers to online dating and other dating or introduction services will be able to predict a woman's attraction to a candidate man, thus improving the chances of a compatible match.
2. Individuals will be able to compare their genomes with the goal of entering into satisfying and lasting relationships.
3. Couples considering a long-term relationship or marriage will be able to assess the probable stability of that relationship and the prospective health of their offspring.
4. Because the present invention will reduce birth defects and spontaneous abortions, enormous amounts of public and private money will be saved, and will, at least for a few individuals, provide a much higher quality of life.
5. Research has shown that women who have children fathered by a man with assortative (different) alleles in the MHC region have fewer miscarriages and are less likely to experience preeclampsia, a serious complication of pregnancy, and that it is less likely that their children will have birth defects.

In addition to being attracted to men with complementary MHC alleles, heterosexual women who are not using hormonal birth control (HBC) are also sexually more responsive to those men. When women are in physical proximity to men, for example in a social or work setting, they distinguish the degree of difference in their and the man's MHC alleles by scent. Although women are not usually aware of this, numerous studies have proven this beyond reasonable doubt. Surprisingly, in spite of humans' relatively poor sense of smell, people are able to distinguish among MHC variations of the same species of mouse by smell alone. The taste and smell of bodily fluids exchanged during kissing also play an important role in mate assessment.

These odors and tastes play an important role in pair-bonding and the maintenance of relationships, as is dramatically illustrated by the pervasive habit of smelling one's partner's clothes in his absence.

For obvious reasons, none of these means of mate assessment is available to people who have never met; and some substitutes that seem quite reasonable, such as viewing still photographs of partnering candidates, actually result in poorer matches than could be achieved by chance.

Poor matches can result even when the prospective partners are in close contact. The use of hormonal contraceptives such as birth-control pills reverses usual female preferences for male scent, increasing the chances that a union would result in birth defects, pregnancy complications, such as miscarriages and spontaneous abortions, and marital infidelity.

These benefits are limited to heterosexual individuals. People of other sexual orientations have different odor preferences. The relationship prediction methods of the present invention can also be used to assist these prospective couples in finding compatible mates.

Reducing Miscarriages

The present invention reduces the likelihood that a woman will suffer a miscarriage. One embodiment of the invention ensures that a couple is not, without its knowledge, closely-enough related that its children run a high risk of defects arising from inbreeding, for example those arising from each partner's carrying a recessive deleterious gene. Couples without "chemistry" are twice as likely to miscarry.

There is a considerable body of research pointing to the relationship of miscarriages (spontaneous abortions) and pre-term births (premature babies) to parents who have similar alleles (that is, variations) of genes in the Major Histocompatibilty Complex (MHC), a region of the short arm of Chromosome 6 in humans. The antigens generated by the MHC genes are called both histocompatibility antigens and human leucocyte antigens (HLA). In a survey of the field published in 1999, Ober found that "Increased fetal loss rates among couples matching for HLA-B or for the entire haplotype suggest that compatible fetuses are less likely to survive to term than incompatible fetuses." See Ober, Carole, "Studies of HLA, fertility and mate choice in a human isolate," *Human Reproductive Update* 1999 (Publication of the European Society of Human Reproduction and Embryology), Vol. 5, No. 2 Pages 103-107 (1999). Elsewhere in the cited paper, she notes that Komlos and Schacter show "evidence demonstrating increased HLA sharing among couples with recurrent spontaneous abortion (RSA) compared with control couples . . . ." Other work by Ober provides an enormous volume of data supporting the relationship of fetal loss to similarity in MHC alleles. See Komlos, L., Zamir, R., Joshua, H., and Halbrecht, I., "Common HLA Antigens in Couples with Repeated Abortions," Clinical Immunology and Immunopathology 7, Pages 330-335 (1977). See Schacter, B., Muir, A., Gyves, M. et al., "HLA-A, B compatibility in parents of offspring with neural-tube defects or couples experiencing involuntary fetal wastage," The Lancet, Apr. 14, 1979, Pages 796-799.

Differing alleles in the HLA-G gene in the MHC region may decrease the chance of spontaneous abortions and preeclampsia, a complication of pregnancy which endangers both the mother and her fetus.

Preterm births levy an enormous cost on society. The Institute of Medicine (part of the National Academy of Sciences, estimates that, preterm births in the U.S. cost at least $26.2 billion in 2005, or an average of $51,600 per infant.

Women tend to select mates with differing alleles in the MHC region of their genome. The method of the present invention will substantially reduce fetal loss in couples.

Reducing Preeclampsia

The present invention reduces the chance that a woman will suffer preeclampsia in her pregnancy. There is a higher risk of preeclampsia in couples with similar alleles in the MHC region of their genome. There are two mechanisms for this effect:

1. Women who carry a polymorphic allele of the HLA-G gene, which is expressed by the fetus and influences its placenta's attachment to the uterus) are at a higher risk of preeclampsia and fetal loss. The presence of the usual (monomorphic) form of the gene in the father's genome halves the chance that the fetus will inherit (and express) the variant polymorphic form.
2. The incidence of preeclampsia is related to the mother's tolerance to the father's genetic material. This tolerance increases through continued physical contact.

Since marital fidelity and pair bonding are higher between partners who have differing alleles in the MHC region of their genome, the present invention's use of genetic matching to increase the chances of diversity in the MHC regions of the couple's genomes will reduce the chance of preeclampsia in the mother and its consequent risk to her and her unborn child.

Hormonal birth control, e.g, the Pill, reverses women's preference for men with complementary MHC alleles. The reason for this is that the hormones used in hormonal birth control (HBC) are similar to those present in a woman's body during pregnancy, and their effect therefore mimics pregnancy; and that a pregnant woman prefers to be with her own family, whose MHC alleles are similar to hers. When a woman who is not using hormonal birth control is not pregnant, her quest for a good father for her children—a man whose MHC alleles are different from hers—may lead her to be unfaithful to her husband if his alleles are similar to hers.

A couple who meet and marry while the woman is using hormonal birth control is likely to have similar MHC alleles; and thus, it is also more likely that, if for any reason she stops her HBC regimen, she will be less attracted to her husband and more attracted to men with complementary MHC alleles, and thus more likely to stray.

As discussed elsewhere in this Application, if she conceives with her husband and her husband has similar MHC alleles, this may also lead to difficulties in pregnancy, unwanted miscarriages, poor fertility and impaired immunity in the couple's children. The present invention provides a powerful means of counteracting that effect, since it predicts the man's attractiveness to the woman after their marriage has been solemnized, thus leading to a more stable union.

Women who are presented with an array of still photographs of men and are asked to select men with whom they would consider having a relationship tend to select men with similar, not different, MHC alleles. In cultures where arranged marriages are common and in situations in which a matchmaker or other gobetween is involved, and the woman, having selected a man from such a photographic array, is under great pressure to proceed with the relationship, the chances of the woman's not being attracted to the man, and thus having an unsatisfactory relationship and the other adverse effects discussed above, is high. See Roberts, S. Craig, et al., "MHC-assortative facial preferences in humans," Biology Letters, Vol. 1, Pages 400-403 (2005).

In cultures with arranged marriages or in those where matchmakers are used, the bride-to-be is usually quite young and has had little contact with men outside her family. She is therefore not in a position to select among candidates based upon the natural means (scent) at her disposal.

It is therefore of considerable value to dating services, matchmakers, parents in societies in which arranged marriages are common, and to the prospective partners themselves, to be able to predict the woman's attraction to a particular man during the fertile part of a long-term relationship, when for obvious reasons HBC is not used.

VIII. Responsivity

One embodiment of the present invention may be used to predict a good relationship. This prediction may be determined, in whole or in part, upon a woman's responsivity to a prospective male match. In this Specification, and in the Claims that follow, the term "responsivity" is defined as:

Sexual responsivity refers to the extent to which women are willing, interested, and enthusiastic about having sex with a romantic partner, the degree to which they are interested in trying to please a romantic partner sexually, and the degree to which they are sexually "turned on" and satisfied by a romantic partner.

IX. Alternative Method: When a Woman is Using Hormonal Birth Control

Hormonal birth control ("The Pill") reverses women's preference for men with complementary MHC alleles. The reason for this is that the hormones used in hormonal birth control (HBC) are similar to those present in a woman's body during pregnancy, and their effect therefore mimics pregnancy; and that a pregnant woman prefers to be with her own family, whose MHC alleles are similar to hers. When a woman who is not using hormonal birth control is not pregnant, her quest for a good father for her children—a man whose MHC alleles are different from hers—may lead her to be unfaithful to her husband if his alleles are similar to hers.

If a woman who uses the present invention to obtain a relationship prediction uses hormonal birth control, she may be provided with a report or instructions which may help her make a better-informed decision. So, for example, a relationship prediction for a woman using hormonal birth control may be generated based on the woman's preference for a man with complementary MHC alleles.

X. Hormonal Birth Control & Attractiveness

One embodiment of the present invention may be used to predict an enduring relationship between a man and a woman. In this embodiment, a woman is advised that a man may find her less attractive if she changes her hormonal birth control regimen. The man's diminished attraction to the woman results from a change caused when the woman starts or stops using hormonal birth control.

In another embodiment, a website is operated which enables customers to access information presented on the website. The customer may request advice concerning the maintenance of a good relationship. Advice is provided to the customer in response to a request conveyed to the website. In one embodiment of the invention, this advice may include a recommendation that a man may find a woman less attractive if she changes her hormonal birth control regimen. In an alternative embodiment, the customer's request and the advice furnished in response may be conveyed in person, at a doctor's office or clinic, over the telephone, or by some other suitable means.

In yet another embodiment, the website may be used to ask a female if she has recently started or stopped using hormonal birth control, and if she believes that her male mate finds her less attractive since this change in her use of hormonal birth control. These responses are then correlated, and relationship advice is furnished to others based on the correlated data. This relationship advice may be supplied free of charge as a public service.

In this Specification and in the Claims that follow, the terms "hormonal birth control" is intended to include all hormonal contraceptives that contain progestin or one of its analogues and/or estrogen or one of its analogues. They include birth-control pills, certain intra-uterine devices (e.g., Mirena), vaginal rings, Norplant implants, contraceptive injections and their ilk.

XI. Custom-Fabricated Perfumes

FIG. 48 illustrates the step 100 of a customer 10 receiving a custom-formulated perfume 102, "MyAroma™" or "MyCologne™," which contains olfactory reagents that correspond to her genetic attributes, and specifically, which correspond to his or her MHC-derived peptide profile.

FIG. 49 depicts a method 104 of manufacturing a customized perfume 102. General methods for manufacturing compositions for dispensing fragrances, aromas and perfumes are well known in the art. According to the Scented Products Education and Information Association of Canada, ingredients in a typical fragrance "recipe" generally include:

"extracts from plants and flowers (naturals), synthetic recreations (synthetic duplications of natural fragrance materials), synthetic innovations (variations of naturally-occurring materials which have unique olfactory properties).

In general, typical fragrance formulae contain 100-350 ingredients, with an average concentration of usually less than 1%.

"In a perfume, ethyl alcohol (of the same grade and purity as in alcoholic beverages) composes 50-90% of the product, purified water may constitute 5-20% of the product, with the fragrance component accounting from 10-30% of the finished product. Also present are UV inhibitors (to prevent degradation in the bottle) and any additional colouring agents."

SPEIAC, 20 Britannia Road East, Suite 102, Mississauga, Ontario L4Z 3L5.

In one embodiment of the present invention, appropriate combinations of biological, synthetic or other agents such as peptides or other substances are added as active ingredients 106 to a base 108 to a mixture, together with and/or any other suitable solvents, stabilizers, agents, preservatives, dispersants, inhibitors or components. In one embodiment, the base is a solvent, such as alcohol or water. These biological agents are selected to match a genetic attribute possessed by a person.

In one implementation, the perfume or cologne 102 made in accordance with the invention contains substances which are complementary to the user's Major Histocompatibility Complex (MHC profile), which will be attractive to the same user. In the same implementation, that person may ask a spouse or mate to wear this perfume or cologne 102, which pleases the person for whom the customized perfume or cologne was made. The present invention includes both perfume or cologne intended to be used by a person selecting the perfume or cologne for herself or himself, as well as an "inverse perfume or cologne," which is selected by one person and used by another.

The biological agents may be selected to promote the responsivity of the person using the mixture, or may be selected to promote the responsivity of another person using the mixture. The biological agents in the mixture may be used to broadcast or indicate sexual compatibility, interest, awareness or attraction. As an alternative, the biological agents may be selected to promote confidence, self-esteem or the interest or attraction of another. The invention may be used to promote relationships between members of the opposite sex, or between members of the same sex.

The specific composition of the mixture may take many forms, including, but not limited to a perfume, a cologne, a salve, a paste, an aerosol spray, a powder, or a cosmetic. The cosmetic may include skin cream, lipstick, lip balm, gel, ointment, colorant, or some other preparation that be applied to the body. The mixture is generally intended to be applied to, dispensed on or worn on the skin or hair, but may be applied on or used in conjunction with an article of clothing, which may be impregnated with the active ingredients. In yet another embodiment, the perfume 44 may be encapsulated or contained in a pill or medication that is taken internally, and which is then secreted through the skin or which causes a biological reaction which produces or mimics an odor. The mixture may also be dispensed using a variety of devices, including, but not limited to air fresheners, aroma-dispensing devices, candles and incense.

This specialized perfume 102 contains a strong preparation of personal peptides, enabling the user to "broadcast" his or her "MHC" over a wide area, and increasing his or her chances of meeting a compatible partner.

The MHC is a cluster of genes that determines details of cellular surfaces and thus immune responses, and specifies certain peptides that appear in skin secretions and urine. These peptides are responsible for odors which uniquely identify individuals who are not identical twins. Detailed information concerning the MHC may be found in Leslie A. Knapp's publication entitled *The ABCs of MHC*, published in Evolutionary Anthropology 14:28-37 (2005) Wiley-InterScience. MyAroma™, MyPerfume™, MyEssence™ are Trade & Service Marks owned by the Assignee of the Present Patent Application.

XII. A Graphical Aid for Interpreting Test Results

FIG. 49 presents one particular version of a graphic representation or "Genoscope™," which illustrates a hypothetical portion of test results for a customer, and which enables the customer to easily understand the quality of a match with another person.

The same prediction method described elsewhere in this Application is useful in the absence of a dating service, or in situations where a person prefers to make their own initial contacts with prospective mates or in cases in which a person wishes to assess a potential mate from a field of known candidates. In one embodiment, a person (hereafter the "User") submits his or her tissue, fluid or other biological sample to a laboratory for typing, and the laboratory provides the User with an alphanumeric code (the "Code") which describes his or her genetic information, i.e., genome in the MHC region and any other regions of interest. The User may then compare his or her Code with that of another User to estimate their mutual compatibility and thus the quality of a romantic relationship that might ensue. Each User would be provided with a written guide or computer program for comparing the data embedded in the Codes and estimating the quality of the contemplated relationship.

In another embodiment, the laboratory would keep records of the genomes or Codes of each User. On request, the laboratory would compare the User's genomes or Codes for compatibility and issue a report.

An example of such a report, in easily-understood graphical form, is shown in FIG. 49. A variety of symbols are presented in a grid along rows and columns. The more symbols match, the more genomes are similar, which predict a bad match. The stars in the center of FIG. 49 indicate the approximate strength or quality of a match, with zero being the lowest quality, and five stars representing the highest. An added feature of the report could be a Compatibility Score which rates the predicted quality of the contemplated relationship in a way that can be compared with other relationships, for example on a scale of one to ten, with ten being the best possible genetic compatibility score.

XIII. Comparing Types of Credit Card Spending to Predict Good Matches

Section I of this Specification describes an embodiment of the invention which enables customers to visit a website to supply information about themselves, and their ideal match. In this implementation of the invention, information is stored electronically in a computer database. In alternative embodiments, information about customers and their test results may be recorded in some other form of database, whether in electronic, paper or other means of media or storage.

In yet another embodiment of the invention, this database of information and/or records may be maintained by an introduction service, which may include a dating or matching service, or some other means for enabling, furnishing or assisting people find romantic or other matches. The introduction service may or may not utilize the Internet and/or electronic record keeping.

This information that is supplied by customers using a website are referred to as personal "attributes" or "characteristics" which are compared to assist in the suggestion of a good match between two individuals.

In another embodiment of the invention, these characteristics are obtained from a database of records. This database may or may not be "external" to a server, computer or other suitable information appliance 110 which seeks these records. If the database is external or remote from the server, the server may access the database using any suitable network, connection or means of communication, including the Internet. FIG. 50 is a schematic diagram of one embodiment of the invention, which includes a server 110 that communicates with a local or remote electronic database 112 of records 114. The server 110 issues a inquiry to the database, where records 114 are searched and then returned to the server 110.

In one particular implementation of the invention, the database of records 112 contains credit card statements. Two examples are shown in FIGS. 51 and 52. In FIG. 51, a portion of John's credit card statement 112A is depicted. In FIG. 52, a portion of Mary's credit card statement 112B is depicted.

FIG. 53 portrays the implementation of one method of the present invention. After the server obtains the desired records 114A and 114B from the databases 112A and 112B, the records of the two individuals, John and Mary, are compared. In this example, John's statement contains charges from an Italian restaurant and from an airline that provides service to Hawaii. Mary's statement contains charges from a different Italian restaurant and from a hotel in Hawaii. When these two statements are compared, it appears that there is a substantial probability that both John and Mary like Italian food and trips to Hawaii. Although these comparisons 116 may not be valid in every instance, they may provide a reliable basis for helping to predict a good match 118 between two persons.

In this embodiment of the invention, electronic devices such as a server or computer 110 runs a website which is used by individuals to obtain a good match suggestion. The individuals send use the website as a mechanism for sending and/or receiving information, including personal characteristics, interests or attributes. In this embodiment, the server or computer 110 runs software which receives, stores, compares, evaluates and processes the information supplied by these individuals to produce the desired result, the suggestion of a good match. The desired result is stored in the server, and may be conveyed back to the individual using privileged access to a secured portion of the website.

XIV. Comparing Credit Card Purchase Histories & Marital Status to Predict Good Matches In yet another embodiment of the invention, credit card statements are analyzed, and general spending habits are compared. As an example, if John and Mary both have extensive charges on their credit cards, they may be determined to be a good match.

In another embodiment of the invention, relationship predictions are generated by analyzing the spending habits of a group of consumers, and then analyzing the stability of marriages of that same group of consumers.

The first step of this invention includes the analysis of the spending habits a set of a set of individuals during a time period when then are unmarried. In the second step of this invention, information about the same individuals is obtained to determine which individuals in this set were in stable marriages. In the third step of this invention, the spending habits of individuals in stable marriages are compared to determine what combinations of purchasing behavior categories result in successful marriages. Once it is known which combinations of purchasing behaviors are most likely to help create a successful marriage, good predictions can be made based upon the spending habits of single persons.

FIG. 54 provides a schematic illustration 120 of one embodiment of the invention. A group of individuals 122, including females 124 and males 126 with credit card purchase histories while they are single, are represented in a database. This database also includes data for married couples 128, including females 130 and males 132. Within this database, the females and males are grouped into catagories based upon their purchase histories before they were married.

FIG. 55 offers a schematic view of another database 134, which stores marriage histories, based upon purchase behavior categories. The data collected for a first group of couples is represented in the section of the database 136 that is labeled "Stayed Married." The data collected for divorced individuals is represented in the section of the database labeled 138.

FIG. 56 furnishes a flow chart 140 which illustrates one embodiment of the invention. In the first step 142 of this embodiment, purchase data is assembled and recorded for groups of men and women. In the second step 144, the purchase data is analyzed to determine a purchase behavior category. In a third step 146, purchase behavior categories are compared. If the purchase categories do not suggest compatibility, then no match is generated in step four 148. If the purchase categories do suggest compatibility, a match is recommended in step five 150.

XV. Using Social Networks to Generate Personal Attributes and to Predict a Good Match FIGS. 57 through 60 depict another embodiment of the invention. Information and/or data may be obtained from a variety of websites that may be used to assist in determining a good match. In one specific implementation of the invention, information may be obtained from the facebook website. The facebook website contains pages that provide information about its members. Each member provides information about herself or himself which is then made available for viewing by others. This information, which may be generally referred to as "personal interests" may include, but is not limited to, the following categories:

Music
Games
TV Shows
Places
Organizations
Non-Profits
Celebrities/Public Figures
Stores
Sports Teams
Products
Bars/Clubs Three sample fictitious facebook webpages are illustrated in FIGS. 57, 56 and 57. Each of these three fictitious members is identified on each with a name and a photo, and has provided several interests. In one embodiment of the invention, a server obtains access to webpages 152, 156 and 160 and retrieves some or all of the attribute information 154, 158 and 162 shown on each page. Once this information is retrieved, it is compared and is then used to assist in the suggestion of a good match between two individuals.

FIG. 57 is a diagram 118 which shows how the information obtained from external webpages is used to assist in the process of suggesting a good match.

In one embodiment of the invention, a matching algorithm is employed to suggest a good match. One such algorithm is described in Pending U.S. patent application Ser. No. 11/881,153 by Lawrence Weill et al., filed on 24 Jul. 2007, entitled Searching Methods.

This embodiment of the invention may be practiced using a wide variety of web pages 152, 156 and 160. Wikipedia lists many sites, including, but not limited to, MySpace, MyLife, MyHeritage and LinkedIn. The present invention may be practiced using any database which contains information that would be useful to the process of suggesting good matches.

Although the description of these particular embodiments of the invention refers to external webpages, the invention encompasses using a server, computer or some other suitable information appliance to search for and then retrieve information or data which may be useful in predicting or suggesting a good match. The form of the external information may or may not be formatted or memorialized as a webpage.

XVI. Internet Matchmaking

FIG. 61 provides a schematic representation of a portion of a social network 168. The network portion includes a number of members. In this example, this segment of the network includes six members: Mary, Suzie, Jane, Bonnie, Tiffany and Carol. Each of these members has her own webpage, which publishes information about each member, and which is readily accessible to all the members of this network, as well as to persons who are not members of this network.

In this embodiment of the invention, all of the participants must be members of an existing or external social network which enables its members to publish information about themselves. This external social network may be any group of persons who may be linked and/or may communicate using a computer or some other suitable information appliance or device. As examples, the social network may be facebook or MySpace.

FIG. 62 illustrates the first step 170 in the implementation of one embodiment of the invention. One member of the external social network, Mary, is shown viewing the social network website. Her computer screen displays an invitation 172 to join a separate website, the Internet Matchmakers Club.

In FIG. 63, Mary is asked to create her own Circle of Friends for the IMM, Club in a second step 174 of this embodiment. She may accomplish this task by selecting, and then viewing, the webpages of ten other persons who are members of the external social network. To create her Circle of IMM Club Friends, Mary visits ten webpages within the external social network. These ten webpages may belong to her friends, or may be selected at random. In alternative embodiments of the present invention, Mary may add more than ten friends to her IMM Club Circle of Friends. For the purpose of simplicity, this description of one embodiment of the invention is limited to ten friends.

FIG. 64 shows the details of a hypothetical web page 176 from the social network. A photo of the member, Karen, is presented in the upper left corner. A variety of personal information 178, including characteristics, favorites and personality traits are presented along the lower portion of her webpage. Mary completes her task of creating her Circle of IMM Club Friends by reading Karen's personal information, and copying all or a portion of Karen' personal information into a message that will be sent to the IMM Club. As an example, Mary's message 180 might resemble the following text:

To: IMM Club
Message from Member: Mary
Topic: My IMM Club Circle of Friends—Report for Karen
Dear IMM Club:
Please add Karen to my Circle of IMM Club Friends. I have read her webpage, and she lists the following personal information:
Interests: 4H, Girl Scouts
Favorites: Johnny Depp
Activities: Soccer, dancing FIG. 65 shows another step 182 of this embodiment, and depicts a screen shot 184 from Mary's computer after she has completed ten reports for her Circle of IMM Club Friends. Mary has not only selected and reported ten friends whom she will try to match with another person, but has also suggested the potential matches. As is the case with her ten initial friends, her nominees for matches may or may not be personally known to Mary. The only limitation is that all of these participants must be members of the external social network with published webpages that present personal information. In an alternative embodiment of the invention, more than one external social network may be used to practice the present invention. For this example, only one external social network is employed. In this description of the present invention, the term "external social network" refers to an existing website which has members who publish information about themselves on their own dedicated webpage. In alternative embodiments of the invention, the external social network website and the website for the IMM Club may be integrated into one website.

After Mary has completed her reporting task, messages are sent to her friends from the IMM Club, as shown in a step of the invention 186 illustrated by FIG. 66. A first set of messages notifies each of Mary's ten original friends that she has designated them as part of her Circle of IMM Club Friends. The personal information that Mary has reported to the IMM Club is then processed to suggest good matches.

The IMM Club may use a variety of matching algorithms to suggest good matches based on the input of personal information from many matchmakers. Examples of algorithms which may be used to predict good matches are described in Pending U.S. patent application Ser. No. 11/881,153, filed on 24 Jul. 2007 and entitled Searching Methods. The Specification and Drawings of U.S. Ser. No. 11/881,153 are hereby incorporated into the Present Patent Application by reference.

In this Specification and in the Claims that follow, the term "good match" is intended to encompass any relationship between two persons which may be characterized as a beneficial friendship, romantic affiliation, business acquaintance or some other successful introduction or pairing.

In another step 188 of the invention, another set of messages is then sent out from the IMM Club to Mary's Circle of Friends, as shown in FIG. 67. These messages inform each of Mary's ten friends that they have been matched with other members of the external social network, and invites them to contact the person with whom they have been matched. The persons who have been matched with Mary's ten friends each receive their own message from the IMM Club, informing them of the match, and inviting them to participate. In one embodiment of the invention, Mary, the original matchmaker, may also receive copies of these messages to her ten friends and to the ten nominated matches.

Matchmakers may earn rewards for participating in the IMM Club, and for suggesting successful matches. FIG. 68 illustrates this step 190 of the invention, and provides a screen shot from Mary's computer, and shows her matchmaking rewards page. As matches progress from introductions to meetings to relationships, Mary earns IMM Club credits, or some other suitable reward. These credits may be used to purchase goods and/or services from sponsors who advertise on the IMM Club webpage, as shown in another alternative step 192 of the invention shown in FIG. 69. Once Mary reaches the age of eighteen, she may also redeem her IMM Club rewards to pay for a membership in an on-line dating and/or matching service, as shown in another alternative step of the invention 194 shown in FIG. 70.

Glossary

Allele:
Either of a pair of alternative Mendelian characters (as smooth or wrinkled seed in the pea) (Webster).
Antigen:
1. A usually protein or carbohydrate substance (as a toxin, enzyme, or any of certain constituents of blood corpuscles or of other cells), that when introduced into the body stimulates the production of an antibody;
2. A substance that reacts in complement fixation with an antibody to bind complement, the antigen and antibody usually being specific (Webster).
Antigen-presenting cell:
Any of various cells (as a macrophage or a B cell) that take up and process an antigen into a form that when displayed at the cell surface in combination with a molecule of the major histocompatibility complex is recognized by and serves to activate a specific Helper T cell.
Attractive:
Having qualities that arouse interest, pleasure, or affection in the observer. attractiveness.
Attribute:
A quality, character, or characteristic ascribed usually commonly: a: a characteristic either essential and intrinsic or accidental and concomitant b: a quality intrinsic, inherent, naturally belonging to a thing or person (Webster).
Attribute (genetic):
An attribute as defined above which is controlled or caused by a creature's genome.
Body odor:
The characteristic odor of a living animal body.
Chromosome:
One of the more or less rodlike chromatin-containing basophilic bodies constituting the genome and chiefly detectable in the mitotic or meiotic nucleus that are regarded as the seat of the genes, consist of one or more intimately associated chromatids functioning as a unit, and are relatively constant in number in the cells of any one kind of plant or animal (Webster).
Codominant genes:
A set of two or more alleles, each expressed phenotypically in the presence of the other (Online Medical Dictionary).
Consanguinity:
The quality or state of being related by blood or descended from a common ancestor (Webster).
Diversity in the MHC regions:
The degree to which the alleles in the Major Histocompatibility Complex differ between two individual members of the same species:
Dominant gene:
A gene that is expressed phenotypically in heterozygous or homozygous individuals.
Fertility:
Actual reproductive capacity as measured by production of offspring (Webster). In the context of this Application, this includes descendants more distant than direct offspring.
Fitness:
The fitness of the individual—having an array x of phenotypes—is the probability, s(x), that the individual will be included among the group selected as parents of the next generation." See Hartl, D. L. A Primer of Population Genetics. Sinauer, Sunderland, Mass., 1981 (Wikipedia).
Gene:
One of the elements of the germ plasm serving as specific transmitters of hereditary characters and usually regarded as portions of deoxyribonucleic acids linearly arranged in fixed positions and as functioning through control of the synthesis of specific polypeptide chains.
Group frequency:
The frequency of occurrence of a particular group of genes or alleles in a population.
Haplotype:
A combination of alleles at multiple loci that are transmitted together on the same chromosome. Haplotype may refer to as few as two loci or to an entire chromosome depending on the number of recombination events that have occurred between a given set of loci (Wikipedia).
HBC:
See hormonal birth control.
HBC regimen:
The process of maintaining an effective level of birth-control hormones in one's body.

Heterozygote:
A cell formed by the union of heterozygous gametes: a fertilized egg: broadly: the developing individual produced from such a cell.
Heterozygous:
Producing two types of gametes with respect to one or more allelomorphic characters.
Histocompatibility antigen:
Any of the antigenic glycoproteins on the surface membranes of cells that enable the body's immune system to recognize a cell as native or foreign and that are determined by the major histocompatibility complex.
HLA:
See Human Leucocyte Anitgen.
Homozygote:
A cell formed by the union of homozygous gametes: a fertilized egg: broadly: the developing individual produced from such a cell.
Homozygous: possessing genes for only one member of at least one pair of allelomorphic characters.
Hormonal birth control (HBC):
The use of drugs containing progestin (or one of its analogues) and/or estrogen (or one of its analogues) or any other natural or synthetic hormone to control ovulation, implantation or conception and thus prevent unwanted pregnancy. These drugs may be administered orally, parentarilly or by any other means.
Human leukocyte antigen:
Any of various proteins that are encoded by genes of the major histocompatibility complex in humans and are found on the surface of many cell types (as white blood cells).
Infectious disease:
A disease caused by the entrance into and growth and multiplication in the body of bacteria, protozoans, fungi, or analogous organisms (such as filterable viruses).
Immune system diversity:
The ability of a creature's immune system to recognize a variety of threats.
Locus, plural loci:
A fixed position on a chromosome such as the position of a biomarker that may be occupied by one or more genes.
Major Histocompatibility Complex:
A group of genes that function especially in determining the histocompatibility antigens found on cell surfaces and that in man comprise the alleles occurring at four loci on the short arm of chromosome 6—abbreviation MHC.
Marital stability:
The degree to which a marriage persists.
MHC: See Major Histocompatibility Complex.
Ovulation cycle:
In a mammal, the periodic release of eggs into the uterus. More generally, the cycle which includes menstruation, ovulation, and in most mammals, estrus.
Peptide:
Any of a class of amides that are derived from two or more amino acids by combination of the amino group of one acid with the carboxyl group of another, that yield these acids on hydrolysis, that are classified according to the number of component amino acids, and that are obtained by partial hydrolysis of proteins or by synthesis (as from alpha-amino acids or their derivatives). A chain of amino acids produced by a living cell.
Perfume:
A substance that emits an odor.
Preeclampsia:
A toxic condition developing in late pregnancy characterized by a sudden rise in blood pressure, excessive gain in weight, generalized edema, albuminuria, severe headache, and visual disturbances (Webster's Unabridged).
Prediction:
An inference regarding a future event based on probability theory Webster's Unabridged).
Polymorphic:
Having or occurring in several distinct forms: exhibiting polymorphism. "Polymorphic" refers to the rare occurrence of a variant of the usually-monomorphic HLA-G gene.
Population dataset:
A set of data derived from statistics from a study of population of humans.
Recessive gene:
A gene that is phenotypically expressed in the homozygous state but has its expression masked in the presence of a dominant gene.
Relationship:
The state of affairs existing between two people or among two or more people.
Responsivity:
The extent to which women are willing, interested, and enthusiastic about having sex with a romantic partner, the degree to which they are interested in trying to please a romantic partner sexually, and the degree to which they are sexually "turned on" and satisfied by a romantic partner.
Citations marked "Webster" are from Webster's Third New International Dictionary, Unabridged. Merriam-Webster, 2002.

CONCLUSION

Although the present invention has been described in detail with reference to one or more preferred embodiments, persons possessing ordinary skill in the art to which this invention pertains will appreciate that various modifications and enhancements may be made without departing from the spirit and scope of the Claims that follow. The various alternatives for providing a Relationship Prediction System that have been disclosed above are intended to educate the reader about preferred embodiments of the invention, and are not intended to constrain the limits of the invention or the scope of Claims.

| LIST OF REFERENCE CHARACTERS | |
|---|---|
| 10 | Woman |
| 11 | Personal computer |
| 12 | Internet Dating Service Website |
| 13 | Web page for opening new account |
| 14 | Web page for placing order |
| 15 | Test Kit |
| 16A | Attributes describing customer |
| 16B | Attributes describing customer's match |
| 17 | Telephone |
| 18 | Retail store |
| 19A | Physician or health care provider |
| 19B | Religious leader or cleric |
| 20 | Bottle of cleaning solution |
| 22 | Cotton ball |
| 24 | Sample patch |
| 24C | Central area of patch |
| 24S | Strips extending away from central area |
| 25 | Plaster |
| 26 | Antibiotic |
| 27 | Adhesive |
| 28 | Sealable plastic bag |
| 30 | Mailing envelope, pouch or box |
| 32 | Lab technician |
| 34 | Sample analyzer |

LIST OF REFERENCE CHARACTERS

| | |
|---|---|
| 35 | Analysis results |
| 36 | Good matches suggested to customer on website |
| 37 | Test results received from physician |
| 38 | Postal worker |
| 40 | Tissue sample obtained from cheek swab |
| 42 | Shopping mall |
| 44 | Kiosk |
| 46 | Odor sample captured from air surrounding person |
| 48 | Collect sample |
| 50 | Open saliva collection cup |
| 52 | Screw cap on cup and mix sample |
| 54 | Cap |
| 56 | Place closed cap in bag and seal |
| 58 | Place bag in mailer |
| 60 | Seal mailing box |
| 62 | Mail box containing saliva sample to laboratory |
| 64 | Laboratory collection kit preparation tasks |
| 66 | Internet Dating Service tasks |
| 68 | Customer tasks |
| 70 | Laboratory analysis, matching and reporting tasks |
| 72 | Dating Service and laboratory cooperative tasks |
| 74 | Graph of MHC alleles shared on the horizontal axis, a female sexual responsivity to partner on the vertical axis |
| 76 | Bar chart showing the number of MHC alleles shared on the horizontal axis, and the expected female sexual responsivity to partner on the vertical axis |
| 78 | Chart that shows the relationship of alleles in the MHC Group on Human Chromosome No. 6 |
| 80 | MHC Allele Groups |
| 82 | HLA-A Allele Group Frequency for a European Population Dataset |
| 84 | HLA-B Allele Group Frequency for a European Population Dataset |
| 86 | HLA-DRβ1 Allele Group Frequency for a European Population Dataset |
| 88 | Allele Group Frequencies |
| 90 | A/B/DR 1 Group Haplotype Frequency |
| 94 | Man using a MateFinder ™ device |
| 96 | MateFinder ™ device |
| 98 | Detailed view of a MateFinder ™ device |
| 100 | Woman whose tissue sample has already been analyzed receives a custom-formulated perfume which contains aromas that correspond to her genetic attributes |
| 102 | Custom perfume based on genetic attributes |
| 104 | Method of manufacturing a customized perfume |
| 106 | Active ingredients |
| 108 | Solvent or base |
| 110 | Server |
| 112 | Database of records |
| 114 | Records or information |
| 116 | Webpages |
| 118 | Good match |
| 120 | Alternative embodiment |
| 122 | Individuals |
| 124 | Females |
| 126 | Males |
| 128 | Married couples |
| 130 | Females from married couples |
| 132 | Males from married couples |
| 134 | Database |
| 136 | "Stayed Married" section of database |
| 138 | "Divorced" section of database |
| 140 | Flow chart |
| 142 | First step |
| 144 | Second step |
| 146 | Third step |
| 148 | Step four |
| 150 | Step five |
| 152 | Webpage |
| 154 | Attribute information |
| 156 | Webpage |
| 158 | Attribute information |
| 160 | Webpage |
| 162 | Attribute information |
| 168 | Social network |
| 170 | First step |
| 172 | Invitation |
| 174 | Second step |
| 176 | Webpage |
| 178 | Personal attribute information |
| 180 | Message to report attribute information |
| 182 | Additional step |
| 184 | Screen shot |
| 186 | Additional step |
| 188 | Additional step |
| 190 | Additional step |
| 192 | Alternative step |
| 194 | Alternative step |

What is claimed is:

1. A method comprising the steps of:
providing a website; said website being operated on a server; said website being accessible to a plurality of customers; said plurality of customers each generally using an information appliance to access said website;
collecting information regarding a marital status history from some of said plurality of customers;
accessing a database of records; said records containing attribute information regarding a plurality of individuals;
said records pertaining to a description of spending habits of said plurality of individuals; and
comparing said description of spending habits and said marital status history of two of said plurality of individuals to predict a good match; said good match being reported back to some of said plurality of customers on their information appliance.

2. A method as recited in claim 1, in which said records are credit card statements.

3. A method as recited in claim 1, in which said marital status history includes information concerning martial stability.

4. A method as recited in claim 1, in which said good match is predicted by comparing spending habits of a set individuals during a time period when then are unmarried, and then by determining which individuals in this set were in stable marriages.

5. A method as recited in claim 1, in which said good match is predicted by comparing the spending habits of individuals in stable marriages to determine what combinations of purchasing behavior categories result in successful marriages.

6. A method comprising the steps of:
providing a website; said website being operated on a server; said website being accessible to a plurality of individuals;
said plurality of individuals including a first person who acts as a matchmaker, a second set of persons who are identified by said matchmaker as a set of friends, and a third person who is determined to be a good match for one of said friends;
said plurality of individuals each having an information appliance to access said website; each of said plurality of individuals being a member of an external social networking website;
inviting a first person among one of said plurality of individuals to report personal attribute information that suggests a good match; said personal attribute information being available on published pages of an external social networking website; said individual generally using an information appliance to report personal attribute information; and using said personal attribute information to predict a good match; said good match being conveyed to one of said plurality of individuals on their information appliance.

7. A method as recited in claim 6, in which said personal attribute information is reported in a message from said first person to said server.

8. A method as recited in claim 6, in which said good match is suggested in a message from said server to said second and third persons.

9. A method as recited in claim 8, in which said messages from said server to said second and third persons are copied to said first person.

10. A method as recited in claim 6, in which said first person earns a reward for suggesting a match.

11. A method as recited in claim 6, in which an advertiser supports said website by placing an advertisement on said website.

12. A method as recited in claim 11, in which said first person may redeem for a product offered by said advertiser.

13. A method as recited in claim 11, in which said first person may redeem for a service offered by said advertiser.

14. A method as recited in claim 11, in which said first person may redeem for a service offered by an on-line dating website.

* * * * *